US011319564B2

(12) United States Patent
Louis et al.

(10) Patent No.: US 11,319,564 B2

(45) Date of Patent: May 3, 2022

(54) ENHANCED METABOLITE-PRODUCING YEAST

(71) Applicant: ADISSEO FRANCE S.A.S., Antony (FR)

(72) Inventors: Dominique Louis, Forges les Bains (FR); Karine Jaillardon, Saint Michel sur Orge (FR); Dominique Thomas, Gif sur Yvette (FR)

(73) Assignee: ADISSEO FRANCE S.A.S., Antony (FR)

( * ) Notice: Subject to any disclaimer, the term of this patent is extended or adjusted under 35 U.S.C. 154(b) by 173 days.

(21) Appl. No.: 16/628,367

(22) PCT Filed: Jul. 10, 2018

(86) PCT No.: PCT/EP2018/068720

§ 371 (c)(1),
(2) Date: Jan. 3, 2020

(87) PCT Pub. No.: WO2019/011948

PCT Pub. Date: Jan. 17, 2019

(65) Prior Publication Data

US 2020/0224229 A1 Jul. 16, 2020

(30) Foreign Application Priority Data

Jul. 11, 2017 (EP) .................................... 17305911

(51) Int. Cl.

| | |
|---|---|
| ***C12P 13/08*** | (2006.01) |
| ***C12N 1/16*** | (2006.01) |
| ***C12N 9/00*** | (2006.01) |
| ***C12N 9/10*** | (2006.01) |
| ***C12N 9/12*** | (2006.01) |
| ***C12N 9/88*** | (2006.01) |
| ***C12N 15/52*** | (2006.01) |
| ***C12N 15/81*** | (2006.01) |
| ***C12N 9/04*** | (2006.01) |

(52) U.S. Cl.

CPC ................ *C12P 13/08* (2013.01); *C12N 1/16* (2013.01); *C12N 9/0006* (2013.01); *C12N 9/1003* (2013.01); *C12N 9/1205* (2013.01); *C12N 9/88* (2013.01); *C12N 15/52* (2013.01); *C12N 15/81* (2013.01); *C12Y 101/01043* (2013.01); *C12Y 101/01049* (2013.01); *C12Y 102/01076* (2013.01); *C12Y 207/0104* (2013.01); *C12Y 401/01031* (2013.01); *C12Y 401/01032* (2013.01)

(58) Field of Classification Search

None

See application file for complete search history.

(56) References Cited

U.S. PATENT DOCUMENTS 4,439,525 A 3/1984 Shay et al.

FOREIGN PATENT DOCUMENTS

| | | | |
|---|---|---|---|
| WO | 03/036296 | A1 | 5/2003 |
| WO | 12/097091 | A2 | 7/2012 |
| WO | 2019/011948 | A1 | 1/2019 |

OTHER PUBLICATIONS

Kuby, Stephen A. et al. "Glucose 6-Phosphate Dehydrogenase (Crystalline) from Brewers' Yeast". Dehydrogenases and Oxidases Methods in Enzymology, vol. 23, pp. 116-125, 1966.

He, Weiwei et al."Crystal structure of *Saccharomyces cerevisiae* 6-phosphogluconate dehydrogenase Gnd1". BMC Structural Biology, vol. 7 No. 38, pp. 1-9, 2007.

Susan-Resiga et al., "Proton Donor in Yeast Pyruvate Kinase: Chemical and Kinetic Properties of the Active Site Thr 298 to Cys Mutant," Biochemistry, 2004, vol. 43, pp. 15230-15245.

Castaño-Cerezo et al., "An insight into the role of phosphotransacetylase (pta) and the acetate/acetyl-CoA node in *Escherichia coli*," Microbial Cell Factories, 2009. vol. 8, No. 54.

Yamagata, Shuzo, "Partial Purification and Some Properties of Homoserine O-Acetyltransferase of a Methionine Auxotroph of *Saccharomyces cerevisiae*," Journal of Bacteriology, Aug. 1987, vol. 169, No. 8, pp. 3458-3463.

Ravanel et al., "Methionine Biosynthesis in Higher Plants. I. Purification and Characterization of Cystathionine g-Synthase from Spinach Chloroplasts," Archives of Biochemistry and Biophysics, Jan. 10, 1995, vol. 316, No. 1, pp. 572-584.

Mannhaupt et al., "Yeast homoserine kinase—Characteristics of the corresponding gene, THR1, and the purified enzyme, and evolutionary relationships with other enzymes of threonine metabolism," Eur. J. Biochem., 1990, vol. 191, pp. 115-122.

Noor et al., "Allosteric NADP-glutamate dehydrogenase from aspergilli: purification, characterization and implications for metabolic regulation at the carbon-nitrogen interface," Microbiology, 2005, vol. 151, pp. 1409-1419.

(Continued)

*Primary Examiner* — Suzanne M Noakes

(74) *Attorney, Agent, or Firm* — Oliff PLC

(57) ABSTRACT

Metabolites produced by a microorganism using more particularly oxaloacetate as substrate or co-substrate upstream in the biosynthesis pathway. There is indeed a need in the art for transformed, in particular recombinant, microorganisms having at least an increased ability to produce oxaloacetate, thus allowing an increased capacity to produce oxaloacetate-derived amino acids and amino acid derivatives, the oxaloacetate-derived amino acids and amino acid derivatives being termed oxaloacetate derivatives. The solution is the use of a genetically modified yeast including many modifications as described in the present text.

20 Claims, No Drawings

Specification includes a Sequence Listing.

(56) References Cited

OTHER PUBLICATIONS

Cahyanto et al., "Regulation of aspartokinase, aspartate semialdehyde dehydrogenase, dihydrodipicolinate synthase and dihydrodipicolinate reductase in Lactobacillus plantarum," Microbiology, 2006, vol. 152, pp. 105-112.
Schildkraut et al., "Threonine Synthetase-Catalyzed Conversion of Phosphohomoserine to a-Ketobutyrate in Bacillus subtilis," Journal of Bacteriology, Sep. 1973, vol. 115, No. 3, pp. 777-785.
Halasz, Anna; Beata, Matrai and Muayad, Ali; "Study of the Sulphur Metabolism of Methionine-Rich Yeasts".; Periodica Polytechnica Ser. Chem. Engl.; vol. 40; pp. 53-78 (1996).
Xiaojing, Xu; Limin, Cao and Xun, Chen; "Elementary Flux Mode Analysis for Optimized Yield in Anaerobic Fermentation of Glucose with *Saccharaomyces cerevisiae*".; Chinese Journal of Chemical Engineering; vol. 16; pp. 135-142 (2008).
Shen, et al.; "An efficient xylose-fermenting recombinant *Saccharomyces cerevisiae* strain obtained through the adaptive evolution and its global transcription profile".; Appl Microbiol Biotechnol; vol. 96; pp. 1079-1091 (2012).
Kim, et al.; "A systems-level approach for metabolic engineering of yeast cell factories".: FEMS Yeast Res; vol. 12; pp. 228-248 (2012).
Van der Werf, et al.; "Environmental and physiological factors affecting the succinate producte ratio during carbohydrate fermentation by *Actinobacillus* sp. 130Z".; Arch Microbiol; vol. 167; pp. 332-342 (1997).
Lopez de Filipe, F. and Hugenholtz, J.; "Purification and characterisation of the water forming NADH-oxidase from Lactococcus lactis".; International Dairy Journal; vol. 11; pp. 37-44 (2001).
Loizeau, et al.; "Regulation of One-Carbon Metabolism in *Arabidopsis*: The N-Terminal Regulatory Domain of Cystathionine γ-Synthase is Cleaved in Response to Folate Starvation".: Plant Physiology; vol. 145; pp. 491-508 (2007).
Keren, et al.; "Promoters maintain their relative activity levels under different growth conditions".; Molecular Systems Biology; vol. 9; pp. 1-17 (2013).
Stadtman, et al.; "Feed-back Inhibition and Repression of Aspartokinase Activity in *Escherichia coli* and *Saccharomyces cerevisiae*".; The Journal of Biological Chemistry; vol. 236; pp. 2033-2038 (1961).
Mark Hochstrasser; "Ubiquitin-Dependent Protein Degredation".; Annu. Rev. Genet.; vol. 30; pp. 405-439 (1996).
Ganzhorn, et al.; "Kinetic Characterization of Yeast Alcohol Dehydrogenases".; The Journal of Biological Chemistry vol. 262; pp. 3,754-3,761 (1987).
Fortmann, et al. "A regulated, ubiquitin-independent degron in IkBa".; J Mol Biol.; vol. 427; pp. 2,748-2,756 (2015).
Fischer, et al.; "Catalytic properties of a bacterial acylating acetaldehyde dehydrogenase: Evidence for several active oligomeric states and coenzyme A activation upon binding".; Chemico-Biological Interactions; vol. 202; pp. 70-77 (2013).
DiCarlo, et al.; "Genome engineering in *Saccharomyces cerevisiae* using CRISPR-Cas systems".; Nucleic Acids Research; vol. 41; pp. 4,336-4,343 (2013).
Bazaes, et al.; "Comparative Kinetic Effects of Mn (II), Mg (II) and the ATP/ADP Ratio on Phosphoenolpyruvate Carboxykinases from Anaerobiospirillum succiniciproducens and *Saccharomyces cerevisiae*".; The Protein Journal vol. 26 (2007).
Bachmair, A.; Finley, D. and Varshavsky, A.; "In Vivo Half-Life of a Protein Is a Function of Its Amino-Terminal Residue".; Science; vol. 186; pp. 179-186 (1986).
Yu, et al.; "Pac-Man for biotechnology: co-opting degrons for targeted protein degradation to control and alter cell function".; Current Opinion in Biotechnology; vol. 36; pp. 199-204 (2015).
Yamanishi, et al.; "A Genome-Wide Activity Assessment of Terminator Regions in *Saccharomyces cerevisiae* Provides a 'Terminatome' Toolbox".; ACS Synthetic Biology; pp A-K.
Yagi, T.; Kagamiyama, H. and Nozaki, M.; "Aspartate: 2-Oxoglutarate Aminotransferase from Bakers' Yeast: Crystallization and Characterization"; J Biochem; vol. 92; pp. 35-43 (1982).
Wang, et al.; "Consequences of a Modified Putative Substrate-Activation Site on Catalysis by Yeast Pyruvate Decarboxylase".; Biochemistry; vol. 40; pp. 1,755-1,763 (2001).
Velculescu, et al.; "Characterization of the Yeast Transcriptome".; Cell; vol. 88; pp. 243-251 (1997).
Sagers, R., Benziman, M. and Gunsalus, I.C.; "Acetate Formation in Clostridium Acidi-Urici: Acetokinase".; vol. 82; pp. 233-238 (1961).
Ravid, Tommer and Hochstrasser, Mark; "Degradation signal diversity in the ubiquitin-proteasome system".; Nat Rev Mol Cell Biol.; vol. 9; pp. 679-690 (2008).
Peng, et al.; "Coupling gene regulatory patterns to bioprocess conditions to optimize synthetic metabolic modules for improved sesquiterpene production in yeast".; Biotechnol Biofuels; vol. 10; pp. 1-16 (2017).
Cho, Sungchan and Dreyfuss, Gideon; "A degron created by SMN2 exon 7 skipping is a principal contributor to spinal muscular atrophy severity".; Genes & Development; vol. 24; pp. 438-442 (2010).
Jan. 10, 2018 Search Report issed in International Patent Application No. PCT/EP2018/068720.

SEQUENCE LISTING

```
<160> NUMBER OF SEQ ID NOS: 134

<210> SEQ ID NO 1
<211> LENGTH: 1518
<212> TYPE: DNA
<213> ORGANISM: Saccharomyces cerevisiae
<220> FEATURE:
<223> OTHER INFORMATION: GLUCOSE-6-PHOSPHATE DEHYDROGENASE (MET19)
<220> FEATURE:
<223> OTHER INFORMATION: GLUCOSE-6-PHOSPHATE DEHYDROGENASE (MET19)

<400> SEQUENCE: 1

atgagtgaag gccccgtcaa attcgaaaaa aataccgtca tatctgtctt tggtgcgtca      60

ggtgatctgg caaagaagaa gacttttccc gccttatttg ggcttttcag agaaggttac     120

cttgatccat ctaccaagat cttcggttat gcccggtcca aattgtccat ggaggaggac     180

ctgaagtccc gtgtcctacc ccacttgaaa aaacctcacg gtgaagccga tgactctaag     240

gtcgaacagt tcttcaagat ggtcagctac atttcgggaa attacgacac agatgaaggc     300

ttcgacgaat taagaacgca gatcgagaaa ttcgagaaaa gtgccaacgt cgatgtccca     360

caccgtctct tctatctggc cttgccgcca agcgtttttt tgacggtggc caagcagatc     420

aagagtcgtg tgtacgcaga gaatggcatc acccgtgtaa tcgtagagaa acctttcggc     480

cacgacctgg cctctgccag ggagctgcaa aaaaacctgg ggcccctctt taaagaagaa     540

gagttgtaca gaattgacca ttacttgggt aaagagttgg tcaagaatct tttagtcttg     600

aggttcggta accagttttt gaatgcctcg tggaatagag acaacattca aagcgttcag     660

atttcgttta aagagaggtt cggcaccgaa ggccgtggcg gctatttcga ctctataggc     720

ataatcagag acgtgatgca gaaccatctg ttacaaatca tgactctctt gactatggaa     780

agaccggtgt cttttgaccc ggaatctatt cgtgacgaaa aggttaaggt tctaaaggcc     840

gtggccccca tcgacacgga cgacgtcctc ttgggccagt acggtaaatc tgaggacggg     900

tctaagcccg cctacgtgga tgatgacact gtagacaagg actctaaatg tgtcactttt     960

gcagcaatga ctttcaacat cgaaaacgag cgttgggagg gcgtccccat catgatgcgt    1020

gccggtaagg ctttgaatga gtccaaggtg gagatcagac tgcagtacaa agcggtcgca    1080

tcgggtgtct tcaaagacat tccaaataac gaactggtca tcagagtgca gcccgatgcc    1140

gctgtgtacc taaagtttaa tgctaagacc cctggtctgt caaatgctac ccaagtcaca    1200

gatctgaatc taacttacgc aagcaggtac caagactttt ggattccaga ggcttacgag    1260
```

```
gtgttgataa gagacgccct actgggtgac cattccaact ttgtcagaga tgacgaattg   1320

gatatcagtt ggggcatatt caccccatta ctgaagcaca tagagcgtcc ggacggtcca   1380

acaccggaaa tttaccccta cggatcaaga ggtccaaagg gattgaagga atatatgcaa   1440

aaacacaagt atgttatgcc cgaaaagcac ccttacgctt ggcccgtgac taagccagaa   1500

gatacgaagg ataattag                                                 1518


<210> SEQ ID NO 2
<211> LENGTH: 505
<212> TYPE: PRT
<213> ORGANISM: Saccharomyces cerevisiae
<220> FEATURE:
<223> OTHER INFORMATION: GLUCOSE-6-PHOSPHATE DEHYDROGENASE (MET19)
<220> FEATURE:
<223> OTHER INFORMATION: GLUCOSE-6-PHOSPHATE DEHYDROGENASE (MET19)

<400> SEQUENCE: 2

Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
                85                  90                  95

Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
        115                 120                 125

Pro Pro Ser Val Phe Leu Thr Val Ala Lys Gln Ile Lys Ser Arg Val
    130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175

Phe Lys Glu Glu Glu Leu Tyr Arg Ile Asp His Tyr Leu Gly Lys Glu
            180                 185                 190

Leu Val Lys Asn Leu Leu Val Leu Arg Phe Gly Asn Gln Phe Leu Asn
        195                 200                 205

Ala Ser Trp Asn Arg Asp Asn Ile Gln Ser Val Gln Ile Ser Phe Lys
    210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
            260                 265                 270

Glu Lys Val Lys Val Leu Lys Ala Val Ala Pro Ile Asp Thr Asp Asp
        275                 280                 285

Val Leu Leu Gly Gln Tyr Gly Lys Ser Glu Asp Gly Ser Lys Pro Ala
    290                 295                 300
```

-continued

```
Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
            340                 345                 350

Arg Leu Gln Tyr Lys Ala Val Ala Ser Gly Val Phe Lys Asp Ile Pro
        355                 360                 365

Asn Asn Glu Leu Val Ile Arg Val Gln Pro Asp Ala Ala Val Tyr Leu
    370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
        435                 440                 445

Pro Leu Leu Lys His Ile Glu Arg Pro Asp Gly Pro Thr Pro Glu Ile
    450                 455                 460

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
            500                 505
```

```
<210> SEQ ID NO 3
<211> LENGTH: 1470
<212> TYPE: DNA
<213> ORGANISM: Saccharomyces cerevisiae
<220> FEATURE:
<223> OTHER INFORMATION: 6-PHOSPHOGLUCONATE DEHYDROGENASE,
      DECARBOXYLATING 1 (GND1)
<220> FEATURE:
<223> OTHER INFORMATION: 6-PHOSPHOGLUCONATE DEHYDROGENASE,
      DECARBOXYLATING 1 (GND1)

<400> SEQUENCE: 3

atgtctgctg atttcggttt gattggtttg gccgtcatgg gtcaaaattt gatcttgaac     60

gctgctgacc acggtttcac tgtttgtgct tacaacagaa ctcaatccaa ggtcgaccat    120

ttcttggcca atgaagctaa gggcaaatct atcatcggtg ctacttccat tgaagatttc    180

atctccaaat tgaagagacc tagaaaggtc atgcttttgg ttaaagctgg tgctccagtt    240

gacgctttga tcaaccaaat cgtcccactt ttggaaaagg gtgatattat catcgatggt    300

ggtaactctc acttcccaga ttctaataga cgttacgaag aattgaagaa gaagggtatt    360

cttttcgttg gttctggtgt ctccggtggt gaggaaggtg cccgttacgg tccatctttg    420

atgccaggtg gttctgaaga agcttggcca catattaaga acatcttcca atccatctct    480

gctaaatccg acggtgaacc atgttgcgaa tgggttggcc cagccggtgc tggtcactac    540

gtcaagatgg ttcacaacgg tattgaatac ggtgatatgc aattgatttg tgaagcttat    600

gacatcatga agagattggg tgggtttacc gataaggaaa tcagtgacgt ttttgccaaa    660

tggaacaatg gtgtcttgga ttccttcttg gtcgaaatta ccagagatat tttgaaattc    720

gacgacgtcg acggtaagcc attagttgaa aaaatcatgg atactgctgg tcaaaagggt    780
```

```
actggtaagt ggactgccat caacgccttg gatttgggta tgccagttac tttgattggt    840

gaagctgtct ttgcccgttg tctatctgct ttgaagaacg agagaattag agcctccaag    900

gtcttaccag gcccagaagt tccaaaagac gccgtcaagg acagagaaca atttgtcgat    960

gatttggaac aagctttgta tgcttccaag attatttctt acgctcaagg tttcatgttg   1020

atccgtgaag ctgctgctac ttatggctgg aaactaaaca accctgccat cgctttgatg   1080

tggagaggtg gttgtatcat tagatctgtt ttcttgggtc aaatcacaaa ggcctacaga   1140

gaagaaccag atttggaaaa cttgttgttc aacaagttct tcgctgatgc cgtcaccaag   1200

gctcaatctg gttggagaaa gtcaattgcg ttggctacca cctacggtat cccaacacca   1260

gccttttcca ccgctttgtc tttctacgat gggtacagat ctgaaagatt gccagccaac   1320

ttactacaag ctcaacgtga ctactttggt gctcacactt tcagagtgtt gccagaatgt   1380

gcttctgaca acttgccagt agacaaggat atccatatca actggactgg ccacggtggt   1440

aatgtttctt cctctacata ccaagcttaa                                    1470
```

<210> SEQ ID NO 4
<211> LENGTH: 489
<212> TYPE: PRT
<213> ORGANISM: Saccharomyces cerevisiae
<220> FEATURE:
<223> OTHER INFORMATION: 6-PHOSPHOGLUCONATE DEHYDROGENASE, DECARBOXYLATING 1 (GND1)
<220> FEATURE:
<223> OTHER INFORMATION: 6-PHOSPHOGLUCONATE DEHYDROGENASE, DECARBOXYLATING 1 (GND1)

<400> SEQUENCE: 4

```
Met Ser Ala Asp Phe Gly Leu Ile Gly Leu Ala Val Met Gly Gln Asn
1               5                   10                  15

Leu Ile Leu Asn Ala Ala Asp His Gly Phe Thr Val Cys Ala Tyr Asn
            20                  25                  30

Arg Thr Gln Ser Lys Val Asp His Phe Leu Ala Asn Glu Ala Lys Gly
        35                  40                  45

Lys Ser Ile Ile Gly Ala Thr Ser Ile Glu Asp Phe Ile Ser Lys Leu
    50                  55                  60

Lys Arg Pro Arg Lys Val Met Leu Leu Val Lys Ala Gly Ala Pro Val
65                  70                  75                  80

Asp Ala Leu Ile Asn Gln Ile Val Pro Leu Leu Glu Lys Gly Asp Ile
                85                  90                  95

Ile Ile Asp Gly Gly Asn Ser His Phe Pro Asp Ser Asn Arg Arg Tyr
            100                 105                 110

Glu Glu Leu Lys Lys Lys Gly Ile Leu Phe Val Gly Ser Gly Val Ser
        115                 120                 125

Gly Gly Glu Glu Gly Ala Arg Tyr Gly Pro Ser Leu Met Pro Gly Gly
    130                 135                 140

Ser Glu Glu Ala Trp Pro His Ile Lys Asn Ile Phe Gln Ser Ile Ser
145                 150                 155                 160

Ala Lys Ser Asp Gly Glu Pro Cys Cys Glu Trp Val Gly Pro Ala Gly
                165                 170                 175

Ala Gly His Tyr Val Lys Met Val His Asn Gly Ile Glu Tyr Gly Asp
            180                 185                 190

Met Gln Leu Ile Cys Glu Ala Tyr Asp Ile Met Lys Arg Leu Gly Gly
        195                 200                 205

Phe Thr Asp Lys Glu Ile Ser Asp Val Phe Ala Lys Trp Asn Asn Gly
```

-continued

```
    210                 215                 220

Val Leu Asp Ser Phe Leu Val Glu Ile Thr Arg Asp Ile Leu Lys Phe
225                 230                 235                 240

Asp Asp Val Asp Gly Lys Pro Leu Val Glu Lys Ile Met Asp Thr Ala
                245                 250                 255

Gly Gln Lys Gly Thr Gly Lys Trp Thr Ala Ile Asn Ala Leu Asp Leu
            260                 265                 270

Gly Met Pro Val Thr Leu Ile Gly Glu Ala Val Phe Ala Arg Cys Leu
        275                 280                 285

Ser Ala Leu Lys Asn Glu Arg Ile Arg Ala Ser Lys Val Leu Pro Gly
    290                 295                 300

Pro Glu Val Pro Lys Asp Ala Val Lys Asp Arg Glu Gln Phe Val Asp
305                 310                 315                 320

Asp Leu Glu Gln Ala Leu Tyr Ala Ser Lys Ile Ile Ser Tyr Ala Gln
                325                 330                 335

Gly Phe Met Leu Ile Arg Glu Ala Ala Ala Thr Tyr Gly Trp Lys Leu
            340                 345                 350

Asn Asn Pro Ala Ile Ala Leu Met Trp Arg Gly Gly Cys Ile Ile Arg
        355                 360                 365

Ser Val Phe Leu Gly Gln Ile Thr Lys Ala Tyr Arg Glu Glu Pro Asp
    370                 375                 380

Leu Glu Asn Leu Leu Phe Asn Lys Phe Phe Ala Asp Ala Val Thr Lys
385                 390                 395                 400

Ala Gln Ser Gly Trp Arg Lys Ser Ile Ala Leu Ala Thr Thr Tyr Gly
                405                 410                 415

Ile Pro Thr Pro Ala Phe Ser Thr Ala Leu Ser Phe Tyr Asp Gly Tyr
            420                 425                 430

Arg Ser Glu Arg Leu Pro Ala Asn Leu Leu Gln Ala Gln Arg Asp Tyr
        435                 440                 445

Phe Gly Ala His Thr Phe Arg Val Leu Pro Glu Cys Ala Ser Asp Asn
    450                 455                 460

Leu Pro Val Asp Lys Asp Ile His Ile Asn Trp Thr Gly His Gly Gly
465                 470                 475                 480

Asn Val Ser Ser Ser Thr Tyr Gln Ala
                485
```

<210> SEQ ID NO 5
<211> LENGTH: 2652
<212> TYPE: DNA
<213> ORGANISM: Escherichia coli
<220> FEATURE:
<223> OTHER INFORMATION: PHOSPHOENOLPYRUVATE CARBOXYLASE (PPC/PEPC)
<220> FEATURE:
<223> OTHER INFORMATION: PHOSPHOENOLPYRUVATE CARBOXYLASE (PPC/PEPC)

<400> SEQUENCE: 5

```
atgaacgagc agtattccgc attgcgtagt aacgtgagta tgttaggaaa ggttcttggc      60

gagacgatta aggacgcgtt gggtgagcat atactagaga gagtggagac tatcagaaaa     120

ttatcaaagt caagtcgtgc cggtaatgac gccaacaggc aggagttgct taccactctt     180

caaaacctat cgaacgatga gctacttccg gtggcccgtg ccttctcgca atttttaaat     240

ctagctaata cggctgaaca atatcattct attagtccaa agggggaggc cgcctccaac     300

cctgaagtaa ttgcacgtac cttaagaaaa ttgaaaaacc aaccggagtt gtcagaggac     360

actattaaga aggctgttga aagtttatca cttgagctag tattaaccgc gcatccgact     420
```

-continued

```
gaaattacac gtaggaccct aatccacaag atggtagagg taaatgcgtg tctgaaacaa    480
ttagacaata aggatatagc agactacgaa cataaccaac ttatgcgtag attgagacag    540
ctaattgctc agtcgtggca tacggatgag attcgtaagc ttagaccttc cccagtcgac    600
gaggctaagt ggggctttgc agtcgtggag aatagtttat ggcagggtgt accaaactac    660
ttgagggaat taaatgagca attggaggaa aacctaggtt acaaattgcc agtagaattc    720
gtacccgtca ggtttacctc atggatgggg ggagacagag atggaaatcc taatgtaacc    780
gccgacatta ctcgtcatgt attgctgttg agcaggtgga aggcgaccga cctgtttctg    840
aaagacatac aagtactagt ctccgagctg agtatggtcg aggccactcc tgagttatta    900
gcgctggtgg gggaggaggg agctgctgag ccctatcgtt acctgatgaa gaacctgagg    960
agtcgtctaa tggccaccca ggcatggctg gaagctagac taaaaggaga agaattacct   1020
aagcccgaag ggctgcttac tcagaatgaa gaattgtggg aaccattgta tgcttgttac   1080
cagtcactgc aggcgtgcgg tatgggcatt atcgccaacg gcgatctgtt agacactttg   1140
agaagggtca agtgcttcgg cgtcccatta gttaggattg acataagaca ggaatccact   1200
aggcatacgg aagcgttagg ggaattgacg aggtatttag ggattggaga ttacgaatcg   1260
tggtcagaag ccgacaagca agcattcttg atccgcgaat tgaatagtaa acgtccactt   1320
ttacctagaa attggcagcc atccgcagag accagggagg tgctcgatac atgtcaagtg   1380
atagctgaag caccccaagg atcaattgct gcctacgtaa taagcatggc gaaaacccct   1440
tcagacgtat tagcagttca tcttttgctg aaagaagcgg gcattggctt cgcaatgcca   1500
gtcgctccgt tatttgaaac gctggacgat ttgaataatg caaacgacgt tatgacacag   1560
ttattaaaca tcgattggta tagaggtcta atccaaggaa agcaaatggt tatgattggt   1620
tactcggatt ctgctaaaga tgcaggggtc atggctgctt cttgggctca gtatcaagcc   1680
caagatgcct tgattaagac ttgcgaaaag gccggaatcg aattgactct atttcacggt   1740
agagggggtt ccataggtcg aggtggtgcc cctgctcacg cagctctttt atcccaacca   1800
cctggttctt taaaaggtgg ccttagggtg actgaacaag gcgaaatgat aagattcaaa   1860
tacggtttac cagaaatcac tgtgtcttcc ctttctcttt atactggtgc aattttggaa   1920
gcaaatttat tgccacctcc tgaaccaaaa gaaagctgga gaagaatcat ggatgaattg   1980
tctgttatta gctgcgatgt ttatagaggc tatgttagag aaaataaaga ttttgttcca   2040
tattttagat ctgctacacc tgaacaagaa ttgggtaaac taccattggg ttctagacca   2100
gctaaaagaa gacctactgg tggtgttgaa tcattgagag ctattccatg gatatttgct   2160
tggacacaaa acagattaat gctacctgct tggctaggtg caggtacagc tttacaaaaa   2220
gttgttgaag atggtaaaca atcagaattg gaagctatgt gtagagattg gccttttttt   2280
tctacaagat taggtatgtt agaaatggtt tttgcaaaag cagatttatg gctagctgaa   2340
tattatgatc aaagattggt tgataaagca ttgtggcctt taggtaaaga attgagaaat   2400
ttgcaagaag aagatataaa agttgtttta gcaatagcta atgattctca cttaatggct   2460
gatttaccat ggatagctga atctatccaa ttaagaaata tttatacaga tccattgaat   2520
gttttgcaag cagaattatt gcacagatct agacaagctg aaaaagaagg tcaagaacca   2580
gatccaagag ttgaacaagc attgatggtt acaattgctg gtatcgctgc aggtatgaga   2640
aatacaggtt aa                                                         2652
```

<210> SEQ ID NO 6
<211> LENGTH: 883

```
<212> TYPE: PRT
<213> ORGANISM: Escherichia coli
<220> FEATURE:
<223> OTHER INFORMATION: PHOSPHOENOLPYRUVATE CARBOXYLASE (PPC/PEPC)
<220> FEATURE:
<223> OTHER INFORMATION: PHOSPHOENOLPYRUVATE CARBOXYLASE (PPC/PEPC)

<400> SEQUENCE: 6

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
```

-continued

```
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ser Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800
```

```
Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly


<210> SEQ ID NO 7
<211> LENGTH: 1623
<212> TYPE: DNA
<213> ORGANISM: Escherichia coli
<220> FEATURE:
<223> OTHER INFORMATION: PHOSPHOENOLPYRUVATE CARBOXYKINASE (PEPCK)
<220> FEATURE:
<223> OTHER INFORMATION: PHOSPHOENOLPYRUVATE CARBOXYKINASE (PEPCK)

<400> SEQUENCE: 7

atgagagtta acaatggttt gactccacaa gaattggaag cctacggtat ttctgatgtt      60

catgatatcg tttacaaccc atcctacgac ttgttgtacc aagaagaatt agatccatct     120

ttgaccggtt acgaaagagg tgttttgact aatttgggtg ctgttgctgt tgatactggt     180

atttttactg gtagatcccc aaaggataag tacatcgtta gagatgatac caccagagat     240

actttttggt gggctgataa gggtaaaggt aagaatgata acaagccatt gtctccagaa     300

acctggcaac atttgaaagg tttggttacc agacaattga gtggtaagag attattcgtt     360

gttgatgctt tctgtggtgc taatccagat acaagattgt ccgttagatt cattactgaa     420

gttgcttggc aagcccattt cgtcaagaat atgtttatca gaccatccga tgaagaattg     480

gctggtttta agccagattt catcgttatg aatggtgcta agtgtaccaa cccacaatgg     540

aaagaacaag gtttgaacag tgaaaacttc gtcgctttca acttgaccga aagaatgcaa     600

ttgattggtg gtacttggta tggtggtgaa atgaagaaag gtatgttctc catgatgaac     660

tacttgttgc cattgaaggg tattgcttct atgcattgct ctgctaatgt tggtgaaaaa     720

ggtgatgttg ccgttttctt tggtttatct ggtactggta agactacctt gtctactgat     780

cctaagagaa gattgatcgg tgatgatgaa catggttggg atgatgatgg tgtttttaac     840

tttgaaggtg gttgttacgc caagaccatc aagttgtcta aagaagctga accagaaatc     900

tacaacgcca ttagaagaga tgctttgttg gaaaacgtta ccgttagaga agatggtact     960

atcgatttcg atgatggttc taagactgaa aacaccagag tttcttaccc aatctaccac    1020

attgataaca tcgttaagcc tgtttctaaa gctggtcatg ctaccaaggt tattttcttg    1080

actgctgatg cttttggtgt tttgccacca gtttctagat taactgctga tcaaacccaa    1140

taccacttct tgtctggttt tactgctaaa ttggcaggta ctgaaagagg tattactgaa    1200

cctactccaa ctttctctgc ttgttttggt gctgcttttt tgtcattgca tccaactcaa    1260

tacgctgaag ttttggtcaa gagaatgcaa gctgctggtg ctcaagctta tttggttaat    1320

actggttgga atggtacagg taaaagaatc tccattaagg ataccagagc cattattgat    1380

gccatcttga atggttcttt ggataacgct gaaactttca ccttgccaat gttcaatttg    1440

gctattccaa ctgaattgcc aggtgttgac accaagattt tagatccaag aaacacttac    1500
```

```
gcctctccag aacaatggca agaaaaagct gaaacattgg ccaagttgtt catcgataac   1560

ttcgacaagt atactgatac tccagctggt gctgcattgg ttgctgctgg tccaaagttg   1620

taa                                                                 1623


<210> SEQ ID NO 8
<211> LENGTH: 540
<212> TYPE: PRT
<213> ORGANISM: Escherichia coli
<220> FEATURE:
<223> OTHER INFORMATION: PHOSPHOENOLPYRUVATE CARBOXYKINASE (PEPCK)
<220> FEATURE:
<223> OTHER INFORMATION: PHOSPHOENOLPYRUVATE CARBOXYKINASE (PEPCK)

<400> SEQUENCE: 8

Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320
```

```
Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
    530                 535                 540
```

<210> SEQ ID NO 9
<211> LENGTH: 2043
<212> TYPE: DNA
<213> ORGANISM: Saccharomyces cerevisiae
<220> FEATURE:
<223> OTHER INFORMATION: TRANSKETOLASE 1 (TKL1)
<220> FEATURE:
<223> OTHER INFORMATION: TRANSKETOLASE 1 (TKL1)

<400> SEQUENCE: 9

```
atgactcaat tcactgacat tgataagcta gccgtctcca ccataagaat tttggctgtg     60

gacaccgtat ccaaggccaa ctcaggtcac ccaggtgctc cattgggtat ggcaccagct    120

gcacacgttc tatggagtca aatgcgcatg aacccaacca acccagactg gatcaacaga    180

gatagatttg tcttgtctaa cggtcacgcg gtcgctttgt tgtattctat gctacatttg    240

actggttacg atctgtctat tgaagacttg aaacagttca gacagttggg ttccagaaca    300

ccaggtcatc ctgaatttga gttgccaggt gttgaagtta ctaccggtcc attaggtcaa    360

ggtatctcca acgctgttgg tatggccatg gctcaagcta acctggctgc cacttacaac    420

aagccgggct ttaccttgtc tgacaactac acctatgttt tcttgggtga cggttgtttg    480

caagaaggta tttcttcaga agcttcctcc ttggctggtc atttgaaatt gggtaacttg    540

attgccatct acgatgacaa caagatcact atcgatggtg ctaccagtat ctcattcgat    600

gaagatgttg ctaagagata cgaagcctac ggttgggaag ttttgtacgt agaaaatggt    660

aacgaagatc tagccggtat tgccaaggct attgctcaag ctaagttatc caaggacaaa    720

ccaactttga tcaaaatgac cacaaccatt ggttacggtt ccttgcatgc cggctctcac    780
```

```
tctgtgcacg gtgccccatt gaaagcagat gatgttaaac aactaaagag caaattcggt    840

ttcaacccag acaagtcctt tgttgttcca caagaagttt acgaccacta ccaaaagaca    900

attttaaagc caggtgtcga agccaacaac aagtggaaca agttgttcag cgaataccaa    960

aagaaattcc cagaattagg tgctgaattg gctagaagat tgagcggcca actacccgca   1020

aattgggaat ctaagttgcc aacttacacc gccaaggact ctgccgtggc cactagaaaa   1080

ttatcagaaa ctgttcttga ggatgtttac aatcaattgc cagagttgat tggtggttct   1140

gccgatttaa caccttctaa cttgaccaga tggaaggaag cccttgactt ccaacctcct   1200

tcttccggtt caggtaacta ctctggtaga tacattaggt acggtattag agaacacgct   1260

atgggtgcca taatgaacgg tatttcagct ttcggtgcca actacaaacc atacggtggt   1320

actttcttga acttcgtttc ttatgctgct ggtgccgtta gattgtccgc tttgtctggc   1380

cacccagtta tttgggttgc tacacatgac tctatcggtg tcggtgaaga tggtccaaca   1440

catcaaccta ttgaaacttt agcacacttc agatccctac caaacattca agtttggaga   1500

ccagctgatg gtaacgaagt ttctgccgcc tacaagaact ctttagaatc caagcatact   1560

ccaagtatca ttgctttgtc cagacaaaac ttgccacaat tggaaggtag ctctattgaa   1620

agcgcttcta agggtggtta cgtactacaa gatgttgcta acccagatat tattttagtg   1680

gctactggtt ccgaagtgtc tttgagtgtt gaagctgcta agactttggc cgcaaagaac   1740

atcaaggctc gtgttgtttc tctaccagat ttcttcactt ttgacaaaca acccctagaa   1800

tacagactat cagtcttacc agacaacgtt ccaatcatgt ctgttgaagt tttggctacc   1860

acatgttggg gcaaatacgc tcatcaatcc ttcggtattg acagatttgg tgcctccggt   1920

aaggcaccag aagtcttcaa gttcttcggt ttcaccccag aaggtgttgc tgaaagagct   1980

caaaagacca ttgcattcta taagggtgac aagctaattt ctcctttgaa aaaagctttc   2040

taa                                                                 2043
```

<210> SEQ ID NO 10
<211> LENGTH: 680
<212> TYPE: PRT
<213> ORGANISM: Saccharomyces cerevisiae
<220> FEATURE:
<223> OTHER INFORMATION: TRANSKETOLASE 1 (TKL1)
<220> FEATURE:
<223> OTHER INFORMATION: TRANSKETOLASE 1 (TKL1)

<400> SEQUENCE: 10

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
```

-continued

```
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540
```

```
Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680
```

<210> SEQ ID NO 11
<211> LENGTH: 1008
<212> TYPE: DNA
<213> ORGANISM: Saccharomyces cerevisiae
<220> FEATURE:
<223> OTHER INFORMATION: TRANSALDOLASE 1 (TAL1)
<220> FEATURE:
<223> OTHER INFORMATION: TRANSALDOLASE 1 (TAL1)

<400> SEQUENCE: 11

```
atgtctgaac cagctcaaaa gaaacaaaag gttgctaaca actctctaga acaattgaaa     60

gcctccggca ctgtcgttgt tgccgacact ggtgatttcg gctctattgc caagtttcaa    120

cctcaagact ccacaactaa cccatcattg atcttggctg ctgccaagca accaacttac    180

gccaagttga tcgatgttgc cgtggaatac ggtaagaagc atggtaagac caccgaagaa    240

caagtcgaaa atgctgtgga cagattgtta gtcgaattcg gtaaggagat cttaaagatt    300

gttccaggca gagtctccac cgaagttgat gctagattgt cttttgacac tcaagctacc    360

attgaaaagg ctagacatat cattaaattg tttgaacaag aaggtgtctc caaggaaaga    420

gtccttatta aaattgcttc cacttgggaa ggtattcaag ctgccaaaga attggaagaa    480

aaggacggta tccactgtaa tttgactcta ttattctcct tcgttcaagc agttgcctgt    540

gccgaggccc aagttacttt gatttcccca tttgttggta gaattctaga ctggtacaaa    600

tccagcactg gtaaagatta caagggtgaa gccgacccag gtgttatttc cgtcaagaaa    660

atctacaact actacaagaa gtacggttac aagactattg ttatgggtgc ttctttcaga    720

agcactgacg aaatcaaaaa cttggctggt gttgactatc taacaatttc tccagcttta    780

ttggacaagt tgatgaacag tactgaacct ttcccaagag ttttggaccc tgtctccgct    840

aagaaggaag ccggcgacaa gatttcttac atcagcgacg aatctaaatt cagattcgac    900

ttgaatgaag acgctatggc cactgaaaaa ttgtccgaag gtatcagaaa attctctgcc    960

gatattgtta ctctattcga cttgattgaa aagaaagtta ccgcttaa                1008
```

<210> SEQ ID NO 12
<211> LENGTH: 335
<212> TYPE: PRT
<213> ORGANISM: Saccharomyces cerevisiae
<220> FEATURE:
<223> OTHER INFORMATION: TRANSALDOLASE 1 (TAL1)
<220> FEATURE:
<223> OTHER INFORMATION: TRANSALDOLASE 1 (TAL1)

<400> SEQUENCE: 12

```
Met Ser Glu Pro Ala Gln Lys Lys Gln Lys Val Ala Asn Asn Ser Leu
1               5                   10                  15

Glu Gln Leu Lys Ala Ser Gly Thr Val Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Asp
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335
```

<210> SEQ ID NO 13
<211> LENGTH: 1503
<212> TYPE: DNA
<213> ORGANISM: Saccharomyces cerevisiae
<220> FEATURE:
<223> OTHER INFORMATION: PYRUVATE KINASE 1 (PYK1)
<220> FEATURE:
<223> OTHER INFORMATION: PYRUVATE KINASE 1 (PYK1)

<400> SEQUENCE: 13

```
atgtctagat tagaaagatt gacctcatta aacgttgttg ctggttctga cttgagaaga      60
acctccatca ttggtaccat cggtccaaag accaacaacc cagaaacctt ggttgctttg     120
agaaaggctg gtttgaacat tgtccgtatg aacttctctc acggttctta cgaataccac     180
aagtctgtca ttgacaacgc cagaaagtcc gaagaattgt acccaggtag accattggcc     240
attgctttgg acaccaaggg tccagaaatc agaactggta ccaccaccaa cgatgttgac     300
tacccaatcc caccaaacca cgaaatgatc ttcaccaccg atgacaagta cgctaaggct     360
tgtgacgaca agatcatgta cgttgactac aagaacatca ccaaggtcat ctccgctggt     420
agaatcatct acgttgatga tggtgttttg tctttccaag ttttggaagt cgttgacgac     480
aagactttga aggtcaaggc tttgaacgcc ggtaagatct gttcccacaa gggtgtcaac     540
ttaccaggta ccgatgtcga tttgccagct ttgtctgaaa aggacaagga agatttgaga     600
ttcggtgtca agaacggtgt ccacatggtc ttcgcttctt tcatcagaac cgccaacgat     660
gttttgacca tcagagaagt cttgggtgaa caaggtaagg acgtcaagat cattgtcaag     720
attgaaaacc aacaaggtgt taacaacttc gacgaaatct tgaaggtcac tgacggtgtt     780
atggttgcca gaggtgactt gggtattgaa atcccagccc cagaagtctt ggctgtccaa     840
aagaaattga ttgctaagtc taacttggct ggtaagccag ttatctgtgc tacccaaatg     900
ttggaatcca tgacttacaa cccaagacca accagagctg aagtttccga tgtcggtaac     960
gctatcttgg atggtgctga ctgtgttatg ttgtctggtg aaaccgccaa gggtaactac    1020
ccaatcaacg ccgttaccac tatggctgaa accgctgtca ttgctgaaca agctatcgct    1080
tacttgccaa actacgatga catgagaaac tgtactccaa agccaacctc caccaccgaa    1140
accgtcgctg cctccgctgt cgctgctgtt ttcgaacaaa aggccaaggc tatcattgtc    1200
ttgtccactt ccggtaccac cccaagattg gtttccaagt acagaccaaa ctgtccaatc    1260
atcttggtta ccagatgccc aagagctgct agattctctc acttgtacag aggtgtcttc    1320
ccattcgttt tcgaaaagga acctgtctct gactggactg atgatgttga agcccgtatc    1380
aacttcggta ttgaaaaggc taaggaattc ggtatcttga agaagggtga cacttacgtt    1440
tccatccaag gtttcaaggc cggtgctggt cactccaaca ctttgcaagt ctctaccgtt    1500
taa                                                                  1503
```

<210> SEQ ID NO 14
<211> LENGTH: 500
<212> TYPE: PRT
<213> ORGANISM: Saccharomyces cerevisiae
<220> FEATURE:
<223> OTHER INFORMATION: PYRUVATE KINASE 1 (PYK1)
<220> FEATURE:
<223> OTHER INFORMATION: PYRUVATE KINASE 1 (PYK1)

<400> SEQUENCE: 14

```
Met Ser Arg Leu Glu Arg Leu Thr Ser Leu Asn Val Val Ala Gly Ser
1               5                   10                  15

Asp Leu Arg Arg Thr Ser Ile Ile Gly Thr Ile Gly Pro Lys Thr Asn
            20                  25                  30

Asn Pro Glu Thr Leu Val Ala Leu Arg Lys Ala Gly Leu Asn Ile Val
        35                  40                  45

Arg Met Asn Phe Ser His Gly Ser Tyr Glu Tyr His Lys Ser Val Ile
    50                  55                  60
```

-continued

```
Asp Asn Ala Arg Lys Ser Glu Glu Leu Tyr Pro Gly Arg Pro Leu Ala
65                  70                  75                  80

Ile Ala Leu Asp Thr Lys Gly Pro Glu Ile Arg Thr Gly Thr Thr Thr
                85                  90                  95

Asn Asp Val Asp Tyr Pro Ile Pro Pro Asn His Glu Met Ile Phe Thr
            100                 105                 110

Thr Asp Asp Lys Tyr Ala Lys Ala Cys Asp Asp Lys Ile Met Tyr Val
        115                 120                 125

Asp Tyr Lys Asn Ile Thr Lys Val Ile Ser Ala Gly Arg Ile Ile Tyr
    130                 135                 140

Val Asp Asp Gly Val Leu Ser Phe Gln Val Leu Glu Val Val Asp Asp
145                 150                 155                 160

Lys Thr Leu Lys Val Lys Ala Leu Asn Ala Gly Lys Ile Cys Ser His
                165                 170                 175

Lys Gly Val Asn Leu Pro Gly Thr Asp Val Asp Leu Pro Ala Leu Ser
            180                 185                 190

Glu Lys Asp Lys Glu Asp Leu Arg Phe Gly Val Lys Asn Gly Val His
        195                 200                 205

Met Val Phe Ala Ser Phe Ile Arg Thr Ala Asn Asp Val Leu Thr Ile
    210                 215                 220

Arg Glu Val Leu Gly Glu Gln Gly Lys Asp Val Lys Ile Ile Val Lys
225                 230                 235                 240

Ile Glu Asn Gln Gln Gly Val Asn Asn Phe Asp Glu Ile Leu Lys Val
                245                 250                 255

Thr Asp Gly Val Met Val Ala Arg Gly Asp Leu Gly Ile Glu Ile Pro
            260                 265                 270

Ala Pro Glu Val Leu Ala Val Gln Lys Lys Leu Ile Ala Lys Ser Asn
        275                 280                 285

Leu Ala Gly Lys Pro Val Ile Cys Ala Thr Gln Met Leu Glu Ser Met
    290                 295                 300

Thr Tyr Asn Pro Arg Pro Thr Arg Ala Glu Val Ser Asp Val Gly Asn
305                 310                 315                 320

Ala Ile Leu Asp Gly Ala Asp Cys Val Met Leu Ser Gly Glu Thr Ala
                325                 330                 335

Lys Gly Asn Tyr Pro Ile Asn Ala Val Thr Thr Met Ala Glu Thr Ala
            340                 345                 350

Val Ile Ala Glu Gln Ala Ile Ala Tyr Leu Pro Asn Tyr Asp Asp Met
        355                 360                 365

Arg Asn Cys Thr Pro Lys Pro Thr Ser Thr Thr Glu Thr Val Ala Ala
    370                 375                 380

Ser Ala Val Ala Ala Val Phe Glu Gln Lys Ala Lys Ala Ile Ile Val
385                 390                 395                 400

Leu Ser Thr Ser Gly Thr Thr Pro Arg Leu Val Ser Lys Tyr Arg Pro
                405                 410                 415

Asn Cys Pro Ile Ile Leu Val Thr Arg Cys Pro Arg Ala Ala Arg Phe
            420                 425                 430

Ser His Leu Tyr Arg Gly Val Phe Pro Phe Val Phe Glu Lys Glu Pro
        435                 440                 445

Val Ser Asp Trp Thr Asp Asp Val Glu Ala Arg Ile Asn Phe Gly Ile
    450                 455                 460

Glu Lys Ala Lys Glu Phe Gly Ile Leu Lys Lys Gly Asp Thr Tyr Val
465                 470                 475                 480

Ser Ile Gln Gly Phe Lys Ala Gly Ala Gly His Ser Asn Thr Leu Gln
```

```
            485                 490                 495

Val Ser Thr Val
            500


<210> SEQ ID NO 15
<211> LENGTH: 1521
<212> TYPE: DNA
<213> ORGANISM: Saccharomyces cerevisiae
<220> FEATURE:
<223> OTHER INFORMATION: PYRUVATE KINASE 2 (PYK2)
<220> FEATURE:
<223> OTHER INFORMATION: PYRUVATE KINASE 2 (PYK2)

<400> SEQUENCE: 15

atgccagagt ccagattgca gagactagct aatttgaaaa taggaactcc gcagcagctc      60

agacgcacct ccataatagg taccattggg cccaagacaa atagctgcga ggccattact     120

gctctgagaa aagctggttt gaacatcatt cgattgaact tttcccatgg ctcctacgaa     180

ttccatcaat cagtaatcga aaatgctgtg aaatcggaac agcaattccc tggcaggccg     240

ctcgccattg ccctggatac caagggtccc gagatcagaa caggtcgcac gttaaatgac     300

caagatcttt atatccccgt agaccaccaa atgatcttta ccactgacgc aagttttgca     360

aacacctcca atgataaaat catgtatata gactatgcta acctgacaaa agttatcgtt     420

ccggggagat ttatatacgt ggacgacggg attctctctt ttaaagtgct ccaaatcatt     480

gacgaatcta atttaagggt gcaagcggta aactcgggtt atatcgcatc tcataaaggt     540

gttaatctgc ctaataccga cgttgatttg ccccccttgt ccgccaaaga catgaaggac     600

ttgcaattcg gagtccgcaa tggcattcac atcgtatttg cctctttcat aagaacttca     660

gaagatgtgt tgtctatcag aaaagcgttg ggttctgaag ggcaagatat caagattata     720

tccaagatag aaaaccagca agggttggat aattttgacg aaatcctgga agtcacggat     780

ggtgttatga tagcgagagg cgatttagga attgaaatcc tggcacctga agtattagcc     840

attcaaaaaa agctgattgc aaaatgtaat ttggcgggca aacctgtcat ttgcgcgact     900

cagatgctgg attcaatgac acacaatccg agaccgacaa gggctgaagt atcggatgtg     960

ggtaacgctg tgttggatgg tgctgattgt gttatgcttt ctggagaaac ggcgaagggt    1020

gattatccgg tgaatgcagt taatattatg gcggcgaccg ctctgattgc tgaaagtact    1080

atcgctcatt tggctcttta tgacgatctc agagacgcca ctcccaaacc tacttccact    1140

acggaaactg tagcagctgc agctaccgca gcaatcttgg agcaagatgg taaggccatc    1200

gttgtattat ctactacagg gaacacggca aggctactgt cgaagtatag accaagctgc    1260

cctatcatat tagtaacaag acacgcaaga acggcaagaa ttgcgcattt gtatagaggt    1320

gttttcccat ttctgtatga accgaaacgc ctagacgact ggggtgagga tgttcatagg    1380

cgcctaaagt ttggtgttga aatggcgagg tctttcggaa tggtggacaa cggtgatact    1440

gttgtttcca ttcaaggatt caaaggagga gtcggccatt ccaatacctt acgcatttct    1500

actgttggtc aagaattcta g                                              1521


<210> SEQ ID NO 16
<211> LENGTH: 506
<212> TYPE: PRT
<213> ORGANISM: Saccharomyces cerevisiae
<220> FEATURE:
<223> OTHER INFORMATION: PYRUVATE KINASE 2 (PYK2)
<220> FEATURE:
<223> OTHER INFORMATION: PYRUVATE KINASE 2 (PYK2)
```

<400> SEQUENCE: 16

```
Met Pro Glu Ser Arg Leu Gln Arg Leu Ala Asn Leu Lys Ile Gly Thr
1               5                   10                  15

Pro Gln Gln Leu Arg Arg Thr Ser Ile Ile Gly Thr Ile Gly Pro Lys
            20                  25                  30

Thr Asn Ser Cys Glu Ala Ile Thr Ala Leu Arg Lys Ala Gly Leu Asn
        35                  40                  45

Ile Ile Arg Leu Asn Phe Ser His Gly Ser Tyr Glu Phe His Gln Ser
    50                  55                  60

Val Ile Glu Asn Ala Val Lys Ser Glu Gln Gln Phe Pro Gly Arg Pro
65                  70                  75                  80

Leu Ala Ile Ala Leu Asp Thr Lys Gly Pro Glu Ile Arg Thr Gly Arg
                85                  90                  95

Thr Leu Asn Asp Gln Asp Leu Tyr Ile Pro Val Asp His Gln Met Ile
            100                 105                 110

Phe Thr Thr Asp Ala Ser Phe Ala Asn Thr Ser Asn Asp Lys Ile Met
        115                 120                 125

Tyr Ile Asp Tyr Ala Asn Leu Thr Lys Val Ile Val Pro Gly Arg Phe
    130                 135                 140

Ile Tyr Val Asp Asp Gly Ile Leu Ser Phe Lys Val Leu Gln Ile Ile
145                 150                 155                 160

Asp Glu Ser Asn Leu Arg Val Gln Ala Val Asn Ser Gly Tyr Ile Ala
                165                 170                 175

Ser His Lys Gly Val Asn Leu Pro Asn Thr Asp Val Asp Leu Pro Pro
            180                 185                 190

Leu Ser Ala Lys Asp Met Lys Asp Leu Gln Phe Gly Val Arg Asn Gly
        195                 200                 205

Ile His Ile Val Phe Ala Ser Phe Ile Arg Thr Ser Glu Asp Val Leu
    210                 215                 220

Ser Ile Arg Lys Ala Leu Gly Ser Glu Gly Gln Asp Ile Lys Ile Ile
225                 230                 235                 240

Ser Lys Ile Glu Asn Gln Gln Gly Leu Asp Asn Phe Asp Glu Ile Leu
                245                 250                 255

Glu Val Thr Asp Gly Val Met Ile Ala Arg Gly Asp Leu Gly Ile Glu
            260                 265                 270

Ile Leu Ala Pro Glu Val Leu Ala Ile Gln Lys Lys Leu Ile Ala Lys
        275                 280                 285

Cys Asn Leu Ala Gly Lys Pro Val Ile Cys Ala Thr Gln Met Leu Asp
    290                 295                 300

Ser Met Thr His Asn Pro Arg Pro Thr Arg Ala Glu Val Ser Asp Val
305                 310                 315                 320

Gly Asn Ala Val Leu Asp Gly Ala Asp Cys Val Met Leu Ser Gly Glu
                325                 330                 335

Thr Ala Lys Gly Asp Tyr Pro Val Asn Ala Val Asn Ile Met Ala Ala
            340                 345                 350

Thr Ala Leu Ile Ala Glu Ser Thr Ile Ala His Leu Ala Leu Tyr Asp
        355                 360                 365

Asp Leu Arg Asp Ala Thr Pro Lys Pro Thr Ser Thr Thr Glu Thr Val
    370                 375                 380

Ala Ala Ala Ala Thr Ala Ala Ile Leu Glu Gln Asp Gly Lys Ala Ile
385                 390                 395                 400

Val Val Leu Ser Thr Thr Gly Asn Thr Ala Arg Leu Leu Ser Lys Tyr
                405                 410                 415
```

-continued

```
Arg Pro Ser Cys Pro Ile Ile Leu Val Thr Arg His Ala Arg Thr Ala
            420                 425                 430

Arg Ile Ala His Leu Tyr Arg Gly Val Phe Pro Phe Leu Tyr Glu Pro
        435                 440                 445

Lys Arg Leu Asp Asp Trp Gly Glu Asp Val His Arg Arg Leu Lys Phe
    450                 455                 460

Gly Val Glu Met Ala Arg Ser Phe Gly Met Val Asp Asn Gly Asp Thr
465                 470                 475                 480

Val Val Ser Ile Gln Gly Phe Lys Gly Gly Val Gly His Ser Asn Thr
                485                 490                 495

Leu Arg Ile Ser Thr Val Gly Gln Glu Phe
            500                 505
```

<210> SEQ ID NO 17
<211> LENGTH: 1692
<212> TYPE: DNA
<213> ORGANISM: Saccharomyces cerevisiae
<220> FEATURE:
<223> OTHER INFORMATION: PYRUVATE DECARBOXYLASE ISOZYME 1 (PDC1)
<220> FEATURE:
<223> OTHER INFORMATION: PYRUVATE DECARBOXYLASE ISOZYME 1 (PDC1)

<400> SEQUENCE: 17

```
atgtctgaaa ttactttggg taaatatttg ttcgaaagat taaagcaagt caacgttaac     60

accgttttcg gtttgccagg tgacttcaac ttgtccttgt tggacaagat ctacgaagtt    120

gaaggtatga gatgggctgg taacgccaac gaattgaacg ctgcttacgc cgctgatggt    180

tacgctcgta tcaagggtat gtcttgtatc atcaccacct tcggtgtcgg tgaattgtct    240

gctttgaacg gtattgccgg ttcttacgct gaacacgtcg gtgttttgca cgttgttggt    300

gtcccatcca tctctgctca agctaagcaa ttgttgttgc accacacctt gggtaacggt    360

gacttcactg ttttccacag aatgtctgcc aacatttctg aaaccactgc tatgatcact    420

gacattgcta ccgccccagc tgaaattgac agatgtatca gaaccactta cgtcacccaa    480

agaccagtct acttaggttt gccagctaac ttggtcgact tgaacgtccc agctaagttg    540

ttgcaaactc caattgacat gtctttgaag ccaaacgatg ctgaatccga aaaggaagtc    600

attgacacca tcttggcttt ggtcaaggat gctaagaacc cagttatctt ggctgatgct    660

tgttgttcca gacacgacgt caaggctgaa actaagaagt tgattgactt gactcaattc    720

ccagctttcg tcaccccaat gggtaagggt tccattgacg aacaacaccc aagatacggt    780

ggtgtttacg tcggtacctt gtccaagcca gaagttaagg aagccgttga atctgctgac    840

ttgattttgt ctgtcggtgc tttgttgtct gatttcaaca ccggttcttt ctcttactct    900

tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080

gcttctaccc cattgaagca agaatggatg tggaaccaat tgggtaactt cttgcaagaa   1140

ggtgatgttg tcattgctga aaccggtacc tccgctttcg gtatcaacca aaccactttc   1200

ccaaacaaca cctacggtat ctctcaagtc ttatggggtt ccattggttt caccactggt   1260

gctaccttgg gtgctgcttt cgctgctgaa gaaattgatc caaagaagag agttatctta   1320

ttcattggtg acggttcttt gcaattgact gttcaagaaa tctccaccat gatcagatgg   1380

ggcttgaagc catacttgtt cgtcttgaac aacgatggtt acaccattga aaagttgatt   1440
```

-continued

```
cacggtccaa aggctcaata caacgaaatt caaggttggg accacctatc cttgttgcca   1500

actttcggtg ctaaggacta tgaaacccac agagtcgcta ccaccggtga atgggacaag   1560

ttgacccaag acaagtcttt caacgacaac tctaagatca gaatgattga aatcatgttg   1620

ccagtcttcg atgctccaca aaacttggtt gaacaagcta agttgactgc tgctaccaac   1680

gctaagcaat aa                                                       1692


<210> SEQ ID NO 18
<211> LENGTH: 563
<212> TYPE: PRT
<213> ORGANISM: Saccharomyces cerevisiae
<220> FEATURE:
<223> OTHER INFORMATION: PYRUVATE DECARBOXYLASE ISOZYME 1 (PDC1)
<220> FEATURE:
<223> OTHER INFORMATION: PYRUVATE DECARBOXYLASE ISOZYME 1 (PDC1)

<400> SEQUENCE: 18

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300
```

```
Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 19
<211> LENGTH: 1692
<212> TYPE: DNA
<213> ORGANISM: Saccharomyces cerevisiae
<220> FEATURE:
<223> OTHER INFORMATION: PYRUVATE DECARBOXYLASE ISOZYME 3 (PDC6)
<220> FEATURE:
<223> OTHER INFORMATION: PYRUVATE DECARBOXYLASE ISOZYME 3 (PDC6)

<400> SEQUENCE: 19

```
atgtctgaaa ttactcttgg aaaatactta tttgaaagat tgaagcaagt taatgttaac     60

accatttttg ggctaccagg cgacttcaac ttgtccctat tggacaagat ttacgaggta    120

gatggattga gatgggctgg taatgcaaat gagctgaacg ccgcctatgc cgccgatggt    180

tacgcacgca tcaagggttt atctgtgctg gtaactactt ttggcgtagg tgaattatcc    240

gccttgaatg gtattgcagg atcgtatgca gaacacgtcg gtgtactgca tgttgttggt    300

gtcccctcta tctccgctca ggctaagcaa ttgttgttgc atcatacctt gggtaacggt    360

gattttaccg tttttcacag aatgtccgcc aatatctcag aaactacatc aatgattaca    420

gacattgcta cagccccttc agaaatcgat aggttgatca ggacaacatt tataacacaa    480

aggcctagct acttggggtt gccagcgaat ttggtagatc taaaggttcc tggttctctt    540
```

```
ttggaaaaac cgattgatct atcattaaaa cctaacgatc ccgaagctga aaaggaagtt    600

attgataccg tactagaatt gatccagaat tcgaaaaacc ctgttatact atcggatgcc    660

tgtgcttcta ggcacaacgt taaaaaagaa acccagaagt taattgattt gacgcaattc    720

ccagcttttg tgacacctct aggtaaaggg tcaatagatg aacagcatcc cagatatggc    780

ggtgtttatg tgggaacgct gtccaaacaa gacgtgaaac aggccgttga gtcggctgat    840

ttgatccttt cggtcggtgc tttgctctct gattttaaca caggttcgtt ttcctactcc    900

tacaagacta aaaatgtagt ggagtttcat tccgattacg taaaggtgaa gaacgctacg    960

ttcctcggtg tacaaatgaa atttgcacta caaaacttac tgaaggttat tcccgatgtt   1020

gttaagggct acaagagcgt tcccgtacca accaaaactc ccgcaaacaa aggtgtacct   1080

gctagcacgc ccttgaaaca agagtggttg tggaacgaat tgtccaaatt cttgcaagaa   1140

ggtgatgtta tcatttccga gaccggcacg tctgccttcg gtatcaatca aactatcttt   1200

cctaaggacg cctacggtat ctcgcaggtg ttgtgggggt ccatcggttt tacaacagga   1260

gcaactttag gtgctgcctt tgccgctgag gagattgacc ccaacaagag agtcatctta   1320

ttcataggtg acgggtcttt gcagttaacc gtccaagaaa tctccaccat gatcagatgg   1380

gggttaaagc cgtatctttt tgtccttaac aacgacggct acactatcga aaagctgatt   1440

catgggcctc acgcagagta caacgaaatc cagacctggg atcacctcgc cctgttgccc   1500

gcatttggtg cgaaaaagta cgaaaatcac aagatcgcca ctacgggtga gtgggatgcc   1560

ttaaccactg attcagagtt ccagaaaaac tcggtgatca gactaattga actgaaactg   1620

cccgtctttg atgctccgga aagtttgatc aaacaagcgc aattgactgc cgctacaaat   1680

gccaaacaat aa                                                       1692


<210> SEQ ID NO 20
<211> LENGTH: 563
<212> TYPE: PRT
<213> ORGANISM: Saccharomyces cerevisiae
<220> FEATURE:
<223> OTHER INFORMATION: PYRUVATE DECARBOXYLASE ISOZYME 3 (PDC6)
<220> FEATURE:
<223> OTHER INFORMATION: PYRUVATE DECARBOXYLASE ISOZYME 3 (PDC6)

<400> SEQUENCE: 20

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140
```

-continued

```
Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560
```

Ala Lys Gln

<210> SEQ ID NO 21
<211> LENGTH: 1692
<212> TYPE: DNA
<213> ORGANISM: Saccharomyces cerevisiae
<220> FEATURE:
<223> OTHER INFORMATION: PYRUVATE DECARBOXYLASE ISOZYME 2 (PDC5)
<220> FEATURE:
<223> OTHER INFORMATION: PYRUVATE DECARBOXYLASE ISOZYME 2 (PDC5)

<400> SEQUENCE: 21
atgtctgaaa taaccttagg taaatattta tttgaaagat tgagccaagt caactgtaac 60
accgtcttcg gtttgccagg tgactttaac ttgtctcttt tggataagct ttatgaagtc 120
aaaggtatga gatgggctgg taacgctaac gaattgaacg ctgcctatgc tgctgatggt 180
tacgctcgta tcaagggtat gtcctgtatt attaccacct tcggtgttgg tgaattgtct 240
gctttgaatg gtattgccgg ttcttacgct gaacatgtcg gtgttttgca cgttgttggt 300
gttccatcca tctcttctca agctaagcaa ttgttgttgc atcatacctt gggtaacggt 360
gacttcactg ttttccacag aatgtctgcc aacatttctg aaaccactgc catgatcact 420
gatattgcta acgctccagc tgaaattgac agatgtatca gaaccaccta cactacccaa 480
agaccagtct acttgggttt gccagctaac ttggttgact tgaacgtccc agccaagtta 540
ttggaaactc caattgactt gtctttgaag ccaaacgacg ctgaagctga agctgaagtt 600
gttagaactg ttgttgaatt gatcaaggat gctaagaacc cagttatctt ggctgatgct 660
tgtgcttcta gacatgatgt caaggctgaa actaagaagt tgatggactt gactcaattc 720
ccagtttacg tcaccccaat gggtaagggt gctattgacg aacaacaccc aagatacggt 780
ggtgtttacg ttggtacctt gtctagacca gaagttaaga aggctgtaga atctgctgat 840
ttgatattgt ctatcggtgc tttgttgtct gatttcaata ccggttcttt ctcttactcc 900
tacaagacca aaaatatcgt tgaattccac tctgaccaca tcaagatcag aaacgccacc 960
ttcccaggtg ttcaaatgaa atttgccttg caaaaattgt tggatgctat tccagaagtc 1020
gtcaaggact acaaacctgt tgctgtccca gctagagttc caattaccaa gtctactcca 1080
gctaacactc caatgaagca agaatggatg tggaaccatt tgggtaactt cttgagagaa 1140
ggtgatattg ttattgctga aaccggtact tccgccttcg gtattaacca aactactttc 1200
ccaacagatg tatacgctat cgtccaagtc ttgtggggtt ccattggttt cacagtcggc 1260
gctctattgg gtgctactat ggccgctgaa gaacttgatc caaagaagag agttatttta 1320
ttcattggtg acggttctct acaattgact gttcaagaaa tctctaccat gattagatgg 1380
ggtttgaagc catacatttt tgtcttgaat aacaacggtt acaccattga aaaattgatt 1440
cacggtcctc atgccgaata taatgaaatt caaggttggg accacttggc cttattgcca 1500
acttttggtg ctagaaacta cgaaacccac agagttgcta ccactggtga atgggaaaag 1560
ttgactcaag acaaggactt ccaagacaac tctaagatta gaatgattga agttatgttg 1620
ccagtctttg atgctccaca aaacttggtt aaacaagctc aattgactgc cgctactaac 1680
gctaaacaat aa 1692

<210> SEQ ID NO 22
<211> LENGTH: 563
<212> TYPE: PRT
<213> ORGANISM: Saccharomyces cerevisiae
<220> FEATURE:
<223> OTHER INFORMATION: PYRUVATE DECARBOXYLASE ISOZYME 2 (PDC5)

<220> FEATURE:
<223> OTHER INFORMATION: PYRUVATE DECARBOXYLASE ISOZYME 2 (PDC5)

<400> SEQUENCE: 22

```
Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn His Leu Gly Asn Phe Leu Arg Glu Gly Asp Ile Val
    370                 375                 380

Ile Ala Glu Thr Gly Thr Ser Ala Phe Gly Ile Asn Gln Thr Thr Phe
385                 390                 395                 400
```

-continued

Pro Thr Asp Val Tyr Ala Ile Val Gln Val Leu Trp Gly Ser Ile Gly
405 410 415

Phe Thr Val Gly Ala Leu Leu Gly Ala Thr Met Ala Ala Glu Glu Leu
420 425 430

Asp Pro Lys Lys Arg Val Ile Leu Phe Ile Gly Asp Gly Ser Leu Gln
435 440 445

Leu Thr Val Gln Glu Ile Ser Thr Met Ile Arg Trp Gly Leu Lys Pro
450 455 460

Tyr Ile Phe Val Leu Asn Asn Asn Gly Tyr Thr Ile Glu Lys Leu Ile
465 470 475 480

His Gly Pro His Ala Glu Tyr Asn Glu Ile Gln Gly Trp Asp His Leu
485 490 495

Ala Leu Leu Pro Thr Phe Gly Ala Arg Asn Tyr Glu Thr His Arg Val
500 505 510

Ala Thr Thr Gly Glu Trp Glu Lys Leu Thr Gln Asp Lys Asp Phe Gln
515 520 525

Asp Asn Ser Lys Ile Arg Met Ile Glu Val Met Leu Pro Val Phe Asp
530 535 540

Ala Pro Gln Asn Leu Val Lys Gln Ala Gln Leu Thr Ala Ala Thr Asn
545 550 555 560

Ala Lys Gln

<210> SEQ ID NO 23
<211> LENGTH: 1047
<212> TYPE: DNA
<213> ORGANISM: Saccharomyces cerevisiae
<220> FEATURE:
<223> OTHER INFORMATION: ALCOHOL DEHYDROGENASE 1 (ADH1)
<220> FEATURE:
<223> OTHER INFORMATION: ALCOHOL DEHYDROGENASE 1 (ADH1)

<400> SEQUENCE: 23
atgtctatcc cagaaactca aaaaggtgtt atcttctacg aatcccacgg taagttggaa 60
tacaaagata ttccagttcc aaagccaaag gccaacgaat tgttgatcaa cgttaaatac 120
tctggtgtct gtcacactga cttgcacgct tggcacggtg actggccatt gccagttaag 180
ctaccattag tcggtggtca cgaaggtgcc ggtgtcgttg tcggcatggg tgaaaacgtt 240
aagggctgga agatcggtga ctacgccggt atcaaatggt tgaacggttc ttgtatggcc 300
tgtgaatact gtgaattggg taacgaatcc aactgtcctc acgctgactt gtctggttac 360
acccacgacg gttctttcca acaatacgct accgctgacg ctgttcaagc cgctcacatt 420
cctcaaggta ccgacttggc ccaagtcgcc cccatcttgt gtgctggtat caccgtctac 480
aaggctttga agtctgctaa cttgatggcc ggtcactggg ttgctatctc cggtgctgct 540
ggtggtctag gttctttggc tgttcaatac gccaaggcta tgggttacag agtcttgggt 600
attgacggtg gtgaaggtaa ggaagaatta ttcagatcca tcggtggtga agtcttcatt 660
gacttcacta aggaaaagga cattgtcggt gctgttctaa aggccactga cggtggtgct 720
cacggtgtca tcaacgtttc cgtttccgaa gccgctattg aagcttctac cagatacgtt 780
agagctaacg gtaccaccgt tttggtcggt atgccagctg gtgccaagtg ttgttctgat 840
gtcttcaacc aagtcgtcaa gtccatctct attgttggtt cttacgtcgg taacagagct 900
gacaccagag aagctttgga cttcttcgcc agaggtttgg tcaagtctcc aatcaaggtt 960
gtcggcttgt ctaccttgcc agaaatttac gaaaagatgg aaaagggtca aatcgttggt 1020

```
agatacgttg ttgacacttc taaataa                                         1047


<210> SEQ ID NO 24
<211> LENGTH: 348
<212> TYPE: PRT
<213> ORGANISM: Saccharomyces cerevisiae
<220> FEATURE:
<223> OTHER INFORMATION: ALCOHOL DEHYDROGENASE 1 (ADH1)
<220> FEATURE:
<223> OTHER INFORMATION: ALCOHOL DEHYDROGENASE 1 (ADH1)

<400> SEQUENCE: 24

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 25
<211> LENGTH: 1128
<212> TYPE: DNA
<213> ORGANISM: Saccharomyces cerevisiae
<220> FEATURE:
<223> OTHER INFORMATION: ALCOHOL DEHYDROGENASE 3 (ADH3)
<220> FEATURE:
<223> OTHER INFORMATION: ALCOHOL DEHYDROGENASE 3 (ADH3)

<400> SEQUENCE: 25

```
atgttgagaa cgtcaacatt gttcaccagg cgtgtccaac caagcctatt ttctagaaac     60

attcttagat tgcaatccac agctgcaatc cctaagactc aaaaaggtgt catcttttat    120

gagaataagg ggaagctgca ttacaaagat atccctgtcc ccgagcctaa gccaaatgaa    180

attttaatca acgttaaata ttctggtgta tgtcacaccg atttacatgc ttggcacggc    240

gattggccat tacctgttaa actaccatta gtaggtggtc atgaaggtgc tggtgtagtt    300

gtcaaactag gttccaatgt caagggctgg aaagtcggtg atttagcagg tatcaaatgg    360

ctgaacggtt cttgtatgac atgcgaattc tgtgaatcag gtcatgaatc aaattgtcca    420

gatgctgatt tatctggtta cactcatgat ggttctttcc aacaatttgc gaccgctgat    480

gctattcaag ccgccaaaat tcaacagggt accgacttgg ccgaagtagc cccaatatta    540

tgtgctggtg ttactgtata taaagcacta aaagaggcag acttgaaagc tggtgactgg    600

gttgccatct ctggtgctgc aggtggcttg ggttccttgg ccgttcaata tgcaactgcg    660

atgggttaca gagttctagg tattgatgca ggtgaggaaa aggaaaaact tttcaagaaa    720

ttgggggggtg aagtattcat cgactttact aaaacaaaga atatggtttc tgacattcaa    780

gaagctacca aaggtggccc tcatggtgtc attaacgttt ccgtttctga agccgctatt    840

tctctatcta cggaatatgt tagaccatgt ggtaccgtcg ttttggttgg tttgcccgct    900

aacgcctacg ttaaatcaga ggtattctct catgtggtga agtccatcaa tatcaagggt    960

tcttatgttg gtaacagagc tgatacgaga gaagccttag acttctttag cagaggtttg   1020

atcaaatcac caatcaaaat tgttggatta tctgaattac caaaggttta tgacttgatg   1080

gaaaagggca agattttggg tagatacgtc gtcgatacta gtaaataa                1128
```

<210> SEQ ID NO 26
<211> LENGTH: 375
<212> TYPE: PRT
<213> ORGANISM: Saccharomyces cerevisiae
<220> FEATURE:
<223> OTHER INFORMATION: ALCOHOL DEHYDROGENASE 3 (ADH3)
<220> FEATURE:
<223> OTHER INFORMATION: ALCOHOL DEHYDROGENASE 3 (ADH3)

<400> SEQUENCE: 26

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
```

```
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335

Ser Arg Gly Leu Ile Lys Ser Pro Ile Lys Ile Val Gly Leu Ser Glu
            340                 345                 350

Leu Pro Lys Val Tyr Asp Leu Met Glu Lys Gly Lys Ile Leu Gly Arg
        355                 360                 365

Tyr Val Val Asp Thr Ser Lys
    370                 375
```

<210> SEQ ID NO 27
<211> LENGTH: 1149
<212> TYPE: DNA
<213> ORGANISM: Saccharomyces cerevisiae
<220> FEATURE:
<223> OTHER INFORMATION: ALCOHOL DEHYDROGENASE 4 (ADH4)
<220> FEATURE:
<223> OTHER INFORMATION: ALCOHOL DEHYDROGENASE 4 (ADH4)

<400> SEQUENCE: 27

```
atgtcttccg ttactgggtt ttacattcca ccaatctctt tctttggtga aggtgcttta      60

gaagaaaccg ctgattacat caaaaacaag gattacaaaa aggctttgat cgttactgat     120

cctggtattg cagctattgg tctctccggt agagtccaaa agatgttgga agaacgtgac     180

ttaaacgttg ctatctatga caaaactcaa ccaaacccaa atattgccaa tgtcacagct     240

ggtttgaagg ttttgaagga acaaaactct gaaattgttg tttccattgg tggtggttct     300

gctcacgaca atgctaaggc cattgcttta ttggctacta acggtgggga aatcggagac     360
```

```
tatgaaggtg tcaatcaatc taagaaggct gctttaccac tatttgccat caacactact    420

gctggtactg cttccgaaat gaccagattc actattatct ctaatgaaga aaagaaaatc    480

aagatggcta tcattgacaa caacgtcact ccagctgttg ctgtcaacga tccatctacc    540

atgtttggtt tgccacctgc tttgactgct gctactggtc tagatgcttt gactcactgt    600

atcgaagctt atgtttccac cgcctctaac ccaatcaccg atgcctgtgc tttgaagggt    660

attgatttga tcaatgaaag cttagtcgct gcatacaaag acggtaaaga caagaaggcc    720

agaactgaca tgtgttacgc tgaatacttg gcaggtatgg ctttcaacaa tgcttctcta    780

ggttatgttc atgcccttgc tcatcaactt ggtggtttct accacttgcc tcatggtgtt    840

tgtaacgctg tcttgttgcc tcatgttcaa gaggccaaca tgcaatgtcc aaaggccaag    900

aagagattag gtgaaattgc tttgcatttc ggtgcttctc aagaagatcc agaagaaacc    960

atcaaggctt tgcacgtttt aaacagaacc atgaacattc caagaaactt gaaagaatta   1020

ggtgttaaaa ccgaagattt tgaaattttg gctgaacacg ccatgcatga tgcctgccat   1080

ttgactaacc cagttcaatt caccaaagaa caagtggttg ccattatcaa gaaagcctat   1140

gaatattaa                                                           1149
```

```
<210> SEQ ID NO 28
<211> LENGTH: 382
<212> TYPE: PRT
<213> ORGANISM: Saccharomyces cerevisiae
<220> FEATURE:
<223> OTHER INFORMATION: ALCOHOL DEHYDROGENASE 4 (ADH4)
<220> FEATURE:
<223> OTHER INFORMATION: ALCOHOL DEHYDROGENASE 4 (ADH4)

<400> SEQUENCE: 28

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
    50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
    130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
        195                 200                 205
```

```
Ser Asn Pro Ile Thr Asp Ala Cys Ala Leu Lys Gly Ile Asp Leu Ile
    210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
    290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
    370                 375                 380


<210> SEQ ID NO 29
<211> LENGTH: 1056
<212> TYPE: DNA
<213> ORGANISM: Saccharomyces cerevisiae
<220> FEATURE:
<223> OTHER INFORMATION: ALCOHOL DEHYDROGENASE 5 (ADH5)
<220> FEATURE:
<223> OTHER INFORMATION: ALCOHOL DEHYDROGENASE 5 (ADH5)

<400> SEQUENCE: 29

atgccttcgc aagtcattcc tgaaaaacaa aaggctattg tcttttatga gacagatgga      60

aaattggaat ataaagacgt cacagttccg gaacctaagc ctaacgaaat tttagtccac     120

gttaaatatt ctggtgtttg tcatagtgac ttgcacgcgt ggcacggtga ttggccattt     180

caattgaaat ttccattaat cggtggtcac gaaggtgctg gtgttgttgt taagttggga     240

tctaacgtta agggctggaa agtcggtgat tttgcaggta taaaatggtt gaatgggact     300

tgcatgtcct gtgaatattg tgaagtaggt aatgaatctc aatgtcctta tttggatggt     360

actggcttca cacatgatgg tacttttcaa gaatacgcaa ctgccgatgc cgttcaagct     420

gcccatattc caccaaacgt caatcttgct gaagttgccc caatcttgtg tgcaggtatc     480

actgtttata aggcgttgaa aagagccaat gtgataccag gccaatgggt cactatatcc     540

ggtgcatgcg gtggcttggg ttctctggca atccaatacg cccttgctat gggttacagg     600

gtcattggta tcgatggtgg taatgccaag cgaaagttat ttgaacaatt aggcggagaa     660

atattcatcg atttcacgga agaaaaagac attgttggtg ctataataaa ggccactaat     720

ggcggttctc atggagttat taatgtgtct gtttctgaag cagctatcga ggcttctacg     780

aggtattgta ggcccaatgg tactgtcgtc ctggttggta tgccagctca tgcttactgc     840

aattccgatg ttttcaatca agttgtaaaa tcaatctcca tcgttggatc ttgtgttgga     900

aatagagctg atacaaggga ggctttagat ttcttcgcca gaggtttgat caaatctccg     960

atccacttag ctggcctatc ggatgttcct gaaatttttg caaagatgga gaagggtgaa    1020
```

attgttggta gatatgttgt tgagacttct aaatga 1056

<210> SEQ ID NO 30
<211> LENGTH: 351
<212> TYPE: PRT
<213> ORGANISM: Saccharomyces cerevisiae
<220> FEATURE:
<223> OTHER INFORMATION: ALCOHOL DEHYDROGENASE 5 (ADH5)
<220> FEATURE:
<223> OTHER INFORMATION: ALCOHOL DEHYDROGENASE 5 (ADH5)

<400> SEQUENCE: 30

```
Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
```

340 345 350

<210> SEQ ID NO 31
<211> LENGTH: 951
<212> TYPE: DNA
<213> ORGANISM: Escherichia coli
<220> FEATURE:
<223> OTHER INFORMATION: ACETALDEHYDE-COA DEHYDROGENASE (MHPF)
<220> FEATURE:
<223> OTHER INFORMATION: ACETALDEHYDE-COA DEHYDROGENASE (MHPF)

<400> SEQUENCE: 31
atgagtaaac ggaaagtagc gatcatcggt tccgggaata ttgggacaga tttaatgata 60
aaaattctca ggcacggaca acatttagag atggctgtca tggttggcat agatcctcaa 120
agcgatggtt tagcgcgtgc tcgaaggatg ggcgtggcta ctacacacga gggtgttatc 180
ggacttatga atatgcccga attcgccgac atcgacatcg tttttgacgc gacatctgct 240
ggcgcacatg ttaagaacga tgccgcgctg cgtgaagcga agcctgatat tcgcttaatt 300
gacctaaccc ctgctgccat cggaccgtat tgtgttcctg tggtgaattt agaggcaaat 360
gtcgaccaat tgaacgttaa tatggtgaca tgcggaggtc aggctacaat acccatggtt 420
gctgctgtaa gccgagtcgc tagagttcat tacgcagaaa ttattgcctc gattgcctcg 480
aaatctgcag gcccgggcac tagagctaat attgacgaat ttaccgaaac cactagcaga 540
gcaatagagg tagttggtgg agcagccaaa ggaaaagcaa tcatagtctt aaatccagcc 600
gagccaccac taatgatgag agatactgtg tatgtattgt ccgatgaagc ctcacaggat 660
gatattgaag cttctatcaa cgaaatggca gaggccgttc aagcttacgt acctggttat 720
agactgaaac aaagagtcca gtttgaagtc ataccacaag ataagccagt gaacctacca 780
ggtgtgggtc aattcagtgg tcttaagacg gcagtatggc ttgaagttga aggtgccgct 840
cattacttgc cagcttatgc tggtaacttg gatataatga cttcatccgc attggcaacg 900
gcagaaaaga tggctcagtc attggcaaga aaggctggtg aagctgctta a 951

<210> SEQ ID NO 32
<211> LENGTH: 316
<212> TYPE: PRT
<213> ORGANISM: Escherichia coli
<220> FEATURE:
<223> OTHER INFORMATION: ACETALDEHYDE-COA DEHYDROGENASE (MHPF)
<220> FEATURE:
<223> OTHER INFORMATION: ACETALDEHYDE-COA DEHYDROGENASE (MHPF)

<400> SEQUENCE: 32

Met Ser Lys Arg Lys Val Ala Ile Ile Gly Ser Gly Asn Ile Gly Thr
1 5 10 15

Asp Leu Met Ile Lys Ile Leu Arg His Gly Gln His Leu Glu Met Ala
20 25 30

Val Met Val Gly Ile Asp Pro Gln Ser Asp Gly Leu Ala Arg Ala Arg
35 40 45

Arg Met Gly Val Ala Thr Thr His Glu Gly Val Ile Gly Leu Met Asn
50 55 60

Met Pro Glu Phe Ala Asp Ile Asp Ile Val Phe Asp Ala Thr Ser Ala
65 70 75 80

Gly Ala His Val Lys Asn Asp Ala Ala Leu Arg Glu Ala Lys Pro Asp
85 90 95

Ile Arg Leu Ile Asp Leu Thr Pro Ala Ala Ile Gly Pro Tyr Cys Val
100 105 110

-continued

```
Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315


<210> SEQ ID NO 33
<211> LENGTH: 1203
<212> TYPE: DNA
<213> ORGANISM: Escherichia coli
<220> FEATURE:
<223> OTHER INFORMATION: ACETATE KINASE (ACKA)
<220> FEATURE:
<223> OTHER INFORMATION: ACETATE KINASE (ACKA)

<400> SEQUENCE: 33

atgtcctcta aattggtttt ggttttgaac tgcggttcct cctctttgaa attcgctatt      60

attgatgctg tcaacggtga agaatacttg tctggtttgg ctgaatgttt ccatttgcct     120

gaagctagaa tcaagtggaa aatggatggt aacaaacaag aagctgcttt gggtgctggt     180

gctgctcatt ctgaagcttt gaattttatc gtcaacacca tcttggctca aaagccagaa     240

ttgtctgctc aattgactgc tattggtcat agaatagttc acggtggtga aaagtacacc     300

tcctctgttg ttattgatga atccgttatc caaggtatta aggatgctgc ttcttttgct     360

ccattgcata atccagctca tttgatcggt attgaagaag ccttgaagtc tttcccacaa     420

ttgaaggata agaacgttgc tgttttcgat accgctttcc atcaaactat gcctgaagaa     480

tcttacttgt acgctttgcc atacaacttg tacaaagaac acggtattag aagatacggt     540

gctcatggta cttctcattt ctacgttact caagaagccg ctaagatgtt gaacaaacca     600

gttgaagaat tgaacatcat tacctgccat ttgggtaatg gtggttctgt ttctgctatt     660

agaaacggta aatgcgttga tacctctatg ggtttgactc cattggaagg tttggttatg     720

ggtactagat ctggtgatat tgatccagcc attatcttcc acttgcatga tactttgggt     780

atgtctgttg atgccattaa caagttgttg accaaagaat caggtttgtt gggtttaacc     840
```

-continued

```
gaagttactt ctgattgcag atacgtcgaa gataactacg ctacaaaaga agatgctaag    900

agagctatgg acgtttactg tcatagattg gctaagtaca ttggtgctta cactgctttg    960

atggacggta gattggatgc tgttgttttt actggtggta ttggtgaaaa tgctgccatg   1020

gttagagaat tgtcattggg taaattgggt gtcttgggtt ttgaagttga tcacgaaaga   1080

aatttggctg ccagatttgg taaatccggt ttcattaaca aagaaggtac tagaccagcc   1140

gttgttattc caactaacga agaattggtt attgcccaag atgcttctag attgaccgct   1200

taa                                                                 1203
```

<210> SEQ ID NO 34
<211> LENGTH: 400
<212> TYPE: PRT
<213> ORGANISM: Escherichia coli
<220> FEATURE:
<223> OTHER INFORMATION: ACETATE KINASE (ACKA)
<220> FEATURE:
<223> OTHER INFORMATION: ACETATE KINASE (ACKA)

<400> SEQUENCE: 34

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285
```

-continued

```
Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
            340                 345                 350

Gly Phe Glu Val Asp His Glu Arg Asn Leu Ala Ala Arg Phe Gly Lys
        355                 360                 365

Ser Gly Phe Ile Asn Lys Glu Gly Thr Arg Pro Ala Val Val Ile Pro
    370                 375                 380

Thr Asn Glu Glu Leu Val Ile Ala Gln Asp Ala Ser Arg Leu Thr Ala
385                 390                 395                 400


<210> SEQ ID NO 35
<211> LENGTH: 990
<212> TYPE: DNA
<213> ORGANISM: Corynebacterium glutamicum
<220> FEATURE:
<223> OTHER INFORMATION: PHOSPHATE ACETYL TRANSFERASE (PTA)
<220> FEATURE:
<223> OTHER INFORMATION: PHOSPHATE ACETYL TRANSFERASE (PTA)

<400> SEQUENCE: 35

atgtctgcag aattgttcga gaattggttg ttgaagagag ccagagctga gcatagccac      60

attgtgttac cagaaggcga cgatgatcgt atactaatgg cagctcacca attgttagac     120

caagacattt gcgacattac gatactaggt gatcctgtca aaattaagga aagagcaacg     180

gagttaggat tacaccttaa cacagcatat ttggtcaatc ccttgactga tcctagactt     240

gaagagtttg ctgaacaatt cgcggaactg aggaaatcga aaagtgtcac aattgacgaa     300

gctagggaaa tcatgaagga catttcgtat tttgggacca tgatggtcca taatggagat     360

gcagatggaa tggtgtctgg tgctgcaaac actactgccc ataccataaa accttcattt     420

cagatcatta agaccgtacc agaagcttca gtcgtgtcct ctatcttcct tatggttctg     480

agaggaagat tgtgggcttt tggtgattgt gccgttaatc cgaatcctac agctgagcaa     540

ctaggcgaaa ttgccgtagt atctgcgaaa acagctgcac agtttgggat cgatccaaga     600

gtggccattt tatcctacag tactggcaat agtggtggag gtagcgatgt tgatagagcc     660

attgatgcct tagcggaagc tagacgtttg aatcctgaat tgtgtgttga cggtccatta     720

cagttcgatg ctgctgtaga tccaggcgtt gctaggaaga agatgccaga ttccgatgtt     780

gctggacaag caaatgtttt catctttcca gatcttgaag ccggtaacat tgggtacaaa     840

actgcccaaa gaactggtca tgcactagca gttggtccca tattacaagg tttgaacaaa     900

cccgttaacg acctgtcaag ggtgcaaca gtaccggaca tagtgaacac cgttgctata     960

acagcaatcc aagcgggcgg tagatcataa                                      990


<210> SEQ ID NO 36
<211> LENGTH: 714
<212> TYPE: PRT
<213> ORGANISM: Corynebacterium glutamicum
<220> FEATURE:
<223> OTHER INFORMATION: PHOSPHATE ACETYL TRANSFERASE (PTA)
<220> FEATURE:
<223> OTHER INFORMATION: PHOSPHATE ACETYL TRANSFERASE (PTA)

<400> SEQUENCE: 36
```

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
    370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415
```

```
Thr Val Lys Ala Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
    450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
    530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
    610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
    690                 695                 700

Leu Thr Ala Ile Gln Ser Ala Gln Gln Gln
705                 710


<210> SEQ ID NO 37
<211> LENGTH: 554
<212> TYPE: DNA
<213> ORGANISM: Saccharomyces cerevisiae
<220> FEATURE:
<223> OTHER INFORMATION: pTDH3
<220> FEATURE:
<223> OTHER INFORMATION: pTDH3

<400> SEQUENCE: 37

ccaaaatagg gggcgggtta cacagaatat ataacatcgt aggtgtctgg gtgaacagtt      60

tattcctggc atccactaaa tataatggag cccgcttttt aagctggcat ccagaaaaaa     120

aaagaatccc agcaccaaaa tattgttttc ttcaccaacc atcagttcat aggtccattc     180

tcttagcgca actacagaga acaggggcac aaacaggcaa aaaacgggca caacctcaat     240

ggagtgatgc aacctgcctg gagtaaatga tgacacaagg caattgaccc acgcatgtat     300
```

ctatctcatt ttcttacacc ttctattacc ttctgctctc tctgatttgg aaaaagctga 360
aaaaaaaggt tgaaaccagt tccctgaaat tattccccta cttgactaat aagtatataa 420
agacggtagg tattgattgt aattctgtaa atctatttct taaacttctt aaattctact 480
tttatagtta gtcttttttt tagttttaaa acaccaagaa cttagtttcg aataaacaca 540
cataaacaaa caaa 554

<210> SEQ ID NO 38
<211> LENGTH: 550
<212> TYPE: DNA
<213> ORGANISM: Saccharomyces cerevisiae
<220> FEATURE:
<223> OTHER INFORMATION: pENO2
<220> FEATURE:
<223> OTHER INFORMATION: pENO2

<400> SEQUENCE: 38
cgctcagcat ctgcttcttc ccaaagatga acgcggcgtt atgtcactaa cgacgtgcac 60
caacttgcgg aaagtggaat cccgttccaa aactggcatc cactaattga tacatctaca 120
caccgcacgc ctttttttctg aagcccactt tcgtggactt tgccatatgc aaaattcatg 180
aagtgtgata ccaagtcagc atacacctca ctagggtagt ttctttggtt gtattgatca 240
tttggttcat cgtggttcat taattttttt tctccattgc tttctggctt tgatcttact 300
atcatttgga tttttgtcga aggttgtaga attgtatgtg acaagtggca ccaagcatat 360
ataaaaaaaa aaagcattat cttcctacca gagttgattg ttaaaaacgt atttatagca 420
aacgcaattg taattaattc ttattttgta tcttttcttc ccttgtctca atcttttatt 480
tttattttat ttttcttttc ttagtttctt tcataacacc aagcaactaa tactataaca 540
tacaataata 550

<210> SEQ ID NO 39
<211> LENGTH: 419
<212> TYPE: DNA
<213> ORGANISM: Saccharomyces cerevisiae
<220> FEATURE:
<223> OTHER INFORMATION: pTEF Kl
<220> FEATURE:
<223> OTHER INFORMATION: pTEF Kl

<400> SEQUENCE: 39
ctctctcgca ataacaatga acactgggtc aatcatagcc tacacaggtg aacagagtag 60
cgtttataca gggtttatac ggtgattcct acggcaaaaa tttttcattt ctaaaaaaaa 120
aaagaaaaat ttttctttcc aacgctagaa ggaaaagaaa aatctaatta aattgatttg 180
gtgattttct gagagttccc tttttcatat atcgaatttt gaatataaaa ggagatcgaa 240
aaaatttttc tattcaatct gttttctggt tttatttgat agttttttttg tgtattatta 300 ttatggatta gtactggttt atatgggttt ttctgtataa cttcttttta ttttagtttg 360
tttaatctta ttttgagtta cattatagtt ccctaactgc aagagaagta acattaaaa 419

<210> SEQ ID NO 40
<211> LENGTH: 598
<212> TYPE: DNA
<213> ORGANISM: Saccharomyces cerevisiae
<220> FEATURE:
<223> OTHER INFORMATION: pTEF3
<220> FEATURE:
<223> OTHER INFORMATION: pTEF3

<400> SEQUENCE: 40

```
ggctgataat agcgtataaa caatgcatac tttgtacgtt caaaatacaa tgcagtagat      60

atatttatgc atattacata taatacatat cacataggaa gcaacaggcg cgttggactt     120

ttaattttcg aggaccgcga atccttacat cacacccaat cccccacaag tgatccccca     180

cacaccatag cttcaaaatg tttctactcc ttttttactc ttccagattt tctcggactc     240

cgcgcatcgc cgtaccactt caaaacaccc aagcacagca tactaaattt cccctctttc     300

ttcctctagg gtgtcgttaa ttacccgtac taaaggtttg gaaaagaaaa aagagaccgc     360

ctcgtttctt tttcttcgtc gaaaaaggca ataaaaattt ttatcacgtt tctttttctt     420

gaaaattttt ttttttgatt tttttctctt tcgatgacct cccattgata tttaagttaa     480

taaacggtct tcaatttctc aagtttcagt ttcatttttc ttgttctatt acaacttttt     540

ttacttcttg ctcattagaa agaaagcata gcaatctaat ctaagtttta attacaaa       598
```

<210> SEQ ID NO 41
<211> LENGTH: 383
<212> TYPE: DNA
<213> ORGANISM: Saccharomyces cerevisiae
<220> FEATURE:
<223> OTHER INFORMATION: pTEF1
<220> FEATURE:
<223> OTHER INFORMATION: pTEF1

<400> SEQUENCE: 41

```
gtttagcttg cctcgtcccc gccgggtcac ccggccagcg acatggaggc ccagaatacc      60

ctccttgaca gtcttgacgt gcgcagctca ggggcatgat gtgactgtcg cccgtacatt     120

tagcccatac atccccatgt ataatcattt gcatccatac attttgatgg ccgcacggcg     180

cgaagcaaaa attacggctc ctcgctgcag acctgcgagc agggaaacgc tcccctcaca     240

gacgcgttga attgtcccca cgccgcgccc ctgtagagaa atataaaagg ttaggatttg     300

ccactgaggt tcttctttca tatacttcct tttaaaatct tgctacgata cagttctcac     360

atcacatccg aacataaaca acc                                             383
```

<210> SEQ ID NO 42
<211> LENGTH: 700
<212> TYPE: DNA
<213> ORGANISM: Saccharomyces cerevisiae
<220> FEATURE:
<223> OTHER INFORMATION: pADH1
<220> FEATURE:
<223> OTHER INFORMATION: pADH1

<400> SEQUENCE: 42

```
gggtgtacaa tatggacttc ctcttttctg gcaaccaaac ccatacatcg ggattcctat      60

aataccttcg ttggtctccc taacatgtag gtggcggagg ggagatatac aatagaacag     120

ataccagaca agacataatg ggctaaacaa gactacacca attacactgc ctcattgatg     180

gtggtacata acgaactaat actgtagccc tagacttgat agccatcatc atatcgaagt     240

ttcactaccc tttttccatt tgccatctat tgaagtaata ataggcgcat gcaacttctt     300

ttcttttttt ttcttttctc tctcccccgt tgttgtctca ccatatccgc aatgacaaaa     360

aaatgatgga agacactaaa ggaaaaaatt aacgacaaag acagcaccaa cagatgtcgt     420

tgttccagag ctgatgaggg gtatctcgaa gcacacgaaa ctttttcctt ccttcattca     480

cgcacactac tctctaatga gcaacggtat acggccttcc ttccagttac ttgaatttga     540

aataaaaaaa agtttgctgt cttgctatca agtataaata gacctgcaat tattaatctt     600
```

ttgtttcctc gtcattgttc tcgttccctt tcttccttgt ttcttttttct gcacaatatt 660 tcaagctata ccaagcatac aatcaactat ctcatataca 700

<210> SEQ ID NO 43
<211> LENGTH: 549
<212> TYPE: DNA
<213> ORGANISM: Saccharomyces cerevisiae
<220> FEATURE:
<223> OTHER INFORMATION: pGPM 1
<220> FEATURE:
<223> OTHER INFORMATION: pGPM 1

<400> SEQUENCE: 43
gccaaacttt tcggttaaca catgcagtga tgcacgcgcg atggtgctaa gttacatata 60
tatatatata tatatatata tatatatata gccatagtga tgtctaagta acctttatgg 120
tatatttctt aatgtggaaa gatactagcg cgcgcaccca cacacaagct tcgtcttttc 180
ttgaagaaaa gaggaagctc gctaaatggg attccacttt ccgttccctg ccagctgatg 240
gaaaaaggtt agtggaacga tgaagaataa aaagagagat ccactgaggt gaaatttcag 300
ctgacagcga gtttcatgat cgtgatgaac aatggtaacg agttgtggct gttgccaggg 360
agggtggttc tcaactttta atgtatggcc aaatcgctac ttgggtttgt tatataacaa 420
agaagaaata atgaactgat tctcttcctc cttcttgtcc tttcttaatt ctgttgtaat 480
taccttcctt tgtaattttt tttgtaatta ttcttcttaa taatccaaac aaacacacat 540
attacaata 549

<210> SEQ ID NO 44
<211> LENGTH: 650
<212> TYPE: DNA
<213> ORGANISM: Saccharomyces cerevisiae
<220> FEATURE:
<223> OTHER INFORMATION: pFBA1
<220> FEATURE:
<223> OTHER INFORMATION: pFBA1

<400> SEQUENCE: 44
acgcaagccc taagaaatga ataacaatac tgacagtact aaataattgc ctacttggct 60
tcacatacgt tgcatacgtc gatatagata ataatgataa tgacagcagg attatcgtaa 120
tacgtaatag ttgaaaatct caaaaatgtg tgggtcatta cgtaaataat gataggaatg 180
ggattcttct atttttcctt tttccattct agcagccgtc gggaaaacgt ggcatcctct 240
ctttcgggct caattggagt cacgctgccg tgagcatcct ctctttccat atctaacaac 300
tgagcacgta accaatggaa aagcatgagc ttagcgttgc tccaaaaaag tattggatgg 360
ttaataccat ttgtctgttc tcttctgact ttgactcctc aaaaaaaaaa aatctacaat 420
caacagatcg cttcaattac gccctcacaa aaactttttt ccttcttctt cgcccacgtt 480
aaattttatc cctcatgttg tctaacggat ttctgcactt gatttattat aaaaagacaa 540
agacataata cttctctatc aatttcagtt attgttcttc cttgcgttat tcttctgttc 600 ttcttttct tttgtcatat ataaccataa ccaagtaata catattcaaa 650

<210> SEQ ID NO 45
<211> LENGTH: 700
<212> TYPE: DNA
<213> ORGANISM: Saccharomyces cerevisiae
<220> FEATURE:
<223> OTHER INFORMATION: pPDC1
<220> FEATURE:
<223> OTHER INFORMATION: pPDC1

<400> SEQUENCE: 45
ttatttacct atctctaaac ttcaacacct tatatcataa ctaatatttc ttgagataag 60
cacactgcac ccataccttc cttaaaaacg tagcttccag tttttggtgg ttccggcttc 120
cttcccgatt ccgcccgcta aacgcatatt tttgttgcct ggtggcattt gcaaaatgca 180
taacctatgc atttaaaaga ttatgtatgc tcttctgact tttcgtgtga tgaggctcgt 240
ggaaaaaatg aataatttat gaatttgaga acaattttgt gttgttacgg tattttacta 300
tggaataatc aatcaattga ggattttatg caaatatcgt ttgaatattt ttccgaccct 360
ttgagtactt ttcttcataa ttgcataata ttgtccgctg ccccttttc tgttagacgg 420 tgtcttgatc tacttgctat cgttcaacac caccttattt tctaactatt tttttttag 480 ctcatttgaa tcagcttatg gtgatggcac atttttgcat aaacctagct gtcctcgttg 540
aacataggaa aaaaaatat ataaacaagg ctctttcact ctccttgcaa tcagatttgg 600
gtttgttccc tttattttca tatttcttgt catattcctt tctcaattat tattttctac 660
tcataacctc acgcaaaata acacagtcaa atcaatcaaa 700

<210> SEQ ID NO 46
<211> LENGTH: 998
<212> TYPE: DNA
<213> ORGANISM: Saccharomyces cerevisiae
<220> FEATURE:
<223> OTHER INFORMATION: pCCW12
<220> FEATURE:
<223> OTHER INFORMATION: pCCW12

<400> SEQUENCE: 46
aaccagggca aagcaaaata aaagaaactt aatacgttat gccgtaatga agggctacca 60
aaaacgataa tctcaactgt aaacaggtac aatgcggacc cttttgccac aaaacataca 120
tcattcattg ccggaaaaag aaagaagtga agacagcagt gcagccagcc atgttgcgcc 180
aatctaatta tagatgctgg tgccctgagg atgtatctgg agccagccat ggcatcatgc 240
gctaccgccg gatgtaaaat ccgacacgca aaagaaaacc ttcgaggttg cgcacttcgc 300
ccacccatga accacacggt tagtccaaaa ggggcagttc agattccaga tgcgggaatt 360
agcttgctgc caccctcacc tcactaacgc tgcggtgtgc ggatacttca tgctatttat 420
agacgcgcgt gtcggaatca gcacgcgcaa gaaccaaatg ggaaaatcgg aatgggtcca 480
gaactgcttt gagtgctggc tattggcgtc tgatttccgt tttgggaatc ctttgccgcg 540
cgcccctctc aaaactccgc acaagtccca gaaagcggga aagaaataaa acgccaccaa 600
aaaaaaaaat aaaagccaat cctcgaagcg tgggtggtag gccctggatt atcccgtaca 660
agtatttctc aggagtaaaa aaaccgtttg ttttggaatt ccccatttcg cggccaccta 720
cgccgctatc tttgcaacaa ctatctgcga taactcagca aattttgcat attcgtgttg 780
cagtattgcg ataatgggag tcttacttcc aacataacgg cagaaagaaa tgtgagaaaa 840
ttttgcatcc tttgcctccg ttcaagtata taaagtcggc atgcttgata atctttcttt 900
ccatcctaca ttgttctaat tattcttatt ctcctttatt ctttcctaac ataccaagaa 960
attaatcttc tgtcattcgc ttaaacacta tatcaata 998

<210> SEQ ID NO 47
<211> LENGTH: 700
<212> TYPE: DNA
<213> ORGANISM: Saccharomyces cerevisiae
<220> FEATURE:

<223> OTHER INFORMATION: pGK1
<220> FEATURE:
<223> OTHER INFORMATION: pGK1

<400> SEQUENCE: 47
gtgagtaagg aaagagtgag gaactatcgc atacctgcat ttaaagatgc cgatttgggc 60
gcgaatcctt tattttggct tcaccctcat actattatca gggccagaaa aaggaagtgt 120
ttccctcctt cttgaattga tgttaccctc ataaagcacg tggcctctta tcgagaaaga 180
aattaccgtc gctcgtgatt tgtttgcaaa aagaacaaaa ctgaaaaaac ccagacacgc 240
tcgacttcct gtcttcctat tgattgcagc ttccaatttc gtcacacaac aaggtcctag 300
cgacggctca caggttttgt aacaagcaat cgaaggttct ggaatggcgg gaaagggttt 360
agtaccacat gctatgatgc ccactgtgat ctccagagca aagttcgttc gatcgtactg 420
ttactctctc tctttcaaac agaattgtcc gaatcgtgtg acaacaacag cctgttctca 480
cacactcttt tcttctaacc aagggggtgg tttagtttag tagaacctcg tgaaacttac 540
atttacatat atataaactt gcataaattg gtcaatgcaa gaaatacata tttggtcttt 600
tctaattcgt agtttttcaa gttcttagat gctttctttt tctctttttt acagatcatc 660
aaggaagtaa ttatctactt tttacaacaa atataaaaca 700

<210> SEQ ID NO 48
<211> LENGTH: 913
<212> TYPE: DNA
<213> ORGANISM: Saccharomyces cerevisiae
<220> FEATURE:
<223> OTHER INFORMATION: pMDH2
<220> FEATURE:
<223> OTHER INFORMATION: pMDH2

<400> SEQUENCE: 48
ccttcgctaa ataataaacc tgaactgtac ttagcgaagc cttcatagca cctacgtaca 60
cgtatatata gacattttac gtaatggaga aactgaggtt tttgttttca cttttttttct 120 ttctttttca ctattgctcg aaccgcctgc gatgagctaa gaaaaaaaag tgaaagaaat 180
catagaaagc aaaaatgaga ttatatagcc cagagccctc ttctggcgcc tgtcccaagg 240
cggaccaaca acaacacttg cccaaaccta agaaaatccc ctcatacttt tccgtttgta 300
tctcctactt tcttacttcc tttttttctt ctttatttgc ttggtttacc attgaagtcc 360
atttttacta cagacaatag ctagtcattc gctatcttcc gtttgtcact ttttttcaaa 420
tttctcatct atatagcgaa gtacggaaaa gatgtcactt gccggcatct cggccttccc 480
cggccaaatg gactcatcat ctacgatacg gcccctttaa tccgcaatta ctttgcccat 540
tcggccgtag ccgttctaaa gccgccgtgc cttgcccccca atactcccct aatgatccgg 600
gaagttccgg tttttttcct ttgtttagtg gcattttgtg ttgcccaagg ttgggaaggt 660
ccgatttgac tttaaggaac tacggaaggt atctaaggtt tctaaaaaca atatacacgc 720
gcgtgcgtag atatataaag ataaagattt atcgatatga gataaagatt gctgcatgat 780
tctccttctg attctttttc cctgtatata ttttctcccc ttctgtataa atcgtacagt 840
cagaagtagt ccagaatata gtgctgcaga ctattacaaa agttcaatac aatatcataa 900
aagttatagt aac 913

<210> SEQ ID NO 49
<211> LENGTH: 406
<212> TYPE: DNA
<213> ORGANISM: Saccharomyces cerevisiae
<220> FEATURE:
<223> OTHER INFORMATION: pURA3
<220> FEATURE:
<223> OTHER INFORMATION: pURA3

<400> SEQUENCE: 49
ggtacccaaa ccgaagttat ctgatgtaga aaaggattaa agatgctaag agatagtgat 60
gatatttcat aaataatgta attctatata tgttaattac ctttttttgcg aggcatattt 120 atggtgaagg ataagttttg accatcaaag aaggttaatg tggctgtggt ttcagggtcc 180
ataaagcttt tcaattcatc tttttttttt ttgttctttt ttttgattcc ggtttctttg 240
aaattttttt gattcggtaa tctccgagca gaaggaagaa cgaaggaagg agcacagact 300
tagattggta tatatacgca tatgtggtgt tgaagaaaca tgaaattgcc cagtattctt 360
aacccaactg cacagaacaa aaacctgcag gaaacgaaga taaatc 406

<210> SEQ ID NO 50
<211> LENGTH: 535
<212> TYPE: DNA
<213> ORGANISM: Saccharomyces cerevisiae
<220> FEATURE:
<223> OTHER INFORMATION: pRPLA1
<220> FEATURE:
<223> OTHER INFORMATION: pRPLA1

<400> SEQUENCE: 50
tcaagttgga tactgatctg atctctccgc cctactacca gggaccctca tgattaccgc 60
tcgaatgcga cgtttcctgc ctcataaaac tggcttgaaa atatttattc gctgaacagt 120
agcctagctt ataaaaattt catttaatta atgtaatatg aaaactcaca tgccttctgt 180
ttctaaaatt gtcacagcaa gaaataacat taccatacgt gatcttatta aactctagta 240
tcttgtctaa tacttcattt aaaagaagcc ttaaccctgt agcctcatct atgtctgcta 300
catatcgtga ggtacgaata tcgtaagatg ataccacgca actttgtaat gatttttttt 360
ttttcatttt ttaaagaatg cctttacatg gtatttgaaa aaaatatctt tataaagttt 420
gcgatctctt ctgttctgaa taatttttag taaaagaaat caaaagaata aagaaatagt 480
ccgctttgtc caatacaaca gcttaaaccg attatctcta aaataacaag aagaa 535

<210> SEQ ID NO 51
<211> LENGTH: 400
<212> TYPE: DNA
<213> ORGANISM: Saccharomyces cerevisiae
<220> FEATURE:
<223> OTHER INFORMATION: pSAM4
<220> FEATURE:
<223> OTHER INFORMATION: pSAM4

<400> SEQUENCE: 51
agattttggt gttagatggt actcttgcat atgtaacctt taataaattt tgcaaatcga 60
attcctttgt aacgtgcaaa gcattttata gcctggcgct cgcattgtta agcaacaggc 120
ggtgcggcaa cgttgaaatg tttcacgcag ggttttttac gtactgcacg gcattctgga 180
gtgaaaaaaa atgaaaagta cagctcgaag ttttttgtcc atcggttgta ctttgcagag 240
tattagtcat ttttgatatc agagtactac tatcgaagca tttttacgct tgaataactt 300
gaatattatt gaaagcttag ttcaaccaag ctgaaaagaa ccattattca acataattgg 360
aaatcatttc gttactaaat cgtccgaaaa ttgcagaaaa 400

<210> SEQ ID NO 52

-continued

<211> LENGTH: 505
<212> TYPE: DNA
<213> ORGANISM: Saccharomyces cerevisiae
<220> FEATURE:
<223> OTHER INFORMATION: pCUP1-1
<220> FEATURE:
<223> OTHER INFORMATION: pCUP1-1

<400> SEQUENCE: 52

```
cggcaaactt caacgatttc tatgatgcat tttataatta gtaagccgat cccattaccg     60

acatttgggc gctatacgtg catatgttca tgtatgtatc tgtatttaaa acacttttgt    120

attatttttc ctcatatatg tgtataggtt tatacggatg atttaattat tacttcacca    180

ccctttattt caggctgata tcttagcctt gttactagtt agaaaaagac atttttgctg    240

tcagtcactg tcaagagatt cttttgctgg catttcttcc agaagcaaaa agagcgatgc    300

gtcttttccg ctgaaccgtt ccagcaaaaa agactaccaa cgcaatatgg attgtcagaa    360

tcatataaaa gagaagcaaa taactccttg tcttgtatca attgcattat aatatcttct    420

tgttagtgca atatcatata gaagtcatcg aaatagatat taagaaaaac aaactgtaca    480

atcaatcaat caatcatcac ataaa                                          505
```

<210> SEQ ID NO 53
<211> LENGTH: 500
<212> TYPE: DNA
<213> ORGANISM: Candida glabrata
<220> FEATURE:
<223> OTHER INFORMATION: pCUP1.Cgla
<220> FEATURE:
<223> OTHER INFORMATION: pCUP1.Cgla

<400> SEQUENCE: 53

```
cacaccacac aaccgtcagc accccggctg tacgtctgtg aaggctgcgg tatagacacg     60

gactgcgata cagaactcat gacttatatc tgtagactcc tctgcttcaa tgcgaactcc    120

aggatcaccg aatagcatgc gatgagctgt tgattcttat atataattat ctattgcatt    180

ttttttttaa tgctgcatgg gggggcctag taaatcaccc gtacaagtca cgcgtgagag    240

aaagagaagg gccctttcgt cgtggaagcg tggatcgtga gcgacctgtt tctaaatata    300

gcttttgggt aggatattat attaagtgaa attttattag agggtaaatg tatgtgaaag    360

ttatgtataa tatgttgcta aattagcgat cgtgaatgca tagaatctaa tcgttataga    420

aaaccgcaac ttgtgctgtt ttgttgtgtt ttcttgtcgt ttttttatat tatttatcta    480

gtattttgct ttagttgtta                                                500
```

<210> SEQ ID NO 54
<211> LENGTH: 425
<212> TYPE: DNA
<213> ORGANISM: Saccharomyces bayanus
<220> FEATURE:
<223> OTHER INFORMATION: pCUP1.Sba
<220> FEATURE:
<223> OTHER INFORMATION: pCUP1.Sba

<400> SEQUENCE: 54

```
agaaggaggg gtcctattac caatacttgg acgctatacg tgcatatgta catgtacgta     60

tctgtattta aacacttttg tattattttc tttatatatg tgtataggtt tacatggttg    120

acttttatca ttgtttgtgc acatttgcaa tggccatttt tttgtttttg agaaaggtat    180

tattgctgtc actattcgag atgcttttgc tgacattcct cctagaagcc aaaaggccga    240

tgcgtttttt ccgctgagag gataccagca aaaaaagcta ccagtacaag atgggacggc    300
```

```
aaaagcgtat aaaagaagaa gcaaaatgac cagatatgct ttcaatttca tcaatgtttc    360

tttctccctg ttatgatcca gaagaataat caaaagcaaa acatctattc aatcaatctc    420

ataaa                                                                425
```

<210> SEQ ID NO 55
<211> LENGTH: 741
<212> TYPE: DNA
<213> ORGANISM: Artificial Sequence
<220> FEATURE:
<223> OTHER INFORMATION: pACU1
<220> FEATURE:
<223> OTHER INFORMATION: pACU1

<400> SEQUENCE: 55

```
ttacattatc aatccttgcg tttcagcttc cactaattta gatgactatt tctcatcatt     60

tgcgtcatct tctaacaccg tatatgataa tatactagta acgtaaatac tagttagtag    120

atgatagttg atttttattc caacactaag aaataatttc gccatttctt gaatgtattt    180

aaagatattt aatgctataa tagacattta aatccaattc ttccaacata caatgggagt    240

ttggccgagt ggtttaaggc gtcagattta ggtggattta acctctaaaa tctctgatat    300

cttcggatgc aagggttcga atcccttagc tctcattatt ttttgctttt tctcttgaat    360

tcgaaaaaga catttttgct gtcagtcact gtcaagagat tcttttgctg gcatttcttc    420

cagaagcaaa aagagcgatg cgtcttttcc gctgaaccgt tccagcaaaa aagactacca    480

acgaattcta attaagttag tcaaggcgcc atcctcatga aaactgtgta acataataac    540

cgaagtgtcg aaaaggtggc accttgtcca attgaacacg ctcgatgaaa aaaataagat    600

atatataagg ttaagtaaag cgtctgttag aaaggaagtt tttccttttt cttgctctct    660

tgtcttttca tctactattt ccttcgtgta atacagggtc gtcagataca tagatacaat    720

tctattaccc ccatccatac a                                              741
```

<210> SEQ ID NO 56
<211> LENGTH: 757
<212> TYPE: DNA
<213> ORGANISM: Artificial Sequence
<220> FEATURE:
<223> OTHER INFORMATION: pACU2
<220> FEATURE:
<223> OTHER INFORMATION: pACU2

<400> SEQUENCE: 56

```
ttacattatc aatccttgcg tttcagcttc cactaattta gatgactatt tctcatcatt     60

tgcgtcatct tctaacaccg tatatgataa tatactagta acgtaaatac tagttagtag    120

atgatagttg atttttattc caacactaag aaataatttc gccatttctt gaatgtattt    180

aaagatattt aatgctataa tagacattta aatccaattc ttccaacata caatgggagt    240

ttggccgagt ggtttaaggc gtcagattta ggtggattta acctctaaaa tctctgatat    300

cttcggatgc aagggttcga atcccgaatt cgaaaaagac atttttgctg tcagtcactg    360

tcaagagatt cttttgctgg catttcttcc agaagcaaaa agagcgatgc gtcttttccg    420

ctgaaccgtt ccagcaaaaa agactaccaa cgaattccac gtgaagctgt cgatattggg    480

gaactgtggt ggttggcaaa tgactaatta agttagtcaa ggcgccatcc tcatgaaaac    540

tgtgtaacat aataaccgaa gtgtcgaaaa ggtggcacct tgtccaattg aacacgctcg    600

atgaaaaaaa taagatatat ataaggttaa gtaaagcgtc tgttagaaag gaagtttttc    660
```

cttttttcttg ctctcttgtc ttttcatcta ctatttcctt cgtgtaatac agggtcgtca 720
gatacataga tacaattcta ttacccccat ccataca 757

<210> SEQ ID NO 57
<211> LENGTH: 498
<212> TYPE: DNA
<213> ORGANISM: Artificial Sequence
<220> FEATURE:
<223> OTHER INFORMATION: pACU3p
<220> FEATURE:
<223> OTHER INFORMATION: pACU3p

<400> SEQUENCE: 57
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attcgaaaaa gacatttttg ctgtcagtca ctgtcaagag 180
attcttttgc tggcatttct tccagaagca aaaagagcga tgcgtctttt ccgctgaacc 240
gttccagcaa aaaagactac caacgaattc ggatgataat gcgattagtt ttttagcctt 300
atttctgggg taattaatca gcgaagcgat gatttttgat ctattaacag atatataaat 360
ggaaaagctg cataaccact ttaactaata ctttcaacat tttcagtttg tattacttct 420
tattcaaatg tcataaaagt atcaacaaaa aattgttaat atacctctat actttaacgt 480
caaggagaaa aaactata 498

<210> SEQ ID NO 58
<211> LENGTH: 498
<212> TYPE: DNA
<213> ORGANISM: Artificial Sequence
<220> FEATURE:
<223> OTHER INFORMATION: pACU4p
<220> FEATURE:
<223> OTHER INFORMATION: pACU4p

<400> SEQUENCE: 58
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attcgttggt agtctttttt gctggaacgg ttcagcggaa 180
aagacgcatc gctctttttg cttctggaag aaatgccagc aaaagaatct cttgacagtg 240
actgacagca aaaatgtctt tttcgaattc ggatgataat gcgattagtt ttttagcctt 300
atttctgggg taattaatca gcgaagcgat gatttttgat ctattaacag atatataaat 360
ggaaaagctg cataaccact ttaactaata ctttcaacat tttcagtttg tattacttct 420
tattcaaatg tcataaaagt atcaacaaaa aattgttaat atacctctat actttaacgt 480
caaggagaaa aaactata 498

<210> SEQ ID NO 59
<211> LENGTH: 530
<212> TYPE: DNA
<213> ORGANISM: Artificial Sequence
<220> FEATURE:
<223> OTHER INFORMATION: pACU5
<220> FEATURE:
<223> OTHER INFORMATION: pACU5

<400> SEQUENCE: 59
ggaggacgaa acaaaaaagt gaaaaaaaat gaaaattttt ttggaaaacc aagaaatgaa 60
ttatatttcc gtgtgagacg acatcgtcga atatgattca gggtaacagt attgatgtaa 120
tcaatttcct acctgaatct aaaattcccg gaattcgaaa aagacatttt tgctgtcagt 180
cactgtcaag agattctttt gctggcattt cttccagaag caaaaagagc gatgcgtctt 240
ttccgctgaa ccgttccagc aaaaaagact accaacgaat tccgagcaga tccgccaggc 300
gtgtatatat agcgtggatg gccaggcaac tttagtgctg acacatacag gcatatatat 360
atgtgtgcga cgacacatga tcatatggca tgcatgtgct ctgtatgtat ataaaactct 420
tgttttcttc ttttctctaa atattctttc cttatacatt aggacctttg cagcataaat 480
tactatactt ctatagacac acaaacacaa atacacacac taaattaata 530

<210> SEQ ID NO 60
<211> LENGTH: 867
<212> TYPE: DNA
<213> ORGANISM: Artificial Sequence
<220> FEATURE:
<223> OTHER INFORMATION: pACU6
<220> FEATURE:
<223> OTHER INFORMATION: pACU6

<400> SEQUENCE: 60
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tcgaaaaaga catttttgct gtcagtcact gtcaagagat tcttttgctg gcatttcttc 420
cagaagcaaa aagagcgatg cgtcttttcc gctgaaccgt tccagcaaaa aagactacca 480
acgaattcga aaaagacatt tttgctgtca gtcactgtca agagattctt ttgctggcat 540
ttcttccaga agcaaaaaga gcgatgcgtc ttttccgctg aaccgttcca gcaaaaaaga 600
ctaccaacga attctaatta agttagtcaa ggcgccatcc tcatgaaaac tgtgtaacat 660
aataaccgaa gtgtcgaaaa ggtggcacct tgtccaattg aacacgctcg atgaaaaaaa 720
taagatatat ataaggttaa gtaaagcgtc tgttagaaag gaagttttc ctttttcttg 780 ctctcttgtc ttttcatcta ctatttcctt cgtgtaatac agggtcgtca gatacataga 840
tacaattcta ttacccccat ccataca 867

<210> SEQ ID NO 61
<211> LENGTH: 867
<212> TYPE: DNA
<213> ORGANISM: Artificial Sequence
<220> FEATURE:
<223> OTHER INFORMATION: pACU7
<220> FEATURE:
<223> OTHER INFORMATION: pACU7

<400> SEQUENCE: 61
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tcgttggtag tctttttttgc tggaacggtt cagcggaaaa gacgcatcgc tcttttttgct 420 tctggaagaa atgccagcaa aagaatctct tgacagtgac tgacagcaaa aatgtctttt 480
tcgaattcgt tggtagtctt ttttgctgga acggttcagc ggaaaagacg catcgctctt 540
tttgcttctg gaagaaatgc cagcaaaaga atctcttgac agtgactgac agcaaaaatg 600
tctttttcga attctaatta agttagtcaa ggcgccatcc tcatgaaaac tgtgtaacat 660
aataaccgaa gtgtcgaaaa ggtggcacct tgtccaattg aacacgctcg atgaaaaaaa 720
taagatatat ataaggttaa gtaaagcgtc tgttagaaag gaagtttttc ctttttcttg 780
ctctcttgtc ttttcatcta ctatttcctt cgtgtaatac agggtcgtca gatacataga 840
tacaattcta ttacccccat ccataca 867

<210> SEQ ID NO 62
<211> LENGTH: 1119
<212> TYPE: DNA
<213> ORGANISM: Artificial Sequence
<220> FEATURE:
<223> OTHER INFORMATION: pACU8
<220> FEATURE:
<223> OTHER INFORMATION: pACU8

<400> SEQUENCE: 62
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tcgaaaaaga catttttgct gtcagtcact gtcaagagat tcttttgctg gcatttcttc 420
cagaagcaaa aagagcgatg cgtcttttcc gctgaaccgt tccagcaaaa aagactacca 480
acgaattcga aaaagacatt tttgctgtca gtcactgtca agagattctt ttgctggcat 540
ttcttccaga agcaaaaaga gcgatgcgtc ttttccgctg aaccgttcca gcaaaaaaga 600
ctaccaacga attcgaaaaa gacatttttg ctgtcagtca ctgtcaagag attcttttgc 660
tggcatttct tccagaagca aaaagagcga tgcgtctttt ccgctgaacc gttccagcaa 720
aaaagactac caacgaattc gaaaaagaca tttttgctgt cagtcactgt caagagattc 780
ttttgctggc atttcttcca gaagcaaaaa gagcgatgcg tcttttccgc tgaaccgttc 840
cagcaaaaaa gactaccaac gaattctaat taagttagtc aaggcgccat cctcatgaaa 900
actgtgtaac ataataaccg aagtgtcgaa aaggtggcac cttgtccaat tgaacacgct 960
cgatgaaaaa aataagatat atataaggtt aagtaaagcg tctgttagaa aggaagtttt 1020
tcctttttct tgctctcttg tcttttcatc tactatttcc ttcgtgtaat acagggtcgt 1080
cagatacata gatacaattc tattaccccc atccataca 1119

<210> SEQ ID NO 63
<211> LENGTH: 624
<212> TYPE: DNA
<213> ORGANISM: Artificial Sequence
<220> FEATURE:
<223> OTHER INFORMATION: pACU9
<220> FEATURE:
<223> OTHER INFORMATION: pACU9

<400> SEQUENCE: 63
tatagttttt tctccttgac gttaaagtat agaggtatat taacaatttt ttgttgatac 60
ttttatgaca tttgaataag aagtaataca aactgaaaat gttgaaagta ttagttaaag 120
tggttatgca gcttttccat ttatatatct gttaatagat caaaaatcat cgcttcgctg 180
attaattacc ccagaaataa ggctaaaaaa ctaatcgcat tatcatccga attcgaaaaa 240
gacatttttg ctgtcagtca ctgtcaagag attcttttgc tggcatttct tccagaagca 300
aaaagagcga tgcgtctttt ccgctgaacc gttccagcaa aaaagactac caacgaattc 360
gaaaaagaca tttttgctgt cagtcactgt caagagattc ttttgctggc atttcttcca 420
gaagcaaaaa gagcgatgcg tcttttccgc tgaaccgttc cagcaaaaaa gactaccaac 480
gaattcgggc tctttacatt tccacaacat ataagtaaga ttagatatgg atatgtatat 540
ggtggtaatg ccatgtaata tgattattaa acttctttgc gtccatccaa aaaaaaagta 600
agaatttttg aaaattcaat ataa 624

<210> SEQ ID NO 64
<211> LENGTH: 876
<212> TYPE: DNA
<213> ORGANISM: Artificial Sequence
<220> FEATURE:
<223> OTHER INFORMATION: pACU10p
<220> FEATURE:
<223> OTHER INFORMATION: pACU10p

<400> SEQUENCE: 64
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attggttggt agtctttttt gctggaacgg ttcagcggaa 180
aagacgcatc gctctttttg cttctggaag aaatgccagc aaaagaatct cttgacagtg 240
actgacagca aaaatgtctt tttcgaattc gttggtagtc ttttttgctg gaacggttca 300
gcggaaaaga cgcatcgctc tttttgcttc tggaagaaat gccagcaaaa gaatctcttg 360
acagtgactg acagcaaaaa tgtctttttc gaattcgttg gtagtctttt ttgctggaac 420
ggttcagcgg aaaagacgca tcgctctttt tgcttctgga agaaatgcca gcaaaagaat 480
ctcttgacag tgactgacag caaaaatgtc tttttcgaat tcgttggtag tcttttttgc 540
tggaacggtt cagcggaaaa gacgcatcgc tctttttgct tctggaagaa atgccagcaa 600
aagaatctct tgacagtgac tgacagcaaa aatgtctttt tccaattcgg atgataatgc 660
gattagtttt ttagccttat ttctggggta attaatcagc gaagcgatga tttttgatct 720
attaacagat atataaatgg aaaagctgca taaccacttt aactaatact ttcaacattt 780
tcagtttgta ttacttctta ttcaaatgtc ataaaagtat caacaaaaaa ttgttaatat 840
acctctatac tttaacgtca aggagaaaaa actata 876

<210> SEQ ID NO 65
<211> LENGTH: 633
<212> TYPE: DNA
<213> ORGANISM: Artificial Sequence
<220> FEATURE:
<223> OTHER INFORMATION: pACU11
<220> FEATURE:
<223> OTHER INFORMATION: pACU11

<400> SEQUENCE: 65

```
gctcagcatc tgcttcttcc caaagatgaa cgcggcgtta tgtcactaac gacgtgcacc     60

aacttgcggg aattcgaaaa agacattttt gctgtcagtc actgtcaaga gattcttttg    120

ctggcatttc ttccagaagc aaaaagagcg atgcgtcttt tccgctgaac cgttccagca    180

aaaaagacta ccaacgaatt ccaccgcacg cctttttttct gaagcccact ttcgtggact   240

ttgccatata tgcaaaattc atgaagtgtg ataccaagtc agcatacacc tcactagggt    300

agtttctttg gttgtattga tcatttggtt catcgtggtt cattaatttt ttttctccat    360

tgctttctgg ctttgatctt actatcattt ggatttttgt cgaaggttgt agaattgtat    420

gtgacaagtg gcaccaagca tatataaaaa aaaaaaagcat tatcttccta ccagagttga   480

ttgttaaaaa cgtatttata gcaaacgcaa ttgtaattaa ttcttatttt gtatcttttc    540

ttcccttgtc tcaatctttt atttttattt tatttttctt ttcttagttt ctttcataac    600

accaagcaac taatactata acatacaata ata                                 633
```

<210> SEQ ID NO 66
<211> LENGTH: 1119
<212> TYPE: DNA
<213> ORGANISM: Artificial Sequence
<220> FEATURE:
<223> OTHER INFORMATION: pACU12
<220> FEATURE:
<223> OTHER INFORMATION: pACU12

<400> SEQUENCE: 66

```
ttacattatc aatccttgcg tttcagcttc cactaattta gatgactatt tctcatcatt     60

tgcgtcatct tctaacaccg tatatgataa tatactagta acgtaaatac tagttagtag    120

atgatagttg atttttattc caacactaag aaataatttc gccatttctt gaatgtattt    180

aaagatattt aatgctataa tagacattta aatccaattc ttccaacata caatgggagt    240

ttggccgagt ggtttaaggc gtcagattta ggtggattta acctctaaaa tctctgatat    300

cttcggatgc aagggttcga atcccttagc tctcattatt ttttgctttt tctcttgaat    360

tggttggtag tctttttttgc tggaacggtt cagcggaaaa gacgcatcgc tctttttgct   420

tctggaagaa atgccagcaa aagaatctct tgacagtgac tgacagcaaa aatgtctttt    480

tcgaattcgt tggtagtctt ttttgctgga acggttcagc ggaaaagacg catcgctctt    540

tttgcttctg gaagaaatgc cagcaaaaga atctcttgac agtgactgac agcaaaaatg    600

tctttttcga attcgttggt agtctttttt gctggaacgg ttcagcggaa aagacgcatc    660

gctcttttttg cttctggaag aaatgccagc aaaagaatct cttgacagtg actgacagca   720

aaaatgtctt tttcgaattc gttggtagtc tttttttgctg gaacggttca gcggaaaaga   780

cgcatcgctc tttttgcttc tggaagaaat gccagcaaaa gaatctcttg acagtgactg    840

acagcaaaaa tgtcttttttc caattctaat taagttagtc aaggcgccat cctcatgaaa   900

actgtgtaac ataataaccg aagtgtcgaa aaggtggcac cttgtccaat tgaacacgct    960

cgatgaaaaa aataagatat atataaggtt aagtaaagcg tctgttagaa aggaagtttt   1020

tcctttttct tgctctcttg tcttttcatc tactatttcc ttcgtgtaat acagggtcgt   1080

cagatacata gatacaattc tattaccccc atccataca                          1119
```

<210> SEQ ID NO 67
<211> LENGTH: 1497
<212> TYPE: DNA
<213> ORGANISM: Artificial Sequence
<220> FEATURE:
<223> OTHER INFORMATION: pACU13

<220> FEATURE:
<223> OTHER INFORMATION: pACU13

<400> SEQUENCE: 67

```
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg atttttattc caacactaag aaataatttc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tggttggtag tctttttgc tggaacggtt cagcggaaaa gacgcatcgc tctttttgct     420
tctggaagaa atgccagcaa aagaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg    600
tctttttcga attcgttggt agtctttttt gctggaacgg ttcagcggaa aagacgcatc    660
gctcttttg cttctggaag aaatgccagc aaaagaatct cttgacagtg actgacagca     720
aaaatgtctt tttcgaattc gttggtagtc tttttgctg gaacggttca gcggaaaaga     780
cgcatcgctc tttttgcttc tggaagaaat gccagcaaaa gaatctcttg acagtgactg    840
acagcaaaaa tgtctttttc gaattcgttg gtagtctttt ttgctggaac ggttcagcgg    900
aaaagacgca tcgctctttt tgcttctgga agaaatgcca gcaaaagaat ctcttgacag    960
tgactgacag caaaaatgtc tttttcgaat tcgttggtag tctttttgc tggaacggtt    1020
cagcggaaaa gacgcatcgc tctttttgct tctggaagaa atgccagcaa aagaatctct   1080
tgacagtgac tgacagcaaa aatgtctttt tcgaattcgt tggtagtctt ttttgctgga   1140
acggttcagc ggaaaagacg catcgctctt tttgcttctg gaagaaatgc cagcaaaaga   1200
atctcttgac agtgactgac agcaaaaatg tctttttcca attctaatta agttagtcaa   1260
ggcgccatcc tcatgaaaac tgtgtaacat aataaccgaa gtgtcgaaaa ggtggcacct   1320
tgtccaattg aacacgctcg atgaaaaaaa taagatatat ataaggttaa gtaaagcgtc   1380
tgttagaaag gaagtttttc ctttttcttg ctctcttgtc ttttcatcta ctatttcctt   1440
cgtgtaatac agggtcgtca gatacataga tacaattcta ttacccccat ccataca      1497
```

<210> SEQ ID NO 68
<211> LENGTH: 1011
<212> TYPE: DNA
<213> ORGANISM: Artificial Sequence
<220> FEATURE:
<223> OTHER INFORMATION: pACU14
<220> FEATURE:
<223> OTHER INFORMATION: pACU14

<400> SEQUENCE: 68

```
gctcagcatc tgcttcttcc caaagatgaa cgcggcgtta tgtcactaac gacgtgcacc     60
aacttgcggg aattggaaaa agacattttt gctgtcagtc actgtcaaga gattcttttg    120
ctggcatttc ttccagaagc aaaaagagcg atgcgtcttt tccgctgaac cgttccagca    180
aaaaagacta ccaacgaatt cgaaaaagac atttttgctg tcagtcactg tcaagagatt    240
cttttgctgg catttcttcc agaagcaaaa agagcgatgc gtcttttccg ctgaaccgtt    300
ccagcaaaaa agactaccaa cgaattcgaa aaagacattt ttgctgtcag tcactgtcaa    360
```

-continued

```
gagattcttt tgctggcatt tcttccagaa gcaaaaagag cgatgcgtct tttccgctga    420

accgttccag caaaaaagac taccaacgaa ttcgaaaaag acatttttgc tgtcagtcac    480

tgtcaagaga ttcttttgct ggcatttctt ccagaagcaa aaagagcgat gcgtcttttc    540

cgctgaaccg ttccagcaaa aaagactacc aaccaattcc accgcacgcc tttttctga     600

agcccacttt cgtggacttt gccatatatg caaaattcat gaagtgtgat accaagtcag    660

catacacctc actagggtag tttctttggt tgtattgatc atttggttca tcgtggttca    720

ttaatttttt ttctccattg ctttctggct ttgatcttac tatcatttgg atttttgtcg    780

aaggttgtag aattgtatgt gacaagtggc accaagcata tataaaaaaa aaaagcatta    840

tcttcctacc agagttgatt gttaaaaacg tatttatagc aaacgcaatt gtaattaatt    900

cttattttgt atcttttctt cccttgtctc aatcttttat ttttatttta tttttctttt    960

cttagtttct ttcataacac caagcaacta atactataac atacaataat a            1011
```

```
<210> SEQ ID NO 69
<211> LENGTH: 398
<212> TYPE: DNA
<213> ORGANISM: Artificial Sequence
<220> FEATURE:
<223> OTHER INFORMATION: pACU15
<220> FEATURE:
<223> OTHER INFORMATION: pACU15

<400> SEQUENCE: 69

tatagttttt tctccttgac gttaaagtat agaggtatat taacaatttt ttgttgatac     60

ttttatgaca tttgaataag aagtaataca aactgaaaat gttgaaagta ttagttaaag    120

tggttatgca gcttttccat ttatatatct gttaatagat caaaaatcat cgcttcgctg    180

attaattacc ccagaaataa ggctaaaaaa ctaatcgcat tatcatccga attcgttggt    240

agtctttttt gctggaacgg ttcagcggaa aagacgcatc gctctttttg cttctggaag    300

aaatgccagc aaaagaatct cttgacagtg actgacagca aaaatgtctt tttcgaattc    360

gggctcttta catttccaca acatataagt aagattag                            398
```

```
<210> SEQ ID NO 70
<211> LENGTH: 428
<212> TYPE: DNA
<213> ORGANISM: Artificial Sequence
<220> FEATURE:
<223> OTHER INFORMATION: pGAL/CUP1p
<220> FEATURE:
<223> OTHER INFORMATION: pGAL/CUP1p

<400> SEQUENCE: 70

ttatattgaa ttttcaaaaa ttcttacttt ttttttggat ggacgcaaag aagtttaata     60

atcatattac atggcattac caccatatac atatccatat ctaatcttac ttatatgttg    120

tggaaatgta aagagcccga attcgaaaaa gacatttttg ctgtcagtca ctgtcaagag    180

attcttttgc tggcatttct tccagaagca aaaagagcga tgcgtctttt ccgctgaacc    240

gttccagcaa aaaagactac caacgcaata tggattgtca gaatcatata aaagagaagc    300

aaataactcc ttgtcttgta tcaattgcat tataatatct tcttgttagt gcaatatcat    360

atagaagtca tcgaaataga tattaagaaa aacaaactgt acaatcaatc aatcaatcat    420

cacataaa                                                             428
```

```
<210> SEQ ID NO 71
<211> LENGTH: 518
```

<212> TYPE: DNA
<213> ORGANISM: Saccharomyces cerevisiae
<220> FEATURE:
<223> OTHER INFORMATION: pCRS5
<220> FEATURE:
<223> OTHER INFORMATION: pCRS5

<400> SEQUENCE: 71
gtggacgaaa agacataact gcagaagtac agctgccttt atttcttgtg gtcatttatt 60
gcttttattt tcaagtcaga tatacaagaa aatcaaatcc catcgtcaac gtcacgtata 120
aacgattaat ttacagtaat accatactct accaacatta ttttagtccg acgttcagtc 180
ctgtaggtgt tccaaatcct tctggcattg acttctgtgc agaaaccctt caaaatgagt 240
tccactttac gtcagatcgc ataacaaccg gtcatatatt tttttctttt gctaaacccc 300
ctactgcaag cacttttaag aaaaagaaca ataaatgcgt ctttattgct gtgtggaagt 360
gatttttgtc tttcggacaa aaaaaggata gggatgcgag agggctgtga agtagtgatc 420
aagcggggcc tatataagaa gggcgcacat cgtcccccct aagaatagcg aagcgatatt 480
acactgaaca ctacaatgtc aaatagtact caataaat 518

<210> SEQ ID NO 72
<211> LENGTH: 510
<212> TYPE: DNA
<213> ORGANISM: Saccharomyces cerevisiae
<220> FEATURE:
<223> OTHER INFORMATION: pCHA1
<220> FEATURE:
<223> OTHER INFORMATION: pCHA1

<400> SEQUENCE: 72
gatctctgct gacgttgtat ccacagatct aattgcaaga tagcctcttg cgaccttatt 60
aaaagcctct ccgtgatatc ctctagggct tgggttgcca ttaatcgatg tgtccttgtt 120
tccttatgcg agctgtttct tatctatctt atggtcccat tctttactgc actgtttaca 180
ttttgatcaa ttgcgaaatg ttcctactat ttttcttttt ctcttttcgc gagtactaat 240
caccgcgaac ggaaactaat gagtcctctg cgcggagaca tgattccgca tgggcggctc 300
ctgttaagcc ccagcggaaa tgtaattcca ctgagtgtca ttaaatagtg ccaaagcttt 360
atcaaattgt ttgcgatgag ataagataaa agggacaata tgaggaggaa cacaggtata 420
taaatatcgc caaataaaag gaaaatgttt atacagtttt ctctttttta agtgctggat 480
agacaagaga caggaaaatt aaccagcgag 510

<210> SEQ ID NO 73
<211> LENGTH: 601
<212> TYPE: DNA
<213> ORGANISM: Saccharomyces cerevisiae
<220> FEATURE:
<223> OTHER INFORMATION: pCTR1
<220> FEATURE:
<223> OTHER INFORMATION: pCTR1

<400> SEQUENCE: 73
caagtccgat tgttcctctt caggagcttc ctgaaccaaa ctttttccgc aaggccgcat 60
tttgaaccgt attttgctcg ttccagcctt tccacgtttt tgttatctaa gcaacttggc 120
acatttccct actatactac aaaccgatac gtaaatactt ccctaaatag catatgaatt 180
attcagtaat ttttaaggat cgaaactgca cctcaactat tcgttactgt ggttatgttc 240
tcatgtattg atgcaaatca tgggatattt gctcaagacg acggtaaaat gagcaaaaat 300
ggcacgatcc tgaaaagagc acttttcaag attcgggcta caaaatgcaa cataaaaaat 360
gttgtattgt catctcgaca gggtcttgta tgttttattc ctcttatgat tagttcacat 420
tagtaaaaca gatacgcagt gtgctcttaa taaacaacta ctccatagct ttatttgcat 480
aacaaaactt ttaagcacaa acttaaacag gtggagtaat agttcggcgg cgactcaaat 540
tacatttgtt ggaagaatcg aatagaaaat aaaaaaaagt gtattatatt tgacattcaa 600
a 601

<210> SEQ ID NO 74
<211> LENGTH: 522
<212> TYPE: DNA
<213> ORGANISM: Saccharomyces cerevisiae
<220> FEATURE:
<223> OTHER INFORMATION: pCTR3
<220> FEATURE:
<223> OTHER INFORMATION: pCTR3

<400> SEQUENCE: 74
gatgtgatga caaaacctct tccgataaaa acatttaaac tattaacaaa caaatggatt 60
cattagatct attacattat gggtggtatg ttggaataaa aatcaactat catctactaa 120
ctagtattta cgttactagt atattatcat atacggtgtt agaagatgac gcaaatgatg 180
agaaatagtc atctaaatta gtggaagctg aaacgcaagg attgataatg taataggatc 240
aatgaatatt aacatataaa acgatgataa taatatttat agaattgtgt agaattgcag 300
attccctttt atggattcct aaatcctcca ggagaacttc tagtatatct acatacctaa 360
tattattgcc ttattaaaaa tggaatccca acaattacat caaaatccac attctcttca 420
cttctccgat agacttgtaa tttatcttat ttcatttcct aacactttga tcgaagaaga 480
gggataacaa cagacgaaaa cacatttaag ggctatacaa ag 522

<210> SEQ ID NO 75
<211> LENGTH: 675
<212> TYPE: DNA
<213> ORGANISM: Artificial Sequence
<220> FEATURE:
<223> OTHER INFORMATION: pCUR1
<220> FEATURE:
<223> OTHER INFORMATION: pCUR1

<400> SEQUENCE: 75
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgtcatggga tatttgctca agacgacggt aaaatgagca aatatggcac gatcctcaat 420
tctaattaag ttagtcaagg cgccatcctc atgaaaactg tgtaacataa taaccgaagt 480
gtcgaaaagg tggcaccttg tccaattgaa cacgctcgat gaaaaaaata agatatatat 540
aaggttaagt aaagcgtctg ttagaaagga agtttttcct ttttcttgct ctcttgtctt 600
ttcatctact atttccttcg tgtaatacag ggtcgtcaga tacatagata caattctatt 660
acccccatcc ataca 675

<210> SEQ ID NO 76
<211> LENGTH: 674
<212> TYPE: DNA
<213> ORGANISM: Artificial Sequence
<220> FEATURE:
<223> OTHER INFORMATION: pCUR2
<220> FEATURE:
<223> OTHER INFORMATION: pCUR2

<400> SEQUENCE: 76
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgatt 360
gaggatcgtg ccatatttgc tcattttacc gtcgtcttga gcaaatatcc catgacaatt 420
ctaattaagt tagtcaaggc gccatcctca tgaaaactgt gtaacataat aaccgaagtg 480
tcgaaaaggt ggcaccttgt ccaattgaac acgctcgatg aaaaaaataa gatatatata 540
aggttaagta aagcgtctgt tagaaaggaa gtttttcctt tttcttgctc tcttgtcttt 600
tcatctacta tttccttcgt gtaatacagg gtcgtcagat acatagatac aattctatta 660
cccccatcca taca 674

<210> SEQ ID NO 77
<211> LENGTH: 794
<212> TYPE: DNA
<213> ORGANISM: Artificial Sequence
<220> FEATURE:
<223> OTHER INFORMATION: pCUR3
<220> FEATURE:
<223> OTHER INFORMATION: pCUR3

<400> SEQUENCE: 77
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
taggatcgtg ccatatttgc tcattttacc gtcgtcttga gcaaatatcc catgacaatt 420
gaggatcgtg ccatatttgc tcattttacc gtcgtcttga gcaaatatcc catgacaatt 480
gaggatcgtg ccatatttgc tcattttacc gtcgtcttga gcaaatatcc catgacaatt 540
ctaattaagt tagtcaaggc gccatcctca tgaaaactgt gtaacataat aaccgaagtg 600
tcgaaaaggt ggcaccttgt ccaattgaac acgctcgatg aaaaaaataa gatatatata 660
aggttaagta aagcgtctgt tagaaaggaa gtttttcctt tttcttgctc tcttgtcttt 720
tcatctacta tttccttcgt gtaatacagg gtcgtcagat acatagatac aattctatta 780
cccccatcca taca 794

<210> SEQ ID NO 78
<211> LENGTH: 850
<212> TYPE: DNA

<213> ORGANISM: Artificial Sequence
<220> FEATURE:
<223> OTHER INFORMATION: pCUR4
<220> FEATURE:
<223> OTHER INFORMATION: pCUR4

<400> SEQUENCE: 78
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgtcatggga tatttgctca agacgacggt aaaatgagca aatatggcac gatcctcaat 420
tgtcatggga tatttgctca agacgacggt aaaatgagca aatatggcac gatcctcaat 480
gtcatgggat atttgctcaa gacgacggta aaatgagcaa atatggcacg atcctcaatt 540
gtcatgggat atttgctcaa gacgacggta aaatgagcaa atatcccatg acaattctaa 600
ttaagttagt caaggcgcca tcctcatgaa aactgtgtaa cataataacc gaagtgtcga 660
aaaggtggca ccttgtccaa ttgaacacgc tcgatgaaaa aaataagata tatataaggt 720
taagtaaagc gtctgttaga aaggaagttt ttccttttttc ttgctctctt gtcttttcat 780
ctactatttc cttcgtgtaa tacagggtcg tcagatacat agatacaatt ctattacccc 840
catccataca 850

<210> SEQ ID NO 79
<211> LENGTH: 491
<212> TYPE: DNA
<213> ORGANISM: Artificial Sequence
<220> FEATURE:
<223> OTHER INFORMATION: pCUR5p
<220> FEATURE:
<223> OTHER INFORMATION: pCUR5p

<400> SEQUENCE: 79
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attgtcatgg gatatttgct caagacgacg gtaaaatgag 180
caaatatggc acgatcctca attgtcatgg gatatttgct caagacgacg gtaaaatgag 240
caaatatggc acgatcccaa ttcggatgat aatgcgatta gttttttagc cttatttctg 300
gggtaattaa tcagcgaagc gatgattttt gatctattaa cagatatata aatggaaaag 360
ctgcataacc actttaacta atactttcaa cattttcagt ttgtattact tcttattcaa 420
atgtcataaa agtatcaaca aaaaattgtt aatatacctc tatactttaa cgtcaaggag 480
aaaaaactat a 491

<210> SEQ ID NO 80
<211> LENGTH: 833
<212> TYPE: DNA
<213> ORGANISM: Artificial Sequence
<220> FEATURE:
<223> OTHER INFORMATION: pCUR6
<220> FEATURE:
<223> OTHER INFORMATION: pCUR6

<400> SEQUENCE: 80

```
ttacattatc aatccttgcg tttcagcttc cactaattta gatgactatt tctcatcatt     60

tgcgtcatct tctaacaccg tatatgataa tatactagta acgtaaatac tagttagtag    120

atgatagttg atttttattc caacactaag aaataatttc gccatttctt gaatgtattt    180

aaagatattt aatgctataa tagacattta aatccaattc ttccaacata caatgggagt    240

ttggccgagt ggtttaaggc gtcagattta ggtggattta acctctaaaa tctctgatat    300

cttcggatgc aagggttcga atcccgaatt gaggatcgtg ccatatttgc tcattttacc    360

gtcgtcttga gcaaatatcc catgacaatt gaggatcgtg ccatatttgc tcattttacc    420

gtcgtcttga gcaaatatcc catgacaatt gaggatcgtg ccatatttgc tcattttacc    480

gtcgtcttga gcaaatatcc catgacaatt catgatcgca aaatggcaaa tggcacgtga    540

agctgtcgat attggggaac tgtggtggtt ggcaaatgac taattaagtt agtcaaggcg    600

ccatcctcat gaaaactgtg taacataata accgaagtgt cgaaaaggtg gcaccttgtc    660

caattgaaca cgctcgatga aaaaaataag atatatataa ggttaagtaa agcgtctgtt    720

agaaaggaag tttttccttt ttcttgctct cttgtctttt catctactat ttccttcgtg    780

taatacaggg tcgtcagata catagataca attctattac ccccatccat aca           833
```

<210> SEQ ID NO 81
<211> LENGTH: 803
<212> TYPE: DNA
<213> ORGANISM: Artificial Sequence
<220> FEATURE:
<223> OTHER INFORMATION: pCUR7
<220> FEATURE:
<223> OTHER INFORMATION: pCUR7

<400> SEQUENCE: 81

```
gtgagtaagg aaagagtgag gaactatcgc atacctgcat ttaaagatgc cgatttgggc     60

gcgaatcctt tattttggct tcaccctcat actattatca gggccagaaa aaggaagtgt    120

ttccctcctt cttgaattga tgttaccctc ataaagcacg tggcctctta tcgagaaaga    180

aattaccgtc gctcgtgatt tgtttgcaaa aagaacaaaa ctgaattcag gatcgtgcca    240

tatttgctca ttttaccgtc gtcttgagca aatatcccat gacaattgag gatcgtgcca    300

tatttgctca ttttaccgtc gtcttgagca aatatcccat gagaattctt cctgtcttcc    360

tattgattgc agcttccaat ttcgtcacac aacaaggtcc tagcgacggc tcacaggttt    420

tgtaacaagc aatcgaaggt tctggaatgg cgggaaaggg tttagtacca catgctatga    480

tgcccactgt gatctccaga gcaaagttcg ttcgatcgta ctgttactct ctctctttca    540

aacagaattg tccgaatcgt gtgacaacaa cagcctgttc tcacacactc ttttcttcta    600

accaaggggg tggtttagtt tagtagaacc tcgtgaaact tacatttaca tatatataaa    660

cttgcataaa ttggtcaatg caagaaatac atatttggtc ttttctaatt cgtagttttt    720

caagttctta gatgctttct ttttctcttt tttacagatc atcaaggaag taattatcta    780

ctttttacaa caaatataaa aca                                            803
```

<210> SEQ ID NO 82
<211> LENGTH: 863
<212> TYPE: DNA
<213> ORGANISM: Artificial Sequence
<220> FEATURE:
<223> OTHER INFORMATION: pCUR8
<220> FEATURE:
<223> OTHER INFORMATION: pCUR8

<400> SEQUENCE: 82
gtgagtaagg aaagagtgag gaactatcgc atacctgcat ttaaagatgc cgatttgggc 60
gcgaatcctt tattttggct tcaccctcat actattatca gggccagaaa aaggaagtgt 120
ttccctcctt cttgaattga tgttaccctc ataaagcacg tggcctctta tcgagaaaga 180
aattaccgtc gctcgtgatt tgtttgcaaa aagaacaaaa ctgaattcag gatcgtgcca 240
tatttgctca ttttaccgtc gtcttgagca aatatcccat gacaattgag gatcgtgcca 300
tatttgctca ttttaccgtc gtcttgagca aatatcccat gacaattgag gatcgtgcca 360
tatttgctca ttttaccgtc gtcttgagca aatatcccat gagaattctt cctgtcttcc 420
tattgattgc agcttccaat ttcgtcacac aacaaggtcc tagcgacggc tcacaggttt 480
tgtaacaagc aatcgaaggt tctggaatgg cgggaaaggg tttagtacca catgctatga 540
tgcccactgt gatctccaga gcaaagttcg ttcgatcgta ctgttactct ctctctttca 600
aacagaattg tccgaatcgt gtgacaacaa cagcctgttc tcacacactc ttttcttcta 660
accaaggggg tggtttagtt tagtagaacc tcgtgaaact tacatttaca tatatataaa 720
cttgcataaa ttggtcaatg caagaaatac atatttggtc ttttctaatt cgtagttttt 780
caagttctta gatgctttct ttttctcttt tttacagatc atcaaggaag taattatcta 840
ctttttacaa caaatataaa aca 863

<210> SEQ ID NO 83
<211> LENGTH: 863
<212> TYPE: DNA
<213> ORGANISM: Artificial Sequence
<220> FEATURE:
<223> OTHER INFORMATION: pCUR9
<220> FEATURE:
<223> OTHER INFORMATION: pCUR9

<400> SEQUENCE: 83
gtgagtaagg aaagagtgag gaactatcgc atacctgcat ttaaagatgc cgatttgggc 60
gcgaatcctt tattttggct tcaccctcat actattatca gggccagaaa aaggaagtgt 120
ttccctcctt cttgaattga tgttaccctc ataaagcacg tggcctctta tcgagaaaga 180
aattaccgtc gctcgtgatt tgtttgcaaa aagaacaaaa ctgaattctc atgggatatt 240
tgctcaagac gacggtaaaa tgagcaaata tggcacgatc ctcaattgtc atgggatatt 300
tgctcaagac gacggtaaaa tgagcaaata tggcacgatc ctcaattgtc atgggatatt 360
tgctcaagac gacggtaaaa tgagcaaata tggcacgatc ctgaattctt cctgtcttcc 420
tattgattgc agcttccaat ttcgtcacac aacaaggtcc tagcgacggc tcacaggttt 480
tgtaacaagc aatcgaaggt tctggaatgg cgggaaaggg tttagtacca catgctatga 540
tgcccactgt gatctccaga gcaaagttcg ttcgatcgta ctgttactct ctctctttca 600
aacagaattg tccgaatcgt gtgacaacaa cagcctgttc tcacacactc ttttcttcta 660
accaaggggg tggtttagtt tagtagaacc tcgtgaaact tacatttaca tatatataaa 720
cttgcataaa ttggtcaatg caagaaatac atatttggtc ttttctaatt cgtagttttt 780
caagttctta gatgctttct ttttctcttt tttacagatc atcaaggaag taattatcta 840
ctttttacaa caaatataaa aca 863

<210> SEQ ID NO 84
<211> LENGTH: 923
<212> TYPE: DNA
<213> ORGANISM: Artificial Sequence -continued
<220> FEATURE:
<223> OTHER INFORMATION: pCUR10
<220> FEATURE:
<223> OTHER INFORMATION: pCUR10

<400> SEQUENCE: 84

```
gtgagtaagg aaagagtgag gaactatcgc atacctgcat ttaaagatgc cgatttgggc     60

gcgaatcctt tattttggct tcaccctcat actattatca gggccagaaa aaggaagtgt    120

ttccctcctt cttgaattga tgttaccctc ataaagcacg tggcctctta tcgagaaaga    180

aattaccgtc gctcgtgatt tgtttgcaaa aagaacaaaa ctgaattctc atgggatatt    240

tgctcaagac gacggtaaaa tgagcaaata tggcacgatc ctcaattgtc atgggatatt    300

tgctcaagac gacggtaaaa tgagcaaata tggcacgatc ctcaattgtc atgggatatt    360

tgctcaagac gacggtaaaa tgagcaaata tggcacgatc ctcaattgtc atgggatatt    420

tgctcaagac gacggtaaaa tgagcaaata tggcacgatc ctgaattctt cctgtcttcc    480

tattgattgc agcttccaat ttcgtcacac aacaaggtcc tagcgacggc tcacaggttt    540

tgtaacaagc aatcgaaggt tctggaatgg cgggaaaggg tttagtacca catgctatga    600

tgcccactgt gatctccaga gcaaagttcg ttcgatcgta ctgttactct ctctctttca    660

aacagaattg tccgaatcgt gtgacaacaa cagcctgttc tcacacactc ttttcttcta    720

accaaggggg tggtttagtt tagtagaacc tcgtgaaact tacatttaca tatatataaa    780

cttgcataaa ttggtcaatg caagaaatac atatttggtc ttttctaatt cgtagttttt    840

caagttctta gatgctttct ttttctcttt tttacagatc atcaaggaag taattatcta    900

ctttttacaa caaatataaa aca                                            923
```

<210> SEQ ID NO 85
<211> LENGTH: 983
<212> TYPE: DNA
<213> ORGANISM: Artificial Sequence
<220> FEATURE:
<223> OTHER INFORMATION: pCUR11
<220> FEATURE:
<223> OTHER INFORMATION: pCUR11

<400> SEQUENCE: 85

```
gtgagtaagg aaagagtgag gaactatcgc atacctgcat ttaaagatgc cgatttgggc     60

gcgaatcctt tattttggct tcaccctcat actattatca gggccagaaa aaggaagtgt    120

ttccctcctt cttgaattga tgttaccctc ataaagcacg tggcctctta tcgagaaaga    180

aattaccgtc gctcgtgatt tgtttgcaaa aagaacaaaa ctgaattctc atgggatatt    240

tgctcaagac gacggtaaaa tgagcaaata tggcacgatc ctcaattgtc atgggatatt    300

tgctcaagac gacggtaaaa tgagcaaata tggcacgatc ctcaattgtc atgggatatt    360

tgctcaagac gacggtaaaa tgagcaaata tggcacgatc ctcaattgtc atgggatatt    420

tgctcaagac gacggtaaaa tgagcaaata tggcacgatc ctcaattgtc atgggatatt    480

tgctcaagac gacggtaaaa tgagcaaata tggcacgatc ctgaattctt cctgtcttcc    540

tattgattgc agcttccaat ttcgtcacac aacaaggtcc tagcgacggc tcacaggttt    600

tgtaacaagc aatcgaaggt tctggaatgg cgggaaaggg tttagtacca catgctatga    660

tgcccactgt gatctccaga gcaaagttcg ttcgatcgta ctgttactct ctctctttca    720

aacagaattg tccgaatcgt gtgacaacaa cagcctgttc tcacacactc ttttcttcta    780

accaaggggg tggtttagtt tagtagaacc tcgtgaaact tacatttaca tatatataaa    840
```

cttgcataaa ttggtcaatg caagaaatac atatttggtc ttttctaatt cgtagttttt 900
caagttctta gatgctttct ttttctcttt tttacagatc atcaaggaag taattatcta 960
ctttttacaa caaatataaa aca 983

<210> SEQ ID NO 86
<211> LENGTH: 1043
<212> TYPE: DNA
<213> ORGANISM: Artificial Sequence
<220> FEATURE:
<223> OTHER INFORMATION: pCUR12
<220> FEATURE:
<223> OTHER INFORMATION: pCUR12

<400> SEQUENCE: 86
gtgagtaagg aaagagtgag gaactatcgc atacctgcat ttaaagatgc cgatttgggc 60
gcgaatcctt tattttggct tcaccctcat actattatca gggccagaaa aaggaagtgt 120
ttccctcctt cttgaattga tgttaccctc ataaagcacg tggcctctta tcgagaaaga 180
aattaccgtc gctcgtgatt tgtttgcaaa aagaacaaaa ctgaattcag gatcgtgcca 240
tatttgctca ttttaccgtc gtcttgagca aatatcccat gacaattgag gatcgtgcca 300
tatttgctca ttttaccgtc gtcttgagca aatatcccat gacaattgag gatcgtgcca 360
tatttgctca ttttaccgtc gtcttgagca aatatcccat gagaattcag gatcgtgcca 420
tatttgctca ttttaccgtc gtcttgagca aatatcccat gacaattgag gatcgtgcca 480
tatttgctca ttttaccgtc gtcttgagca aatatcccat gacaattgag gatcgtgcca 540
tatttgctca ttttaccgtc gtcttgagca aatatcccat gagaattctt cctgtcttcc 600
tattgattgc agcttccaat ttcgtcacac aacaaggtcc tagcgacggc tcacaggttt 660
tgtaacaagc aatcgaaggt tctggaatgg cgggaaaggg tttagtacca catgctatga 720
tgcccactgt gatctccaga gcaaagttcg ttcgatcgta ctgttactct ctctctttca 780
aacagaattg tccgaatcgt gtgacaacaa cagcctgttc tcacacactc ttttcttcta 840
accaaggggg tggtttagtt tagtagaacc tcgtgaaact tacatttaca tatatataaa 900
cttgcataaa ttggtcaatg caagaaatac atatttggtc ttttctaatt cgtagttttt 960
caagttctta gatgctttct ttttctcttt tttacagatc atcaaggaag taattatcta 1020
ctttttacaa caaatataaa aca 1043

<210> SEQ ID NO 87
<211> LENGTH: 1043
<212> TYPE: DNA
<213> ORGANISM: Artificial Sequence
<220> FEATURE:
<223> OTHER INFORMATION: pCUR13
<220> FEATURE:
<223> OTHER INFORMATION: pCUR13

<400> SEQUENCE: 87
gtgagtaagg aaagagtgag gaactatcgc atacctgcat ttaaagatgc cgatttgggc 60
gcgaatcctt tattttggct tcaccctcat actattatca gggccagaaa aaggaagtgt 120
ttccctcctt cttgaattga tgttaccctc ataaagcacg tggcctctta tcgagaaaga 180
aattaccgtc gctcgtgatt tgtttgcaaa aagaacaaaa ctgaattctc atgggatatt 240
tgctcaagac gacggtaaaa tgagcaaata tggcacgatc ctcaattgtc atgggatatt 300
tgctcaagac gacggtaaaa tgagcaaata tggcacgatc ctcaattgtc atgggatatt 360
tgctcaagac gacggtaaaa tgagcaaata tggcacgatc ctgaattctc atgggatatt 420

```
tgctcaagac gacggtaaaa tgagcaaata tggcacgatc ctcaattgtc atgggatatt    480

tgctcaagac gacggtaaaa tgagcaaata tggcacgatc ctcaattgtc atgggatatt    540

tgctcaagac gacggtaaaa tgagcaaata tggcacgatc ctgaattctt cctgtcttcc    600

tattgattgc agcttccaat ttcgtcacac aacaaggtcc tagcgacggc tcacaggttt    660

tgtaacaagc aatcgaaggt tctggaatgg cgggaaaggg tttagtacca catgctatga    720

tgcccactgt gatctccaga gcaaagttcg ttcgatcgta ctgttactct ctctctttca    780

aacagaattg tccgaatcgt gtgacaacaa cagcctgttc tcacacactc ttttcttcta    840

accaaggggg tggtttagtt tagtagaacc tcgtgaaact tacatttaca tatatataaa    900

cttgcataaa ttggtcaatg caagaaatac atatttggtc ttttctaatt cgtagttttt    960

caagttctta gatgctttct ttttctcttt tttacagatc atcaaggaag taattatcta   1020

ctttttacaa caaatataaa aca                                           1043
```

<210> SEQ ID NO 88
<211> LENGTH: 1223
<212> TYPE: DNA
<213> ORGANISM: Artificial Sequence
<220> FEATURE:
<223> OTHER INFORMATION: pCUR14
<220> FEATURE:
<223> OTHER INFORMATION: pCUR14

<400> SEQUENCE: 88

```
gtgagtaagg aaagagtgag gaactatcgc atacctgcat ttaaagatgc cgatttgggc     60

gcgaatcctt tattttggct tcaccctcat actattatca gggccagaaa aaggaagtgt    120

ttccctcctt cttgaattga tgttaccctc ataaagcacg tggcctctta tcgagaaaga    180

aattaccgtc gctcgtgatt tgtttgcaaa aagaacaaaa ctgaattctc atgggatatt    240

tgctcaagac gacggtaaaa tgagcaaata tggcacgatc ctcaattgtc atgggatatt    300

tgctcaagac gacggtaaaa tgagcaaata tggcacgatc ctcaattgtc atgggatatt    360

tgctcaagac gacggtaaaa tgagcaaata tggcacgatc ctgaattctc atgggatatt    420

tgctcaagac gacggtaaaa tgagcaaata tggcacgatc ctcaattgtc atgggatatt    480

tgctcaagac gacggtaaaa tgagcaaata tggcacgatc ctcaattgtc atgggatatt    540

tgctcaagac gacggtaaaa tgagcaaata tggcacgatc ctgaattctc atgggatatt    600

tgctcaagac gacggtaaaa tgagcaaata tggcacgatc ctcaattgtc atgggatatt    660

tgctcaagac gacggtaaaa tgagcaaata tggcacgatc ctcaattgtc atgggatatt    720

tgctcaagac gacggtaaaa tgagcaaata tggcacgatc ctgaattctt cctgtcttcc    780

tattgattgc agcttccaat ttcgtcacac aacaaggtcc tagcgacggc tcacaggttt    840

tgtaacaagc aatcgaaggt tctggaatgg cgggaaaggg tttagtacca catgctatga    900

tgcccactgt gatctccaga gcaaagttcg ttcgatcgta ctgttactct ctctctttca    960

aacagaattg tccgaatcgt gtgacaacaa cagcctgttc tcacacactc ttttcttcta   1020

accaaggggg tggtttagtt tagtagaacc tcgtgaaact tacatttaca tatatataaa   1080

cttgcataaa ttggtcaatg caagaaatac atatttggtc ttttctaatt cgtagttttt   1140

caagttctta gatgctttct ttttctcttt tttacagatc atcaaggaag taattatcta   1200

ctttttacaa caaatataaa aca                                           1223
```

<210> SEQ ID NO 89

<211> LENGTH: 1283
<212> TYPE: DNA
<213> ORGANISM: Artificial Sequence
<220> FEATURE:
<223> OTHER INFORMATION: pCUR15
<220> FEATURE:
<223> OTHER INFORMATION: pCUR15

<400> SEQUENCE: 89

```
gtgagtaagg aaagagtgag gaactatcgc atacctgcat ttaaagatgc cgatttgggc     60

gcgaatcctt tattttggct tcaccctcat actattatca gggccagaaa aaggaagtgt    120

ttccctcctt cttgaattga tgttaccctc ataaagcacg tggcctctta tcgagaaaga    180

aattaccgtc gctcgtgatt tgtttgcaaa aagaacaaaa ctgaattcag gatcgtgcca    240

tatttgctca ttttaccgtc gtcttgagca aatatcccat gacaattgag gatcgtgcca    300

tatttgctca ttttaccgtc gtcttgagca aatatcccat gacaattgag gatcgtgcca    360

tatttgctca ttttaccgtc gtcttgagca aatatcccat gacaattgag gatcgtgcca    420

tatttgctca ttttaccgtc gtcttgagca aatatcccat gagaattcag gatcgtgcca    480

tatttgctca ttttaccgtc gtcttgagca aatatcccat gacaattgag gatcgtgcca    540

tatttgctca ttttaccgtc gtcttgagca aatatcccat gacaattgag gatcgtgcca    600

tatttgctca ttttaccgtc gtcttgagca aatatcccat gagaattcag gatcgtgcca    660

tatttgctca ttttaccgtc gtcttgagca aatatcccat gacaattgag gatcgtgcca    720

tatttgctca ttttaccgtc gtcttgagca aatatcccat gacaattgag gatcgtgcca    780

tatttgctca ttttaccgtc gtcttgagca aatatcccat gagaattctt cctgtcttcc    840

tattgattgc agcttccaat ttcgtcacac aacaaggtcc tagcgacggc tcacaggttt    900

tgtaacaagc aatcgaaggt tctggaatgg cgggaaaggg tttagtacca catgctatga    960

tgcccactgt gatctccaga gcaaagttcg ttcgatcgta ctgttactct ctctctttca   1020

aacagaattg tccgaatcgt gtgacaacaa cagcctgttc tcacacactc ttttcttcta   1080

accaaggggg tggtttagtt tagtagaacc tcgtgaaact tacatttaca tatatataaa   1140

cttgcataaa ttggtcaatg caagaaatac atatttggtc ttttctaatt cgtagttttt   1200

caagttctta gatgctttct ttttctcttt tttacagatc atcaaggaag taattatcta   1260

ctttttacaa caaatataaa aca                                            1283
```

<210> SEQ ID NO 90
<211> LENGTH: 686
<212> TYPE: DNA
<213> ORGANISM: Artificial Sequence
<220> FEATURE:
<223> OTHER INFORMATION: pCUR16
<220> FEATURE:
<223> OTHER INFORMATION: pCUR16

<400> SEQUENCE: 90

```
gctcagcatc tgcttcttcc caaagatgaa cgcggcgtta tgtcactaac gacgtgcacc     60

aacttgcggg aattctcatg ggatatttgc tcaagacgac ggtaaaatga gcaaatatgg    120

cacgatcctc aattgtcatg ggatatttgc tcaagacgac ggtaaaatga gcaaatatgg    180

cacgatcctc aatgtcatgg gatatttgct caagacgacg gtaaaatgag caaatatggc    240

acgatcctga attccaccgc acgccttttt tctgaagccc actttcgtgg actttgccat    300

atatgcaaaa ttcatgaagt gtgataccaa gtcagcatac acctcactag ggtagtttct    360

ttggttgtat tgatcatttg gttcatcgtg gttcattaat tttttttctc cattgctttc    420
```

```
tggctttgat cttactatca tttggatttt tgtcgaaggt tgtagaattg tatgtgacaa    480

gtggcaccaa gcatatataa aaaaaaaaag cattatcttc ctaccagagt tgattgttaa    540

aaacgtattt atagcaaacg caattgtaat taattcttat tttgtatctt ttcttccctt    600

gtctcaatct tttattttta ttttattttt cttttcttag tttctttcat aacaccaagc    660

aactaatact ataacataca ataata                                         686
```

<210> SEQ ID NO 91
<211> LENGTH: 747
<212> TYPE: DNA
<213> ORGANISM: Artificial Sequence
<220> FEATURE:
<223> OTHER INFORMATION: pCUR17
<220> FEATURE:
<223> OTHER INFORMATION: pCUR17

<400> SEQUENCE: 91

```
gctcagcatc tgcttcttcc caaagatgaa cgcggcgtta tgtcactaac gacgtgcacc     60

aacttgcggg aattctcatg ggatatttgc tcaagacgac ggtaaaatga gcaaatatgg    120

cacgatcctc aattgtcatg ggatatttgc tcaagacgac ggtaaaatga gcaaatatgg    180

cacgatcctc aattctcatg ggatatttgc tcaagacgac ggtaaaatga gcaaatatgg    240

cacgatcctc aattctcatg ggatatttgc tcaagacgac ggtaaaatga gcaaatatgg    300

cacgatcctg aattccaccg cacgcctttt ttctgaagcc cactttcgtg gactttgcca    360

tatatgcaaa attcatgaag tgtgatacca agtcagcata cacctcacta gggtagtttc    420

tttggttgta ttgatcattt ggttcatcgt ggttcattaa ttttttttct ccattgcttt    480

ctggctttga tcttactatc atttggattt ttgtcgaagg ttgtagaatt gtatgtgaca    540

agtggcacca agcatatata aaaaaaaaaa gcattatctt cctaccagag ttgattgtta    600

aaaacgtatt tatagcaaac gcaattgtaa ttaattctta ttttgtatct tttcttccct    660

tgtctcaatc ttttattttt attttatttt tcttttctta gtttctttca taacaccaag    720

caactaatac tataacatac aataata                                        747
```

<210> SEQ ID NO 92
<211> LENGTH: 500
<212> TYPE: DNA
<213> ORGANISM: Saccharomyces cerevisiae
<220> FEATURE:
<223> OTHER INFORMATION: pLYS1
<220> FEATURE:
<223> OTHER INFORMATION: pLYS1

<400> SEQUENCE: 92

```
gcaagttaac attagggaga acgtggggcc ttcctccatg agtgcagagc aattgaagat     60

gtttagaggt ttaaaggaga ataaccagtt gctggatagc tctgtgccag ctacagttta    120

tgccaaattg gcccttcatg gtattcctga cggtgttaat ggacagtact tgagctataa    180

tgaccctgcc ttggcggact ttatgccttg aggatagcag gtacatataa attgttacat    240

actaagtcga tgagtcaaaa aagactctta tacatttata cattttgcat tattattttt    300

tttttccagc ggaatttgga attccgctct caaccgccaa aattcccctg cgatttcagc    360

gacaaagagt cataaagtca tcctcgagaa accacgatga aatatataaa aagcccatct    420

tccctgacgg aaactggtat tttaggaggc ataccataag ataacaacga aaacgcttta    480

tttttcacac aaccgcaaaa                                                500
```

<210> SEQ ID NO 93
<211> LENGTH: 650
<212> TYPE: DNA
<213> ORGANISM: Saccharomyces cerevisiae
<220> FEATURE:
<223> OTHER INFORMATION: pLYS4
<220> FEATURE:
<223> OTHER INFORMATION: pLYS4

<400> SEQUENCE: 93
ttgaaaaatg cgaagttgaa gtgccataga agagaaacag cccacacagg ggagaagccc 60
actggaaagg gggcactgac caactttaaa taggaaacag aagataccac aagccagcga 120
tacaacagca ccaaacaccg aaaagaatag ccaaagctgt cctctggtgt tggaaaaact 180
ggaaaaaacg caactgcgtt ggctgctacg gtgaaaaatt ttcctatgac ttttttcact 240
gcttgttcgt gcgaaattac cgcaaacccg gtaaaatgta cacgtatcaa gtgataaaca 300
atttcgtgtc aagtgagcag aatggagcga tttggaaaaa aaaaattttt attgtttttt 360
cccccgggat tttgctcgag atgactgaaa ttttgtaatc gatgagtcta taccagaggc 420
agcaaatatc accaacatac acaggtatac acaatctcat gtccacacac acgtacagac 480
acgcacatat atatatatat atatatatcc ccataggtat ttatatatac aaaagaatcc 540
tcgtgtgttt gtgtgtgcaa tagctagttt tgcgctgcct cttatagtag acaatatcac 600
tttttcaata aaatagaact tgcaaggaaa caaaattgta tcgcttcaag 650

<210> SEQ ID NO 94
<211> LENGTH: 500
<212> TYPE: DNA
<213> ORGANISM: Saccharomyces cerevisiae
<220> FEATURE:
<223> OTHER INFORMATION: pLYS9
<220> FEATURE:
<223> OTHER INFORMATION: pLYS9

<400> SEQUENCE: 94
acatatgcaa gagtcttatg tatcgtatct aagtgccacg taggggattc ccatcatttg 60
atgatttcca aatataatac ctgtagagag cggtggagca aaagtcaaat tttaatcgca 120
actgcagaca agtcaagctg aggaaattgt ggatgatctc ttgtttcttt tgatattcac 180
cacaacagaa gtgaagagtg tgattgcggt tactactgac cacgaagcaa tgcgtttagt 240
agtgaaaaga attactcata ctctggaatc gaaattccgt tggaaaaatt cgctttgtag 300
tgaaaaataa agatgtcaat aaagggtatt gagaatttcc aatggaatta tcagcaatag 360
atgatagaaa gtagcacaga atttggctta atggtatata aaccgtaggg tcctggtaaa 420
attacatggg aaggatcctt aggcagtagg gaaaacttat caggacaatt gagttatatt 480
aacgtattat atattttaat 500

<210> SEQ ID NO 95
<211> LENGTH: 494
<212> TYPE: DNA
<213> ORGANISM: Artificial Sequence
<220> FEATURE:
<223> OTHER INFORMATION: pLYR1p
<220> FEATURE:
<223> OTHER INFORMATION: pLYR1p

<400> SEQUENCE: 95
ttatattgaa ttttcaaaaa ttcttacttt ttttttggat ggacgcaaag aagtttaata 60
atcatattac atggcattac caccatatac atatccatat ctaatcttac ttatatgttg 120

```
tggaaatgta aagagcccga attcctcata ctctggaatc gaaattccgt tggaaaaatt    180

cgctttgtag tgaaaaataa agatgtcaat aaagggtatt gagaatttcc aatggaatta    240

tcagcaatag atgatagaaa gaattcggat gataatgcga ttagtttttt agccttattt    300

ctggggtaat taatcagcga agcgatgatt tttgatctat taacagatat ataaatggaa    360

aagctgcata accactttaa ctaatacttt caacattttc agtttgtatt acttcttatt    420

caaatgtcat aaaagtatca acaaaaaatt gttaatatac ctctatactt taacgtcaag    480

gagaaaaaac tata                                                      494
```

<210> SEQ ID NO 96
<211> LENGTH: 494
<212> TYPE: DNA
<213> ORGANISM: Artificial Sequence
<220> FEATURE:
<223> OTHER INFORMATION: pLYR2p
<220> FEATURE:
<223> OTHER INFORMATION: pLYR2p

<400> SEQUENCE: 96

```
ttatattgaa ttttcaaaaa ttcttacttt ttttttggat ggacgcaaag aagtttaata     60

atcatattac atggcattac caccatatac atatccatat ctaatcttac ttatatgttg    120

tggaaatgta aagagcccga attctttcta tcatctattg ctgataattc cattggaaat    180

tctcaatacc ctttattgac atctttattt ttcactacaa agcgaatttt tccaacggaa    240

tttcgattcc agagtatgag gaattcggat gataatgcga ttagtttttt agccttattt    300

ctggggtaat taatcagcga agcgatgatt tttgatctat taacagatat ataaatggaa    360

aagctgcata accactttaa ctaatacttt caacattttc agtttgtatt acttcttatt    420

caaatgtcat aaaagtatca acaaaaaatt gttaatatac ctctatactt taacgtcaag    480

gagaaaaaac tata                                                      494
```

<210> SEQ ID NO 97
<211> LENGTH: 616
<212> TYPE: DNA
<213> ORGANISM: Artificial Sequence
<220> FEATURE:
<223> OTHER INFORMATION: pLYR3p
<220> FEATURE:
<223> OTHER INFORMATION: pLYR3p

<400> SEQUENCE: 97

```
ttatattgaa ttttcaaaaa ttcttacttt ttttttggat ggacgcaaag aagtttaata     60

atcatattac atggcattac caccatatac atatccatat ctaatcttac ttatatgttg    120

tggaaatgta aagagcccga attcctcata ctctggaatc gaaattccgt tggaaaaatt    180

cgctttgtag tgaaaaataa agatgtcaat aaagggtatt gagaatttcc aatggaatta    240

tcagcaatag atgatagaaa gaattcctca tactctggaa tcgaaattcc gttggaaaaa    300

ttcgctttgt agtgaaaaat aaagatgtca ataaagggta ttgagaattt ccaatggaat    360

tatcagcaat agatgataga aagaattcgg atgataatgc gattagtttt ttagccttat    420

ttctggggta attaatcagc gaagcgatga tttttgatct attaacagat atataaatgg    480

aaaagctgca taaccacttt aactaatact ttcaacattt tcagtttgta ttacttctta    540

ttcaaatgtc ataaaagtat caacaaaaaa ttgttaatat acctctatac tttaacgtca    600

aggagaaaaa actata                                                    616
```

<210> SEQ ID NO 98
<211> LENGTH: 616
<212> TYPE: DNA
<213> ORGANISM: Artificial Sequence
<220> FEATURE:
<223> OTHER INFORMATION: pLYR4p
<220> FEATURE:
<223> OTHER INFORMATION: pLYR4p

<400> SEQUENCE: 98
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attctttcta tcatctattg ctgataattc cattggaaat 180
tctcaatacc ctttattgac atctttattt ttcactacaa agcgaatttt tccaacggaa 240
tttcgattcc agagtatgag gaattctttc tatcatctat tgctgataat tccattggaa 300
attctcaata ccctttattg acatctttat ttttcactac aaagcgaatt tttccaacgg 360
aatttcgatt ccagagtatg aggaattcgg atgataatgc gattagtttt ttagccttat 420
ttctggggta attaatcagc gaagcgatga tttttgatct attaacagat atataaatgg 480
aaaagctgca taaccacttt aactaatact ttcaacattt tcagtttgta ttacttctta 540
ttcaaatgtc ataaaagtat caacaaaaaa ttgttaatat acctctatac tttaacgtca 600
aggagaaaaa actata 616

<210> SEQ ID NO 99
<211> LENGTH: 738
<212> TYPE: DNA
<213> ORGANISM: Artificial Sequence
<220> FEATURE:
<223> OTHER INFORMATION: pLYR5p
<220> FEATURE:
<223> OTHER INFORMATION: pLYR5p

<400> SEQUENCE: 99
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attctttcta tcatctattg ctgataattc cattggaaat 180
tctcaatacc ctttattgac atctttattt ttcactacaa agcgaatttt tccaacggaa 240
tttcgattcc agagtatgag gaattctttc tatcatctat tgctgataat tccattggaa 300
attctcaata ccctttattg acatctttat ttttcactac aaagcgaatt tttccaacgg 360
aatttcgatt ccagagtatg aggaattctt tctatcatct attgctgata attccattgg 420
aaattctcaa taccctttat tgacatcttt atttttcact acaaagcgaa tttttccaac 480
ggaatttcga ttccagagta tgaggaattc ggatgataat gcgattagtt ttttagcctt 540
atttctgggg taattaatca gcgaagcgat gatttttgat ctattaacag atatataaat 600
ggaaaagctg cataaccact ttaactaata ctttcaacat tttcagtttg tattacttct 660
tattcaaatg tcataaaagt atcaacaaaa aattgttaat atacctctat actttaacgt 720
caaggagaaa aaactata 738

<210> SEQ ID NO 100
<211> LENGTH: 1104
<212> TYPE: DNA
<213> ORGANISM: Artificial Sequence
<220> FEATURE:
<223> OTHER INFORMATION: pLYR6p
<220> FEATURE:
<223> OTHER INFORMATION: pLYR6p

<400> SEQUENCE: 100
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attgctcata ctctggaatc gaaattccgt tggaaaaatt 180
cgctttgtag tgaaaaataa agatgtcaat aaagggtatt gagaatttcc aatggaatta 240
tcagcaatag atgatagaaa gaattcctca tactctggaa tcgaaattcc gttggaaaaa 300
ttcgctttgt agtgaaaaat aaagatgtca ataaagggta ttgagaattt ccaatggaat 360
tatcagcaat agatgataga aagaattcct catactctgg aatcgaaatt ccgttggaaa 420
aattcgcttt gtagtgaaaa ataaagatgt caataaaggg tattgagaat ttccaatgga 480
attatcagca atagatgata gaaacaattg ctcatactct ggaatcgaaa ttccgttgga 540
aaaattcgct ttgtagtgaa aaataaagat gtcaataaag ggtattgaga atttccaatg 600
gaattatcag caatagatga tagaaagaat tcctcatact ctggaatcga aattccgttg 660
gaaaaattcg ctttgtagtg aaaaataaag atgtcaataa agggtattga gaatttccaa 720
tggaattatc agcaatagat gatagaaaga attcctcata ctctggaatc gaaattccgt 780
tggaaaaatt cgctttgtag tgaaaaataa agatgtcaat aaagggtatt gagaatttcc 840
aatggaatta tcagcaatag atgatagaaa caattcggat gataatgcga ttagtttttt 900
agccttattt ctggggtaat taatcagcga agcgatgatt tttgatctat taacagatat 960
ataaatggaa aagctgcata accactttaa ctaatacttt caacattttc agtttgtatt 1020
acttcttatt caaatgtcat aaaagtatca acaaaaaatt gttaatatac ctctatactt 1080
taacgtcaag gagaaaaaac tata 1104

<210> SEQ ID NO 101
<211> LENGTH: 1836
<212> TYPE: DNA
<213> ORGANISM: Artificial Sequence
<220> FEATURE:
<223> OTHER INFORMATION: pLYR7p
<220> FEATURE:
<223> OTHER INFORMATION: pLYR7p

<400> SEQUENCE: 101
ttatattgaa ttttcaaaaa ttcttacttt ttttttggat ggacgcaaag aagtttaata 60
atcatattac atggcattac caccatatac atatccatat ctaatcttac ttatatgttg 120
tggaaatgta aagagcccga attgtttcta tcatctattg ctgataattc cattggaaat 180
tctcaatacc ctttattgac atctttattt ttcactacaa agcgaatttt tccaacggaa 240
tttcgattcc agagtatgag gaattctttc tatcatctat tgctgataat tccattggaa 300
attctcaata ccctttattg acatctttat ttttcactac aaagcgaatt tttccaacgg 360
aatttcgatt ccagagtatg aggaattctt tctatcatct attgctgata attccattgg 420
aaattctcaa taccctttat tgacatcttt atttttcact acaaagcgaa tttttccaac 480
ggaatttcga ttccagagta tgagcaattg tttctatcat ctattgctga taattccatt 540
ggaaattctc aatacccttt attgacatct ttatttttca ctacaaagcg aatttttcca 600
acggaatttc gattccagag tatgaggaat tctttctatc atctattgct gataattcca 660
ttggaaattc tcaataccct ttattgacat ctttattttt cactacaaag cgaatttttc 720
caacggaatt tcgattccag agtatgagga attctttcta tcatctattg ctgataattc 780
cattggaaat tctcaatacc ctttattgac atctttattt ttcactacaa agcgaatttt 840
tccaacggaa tttcgattcc agagtatgag caattgtttc tatcatctat tgctgataat 900
tccattggaa attctcaata ccctttattg acatctttat ttttcactac aaagcgaatt 960
tttccaacgg aatttcgatt ccagagtatg aggaattctt tctatcatct attgctgata 1020
attccattgg aaattctcaa taccctttat tgacatcttt atttttcact acaaagcgaa 1080
tttttccaac ggaatttcga ttccagagta tgaggaattc tttctatcat ctattgctga 1140
taattccatt ggaaattctc aataccccttt attgacatct ttatttttca ctacaaagcg 1200
aatttttcca acggaatttc gattccagag tatgagcaat tgtttctatc atctattgct 1260
gataattcca ttggaaattc tcaataccct ttattgacat ctttattttt cactacaaag 1320
cgaatttttc caacggaatt tcgattccag agtatgagga attctttcta tcatctattg 1380
ctgataattc cattggaaat tctcaatacc ctttattgac atctttattt ttcactacaa 1440
agcgaatttt tccaacggaa tttcgattcc agagtatgag gaattctttc tatcatctat 1500
tgctgataat tccattggaa attctcaata ccctttattg acatctttat ttttcactac 1560
aaagcgaatt tttccaacgg aatttcgatt ccagagtatg agcaattcgg atgataatgc 1620
gattagtttt ttagccttat ttctggggta attaatcagc gaagcgatga tttttgatct 1680
attaacagat atataaatgg aaaagctgca taaccacttt aactaatact ttcaacattt 1740
tcagtttgta ttacttctta ttcaaatgtc ataaaagtat caacaaaaaa ttgttaatat 1800
acctctatac tttaacgtca aggagaaaaa actata 1836

<210> SEQ ID NO 102
<211> LENGTH: 981
<212> TYPE: DNA
<213> ORGANISM: Artificial Sequence
<220> FEATURE:
<223> OTHER INFORMATION: pLYR8
<220> FEATURE:
<223> OTHER INFORMATION: pLYR8

<400> SEQUENCE: 102
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgctcatact ctggaatcga aattccgttg gaaaaattcg ctttgtagtg aaaaataaag 420
atgtcaataa agggtattga gaatttccaa tggaattatc agcaatagat gatagaaaga 480
attcctcata ctctggaatc gaaattccgt tggaaaaatt cgctttgtag tgaaaaataa 540
agatgtcaat aaagggtatt gagaatttcc aatggaatta tcagcaatag atgatagaaa 600
gaattcctca tactctggaa tcgaaattcc gttggaaaaa ttcgctttgt agtgaaaaat 660
aaagatgtca ataaagggta ttgagaattt ccaatggaat tatcagcaat agatgataga 720
aacaattcta attaagttag tcaaggcgcc atcctcatga aaactgtgta acataataac 780
cgaagtgtcg aaaaggtggc accttgtcca attgaacacg ctcgatgaaa aaaataagat 840
atatataagg ttaagtaaag cgtctgttag aaaggaagtt tttccttttt cttgctctct 900
tgtcttttca tctactattt ccttcgtgta atacagggtc gtcagataca tagatacaat 960
tctattaccc ccatccatac a 981

<210> SEQ ID NO 103
<211> LENGTH: 981
<212> TYPE: DNA
<213> ORGANISM: Artificial Sequence
<220> FEATURE:
<223> OTHER INFORMATION: pLYR9
<220> FEATURE:
<223> OTHER INFORMATION: pLYR9

<400> SEQUENCE: 103
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgtttctatc atctattgct gataattcca ttggaaattc tcaataccct ttattgacat 420
ctttattttt cactacaaag cgaatttttc caacggaatt tcgattccag agtatgagga 480
attctttcta tcatctattg ctgataattc cattggaaat tctcaatacc ctttattgac 540
atctttattt ttcactacaa agcgaatttt tccaacggaa tttcgattcc agagtatgag 600
gaattctttc tatcatctat tgctgataat tccattggaa attctcaata ccctttattg 660
acatctttat ttttcactac aaagcgaatt tttccaacgg aatttcgatt ccagagtatg 720
agcaattcta attaagttag tcaaggcgcc atcctcatga aaactgtgta acataataac 780
cgaagtgtcg aaaaggtggc accttgtcca attgaacacg ctcgatgaaa aaaataagat 840
atatataagg ttaagtaaag cgtctgttag aaaggaagtt tttccttttt cttgctctct 900
tgtcttttca tctactattt ccttcgtgta atacagggtc gtcagataca tagatacaat 960
tctattaccc ccatccatac a 981

<210> SEQ ID NO 104
<211> LENGTH: 1225
<212> TYPE: DNA
<213> ORGANISM: Artificial Sequence
<220> FEATURE:
<223> OTHER INFORMATION: pLYR10
<220> FEATURE:
<223> OTHER INFORMATION: pLYR10

<400> SEQUENCE: 104
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgtttctatc atctattgct gataattcca ttggaaattc tcaataccct ttattgacat 420
ctttattttt cactacaaag cgaatttttc caacggaatt tcgattccag agtatgagga 480
attctttcta tcatctattg ctgataattc cattggaaat tctcaatacc ctttattgac 540
atctttattt ttcactacaa agcgaatttt tccaacggaa tttcgattcc agagtatgag 600
gaattctttc tatcatctat tgctgataat tccattggaa attctcaata ccctttattg 660
acatctttat ttttcactac aaagcgaatt tttccaacgg aatttcgatt ccagagtatg 720
aggaattctt tctatcatct attgctgata attccattgg aaattctcaa taccctttat 780
tgacatcttt atttttcact acaaagcgaa tttttccaac ggaatttcga ttccagagta 840
tgaggaattc tttctatcat ctattgctga taattccatt ggaaattctc aataccctttt 900 attgacatct ttatttttca ctacaaagcg aatttttcca acggaatttc gattccagag 960
tatgagcaat tctaattaag ttagtcaagg cgccatcctc atgaaaactg tgtaacataa 1020
taaccgaagt gtcgaaaagg tggcaccttg tccaattgaa cacgctcgat gaaaaaaata 1080
agatatatat aaggttaagt aaagcgtctg ttagaaagga agtttttcct ttttcttgct 1140
ctcttgtctt ttcatctact atttccttcg tgtaatacag ggtcgtcaga tacatagata 1200
caattctatt acccccatcc ataca 1225

<210> SEQ ID NO 105
<211> LENGTH: 1347
<212> TYPE: DNA
<213> ORGANISM: Artificial Sequence
<220> FEATURE:
<223> OTHER INFORMATION: pLYR11
<220> FEATURE:
<223> OTHER INFORMATION: pLYR11

<400> SEQUENCE: 105
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgaat 360
tgctcatact ctggaatcga aattccgttg gaaaaattcg ctttgtagtg aaaaataaag 420
atgtcaataa agggtattga gaatttccaa tggaattatc agcaatagat gatagaaaga 480
attcctcata ctctggaatc gaaattccgt tggaaaaatt cgctttgtag tgaaaaataa 540
agatgtcaat aaagggtatt gagaatttcc aatggaatta tcagcaatag atgatagaaa 600
gaattcctca tactctggaa tcgaaattcc gttggaaaaa ttcgctttgt agtgaaaaat 660
aaagatgtca ataaagggta ttgagaattt ccaatggaat tatcagcaat agatgataga 720
aagaattcct catactctgg aatcgaaatt ccgttggaaa aattcgcttt gtagtgaaaa 780
ataaagatgt caataaaggg tattgagaat ttccaatgga attatcagca atagatgata 840
gaaagaattc ctcatactct ggaatcgaaa ttccgttgga aaaattcgct ttgtagtgaa 900
aaataaagat gtcaataaag ggtattgaga atttccaatg gaattatcag caatagatga 960
tagaaagaat tcctcatact ctggaatcga aattccgttg gaaaaattcg ctttgtagtg 1020
aaaaataaag atgtcaataa agggtattga gaatttccaa tggaattatc agcaatagat 1080
gatagaaaca attctaatta agttagtcaa ggcgccatcc tcatgaaaac tgtgtaacat 1140
aataaccgaa gtgtcgaaaa ggtggcacct tgtccaattg aacacgctcg atgaaaaaaa 1200
taagatatat ataaggttaa gtaaagcgtc tgttagaaag gaagtttttc ctttttcttg 1260
ctctcttgtc ttttcatcta ctatttcctt cgtgtaatac agggtcgtca gatacataga 1320
tacaattcta ttacccccat ccataca 1347

<210> SEQ ID NO 106
<211> LENGTH: 686
<212> TYPE: DNA
<213> ORGANISM: Saccharomyces cerevisiae
<220> FEATURE:
<223> OTHER INFORMATION: pMET17
<220> FEATURE:
<223> OTHER INFORMATION: pMET17

<400> SEQUENCE: 106
ttacattatc aatccttgcg tttcagcttc cactaattta gatgactatt tctcatcatt 60
tgcgtcatct tctaacaccg tatatgataa tatactagta acgtaaatac tagttagtag 120
atgatagttg atttttattc caacactaag aaataatttc gccatttctt gaatgtattt 180
aaagatattt aatgctataa tagacattta aatccaattc ttccaacata caatgggagt 240
ttggccgagt ggtttaaggc gtcagattta ggtggattta acctctaaaa tctctgatat 300
cttcggatgc aagggttcga atcccttagc tctcattatt ttttgctttt tctcttgagg 360
tcacatgatc gcaaaatggc aaatggcacg tgaagctgtc gatattgggg aactgtggtg 420
gttggcaaat gactaattaa gttagtcaag gcgccatcct catgaaaact gtgtaacata 480
ataaccgaag tgtcgaaaag gtggcacctt gtccaattga acacgctcga tgaaaaaaat 540
aagatatata taaggttaag taaagcgtct gttagaaagg aagtttttcc tttttcttgc 600
tctcttgtct tttcatctac tatttccttc gtgtaataca gggtcgtcag atacatagat 660
acaattctat tacccccatc cataca 686

<210> SEQ ID NO 107
<211> LENGTH: 510
<212> TYPE: DNA
<213> ORGANISM: Saccharomyces cerevisiae
<220> FEATURE:
<223> OTHER INFORMATION: pMET6
<220> FEATURE:
<223> OTHER INFORMATION: pMET6

<400> SEQUENCE: 107
ccacaggaaa tatttcacgt gacttacaaa cagagtcgta cgtcaggacc ggagtcaggt 60
gaaaaaatgt gggccggtaa agggaaaaaa ccagaaacgg gactactatc gaactcgttt 120
agtcgcgaac gtgcaaaagg ccaatatttt tcgctagagt catcgcagtc atggcagctc 180
tttcgctcta tctcccggtc gcaaaactgt ggtagtcata gctcgttctg ctcaattgag 240
aactgtgaat gtgaatatgg aacaaatgcg atagatgcac taatttaagg gaagctagct 300
agttttccca actgcgaaag aaaaaaagga aagaaaaaaa aattctatat aagtgataga 360
tatttccatc tttactagca ttagtttctc ttttacgtat tcaatatttt tgttaaactc 420
ttcctttatc ataaaaaagc aagcatctaa gagcattgac aacactctaa gaaacaaaat 480
accaatataa tttcaaagta catatcaaaa 510

<210> SEQ ID NO 108
<211> LENGTH: 508
<212> TYPE: DNA
<213> ORGANISM: Saccharomyces cerevisiae
<220> FEATURE:
<223> OTHER INFORMATION: pMET14
<220> FEATURE:

<223> OTHER INFORMATION: pMET14

<400> SEQUENCE: 108
cctatgcatg tttagagcaa gcgcctttgt gagccctccc ggttacgacg ccttggcaat 60
gtagcagata actctgcact tctagaatca ttccactacg acatttggct catcaccagc 120
tcgcgagaaa tgtaaataag ccaacaacca agaatgcgta acattaaaga atacagttgc 180
tttcatttcg gcgtgatggt acggcaccca cggttcctta cattattctc gaaaaatagc 240
tgcacgcttt tccaggaata aaagaccgtg ccactaattt cacgtgatca atatatttac 300
aagccacctc aaaaaatgtg gcaatggaga agaggatgaa cgactcaata tgacttcaac 360
ttcatgaatt tgtcaaaata tctatataag atgcaaaatt tctatacaac atcagttgcg 420
tatccgttaa tgtcgttcat tttctctctt tgttcgaact tgacatcaag aaaagttgga 480
attatttctc caagcacact gtacacca 508

<210> SEQ ID NO 109
<211> LENGTH: 552
<212> TYPE: DNA
<213> ORGANISM: Saccharomyces cerevisiae
<220> FEATURE:
<223> OTHER INFORMATION: pMET3
<220> FEATURE:
<223> OTHER INFORMATION: pMET3

<400> SEQUENCE: 109
aacgatatgt acgtagtggt ataaggtgag gggtccaca gatataacat cgtttaattt 60
agtactaaca gagacttttg tcacaactac atataagtgt acaaatatag tacagatatg 120
acacacttgt agcgccaacg cgcatcctac ggattgctga cagaaaaaaa ggtcacgtga 180
ccagaaaagt cacgtgtaat tttgtaactc accgcattct agcggtccct gtcgtgcaca 240
ctgcactcaa caccataaac cttagcaacc tccaaaggaa atcaccgtat aacaaagcca 300
cagttttaca acttagtctc ttatgaagtt acttaccaat gagaaataga ggctctttct 360
cgacaaatat gaatatggat atatatatat atatatatat atatatatat atatatatgt 420
aaacttggtt cttttttagc ttgtgatctc tagcttgggt ctctctctgt cgtaacagtt 480
gtgatatcgt ttcttaacaa ttgaaaagga actaagaaag tataataata acaagaataa 540
agtataatta ac 552

<210> SEQ ID NO 110
<211> LENGTH: 363
<212> TYPE: DNA
<213> ORGANISM: Saccharomyces cerevisiae
<220> FEATURE:
<223> OTHER INFORMATION: pSAM1
<220> FEATURE:
<223> OTHER INFORMATION: pSAM1

<400> SEQUENCE: 110
gaaacggacg taagacggaa atagaatttg aagataaagt tatatatcac tacacacgaa 60
tactttcttt tttttttttc acaggaaaac tgtggtggcg cccttgccta ctagtgcatt 120
tcttttttcg ggttcttgtc tcgacgaaat tttagcctca tcgtagtttt tcactctggt 180
atcgatgaaa aagggaagag taaaaagttt tccgtttagt acttaatggg attggtttgg 240
gacgtatata tcgactggtg ttgtctgtta ttcatcgttg tttttcggtt agcttcgaaa 300
aaaaaataga gtaaaaacca ggaatttacc ctaaaaacaa gaaaaaataa gataaacgaa 360
aat 363

<210> SEQ ID NO 111
<211> LENGTH: 500
<212> TYPE: DNA
<213> ORGANISM: Saccharomyces cerevisiae
<220> FEATURE:
<223> OTHER INFORMATION: pSAM2
<220> FEATURE:
<223> OTHER INFORMATION: pSAM2

<400> SEQUENCE: 111
gagctttgct ctattatata agataaaata tgcactaaaa gtttgcattt ctttacataa 60
ctaaaactaa gacattatgc atagcttacc tgatcaaaaa gtatgtaaac ttgttaacat 120
cttcacatgt gattcatctg gtcgtacttt cttgcggtgc agtgtaatat ttctacccac 180
gtgactataa ttgagcttga aaactgtggc gtttttccac cgatgggtcc acgccagata 240
ttaaccgaag ccaaaatacc gatgaaattt ctgagatagc tcttgtaaac gacgtcaaat 300
cttcatatgc aaggagatct tgatttcttt ttggtagtca tctgtcgtct tgaggcgtat 360
aagaaggagg ttatatctgt cctttctaca aagtattttc gagaatcttg cttctgcccc 420
ttttttcttt ttttaaaagg tttaaaaaac ataactgtct tcaatatatc cagtatttac 480
gacaatatac aaacataatc 500

<210> SEQ ID NO 112
<211> LENGTH: 300
<212> TYPE: DNA
<213> ORGANISM: Saccharomyces cerevisiae
<220> FEATURE:
<223> OTHER INFORMATION: tTDH2
<220> FEATURE:
<223> OTHER INFORMATION: tTHD2

<400> SEQUENCE: 112
atttaactcc ttaagttact ttaatgattt agtttttatt attaataatt catgctcatg 60
acatctcata tacacgttta taaaacttaa atagattgaa aatgtattaa agattcctca 120
gggattcgat ttttttggaa gtttttgttt ttttttcctt gagatgctgt agtatttggg 180
aacaattata caatcgaaag atatatgctt acattcgacc gttttagccg tgatcattat 240
cctatagtaa cataacctga agcataactg acactactat catcaatact tgtcacatga 300

<210> SEQ ID NO 113
<211> LENGTH: 300
<212> TYPE: DNA
<213> ORGANISM: Saccharomyces cerevisiae
<220> FEATURE:
<223> OTHER INFORMATION: tCYC1
<220> FEATURE:
<223> OTHER INFORMATION: tCYC1

<400> SEQUENCE: 113
acaggcccct tttcctttgt cgatatcatg taattagtta tgtcacgctt acattcacgc 60
cctcctccca catccgctct aaccgaaaag gaaggagtta gacaacctga agtctaggtc 120
cctatttatt ttttttaata gttatgttag tattaagaac gttatttata tttcaaattt 180
ttcttttttt tctgtacaaa cgcgtgtacg catgtaacat tatactgaaa accttgcttg 240
agaaggtttt gggacgctcg aaggctttaa tttgcaagct tcgcagttta cactctcatc 300

<210> SEQ ID NO 114
<211> LENGTH: 300
<212> TYPE: DNA

<213> ORGANISM: Saccharomyces cerevisiae
<220> FEATURE:
<223> OTHER INFORMATION: tTDH3
<220> FEATURE:
<223> OTHER INFORMATION: tTDH3

<400> SEQUENCE: 114
gtgaatttac tttaaatctt gcatttaaat aaattttctt tttatagctt tatgacttag 60
tttcaattta tatactattt taatgacatt ttcgattcat tgattgaaag ctttgtgttt 120
tttcttgatg cgctattgca ttgttcttgt ctttttcgcc acatgtaata tctgtagtag 180
atacctgata cattgtggat gctgagtgaa attttagtta ataatggagg cgctcttaat 240
aattttgggg atattggctt ttttttttaa agtttacaaa tgaatttttt ccgccaggat 300

<210> SEQ ID NO 115
<211> LENGTH: 354
<212> TYPE: DNA
<213> ORGANISM: Saccharomyces cerevisiae
<220> FEATURE:
<223> OTHER INFORMATION: tADH1
<220> FEATURE:
<223> OTHER INFORMATION: tADH1

<400> SEQUENCE: 115
actagttcta gagcggccgc caccgcggtg ggcgaatttc ttatgattta tgatttttat 60
tattaaataa gttataaaaa aaataagtgt atacaaattt taaagtgact cttaggtttt 120
aaaacgaaaa ttcttattct tgagtaactc tttcctgtag gtcaggttgc tttctcaggt 180
atagcatgag gtcgctctta ttgaccacac ctctaccggc atgccgagca aatgcctgca 240
aatcgctccc catttcaccc aattgtagat atgctaactc cagcaatgag ttgatgaatc 300
tcggtgtgta ttttatgtcc tcagaggaca acacctgttg taatcgttct tcca 354

<210> SEQ ID NO 116
<211> LENGTH: 301
<212> TYPE: DNA
<213> ORGANISM: Saccharomyces cerevisiae
<220> FEATURE:
<223> OTHER INFORMATION: tADH2
<220> FEATURE:
<223> OTHER INFORMATION: tADH2

<400> SEQUENCE: 116
gcggatctct tatgtcttta cgatttatag ttttcattat caagtatgcc tatattagta 60
tatagcatct ttagatgaca gtgttcgaag tttcacgaat aaaagataat attctacttt 120
ttgctcccac cgcgtttgct agcacgagtg aacaccatcc ctcgcctgtg agttgtaccc 180
attcctctaa actgtagaca tggtagcttc agcagtgttc gttatgtacg gcatcctcca 240
acaaacagtc ggttatagtt tgtcctgctc ctctgaatcg tctccctcga tatttctcat 300
t 301

<210> SEQ ID NO 117
<211> LENGTH: 299
<212> TYPE: DNA
<213> ORGANISM: Saccharomyces cerevisiae
<220> FEATURE:
<223> OTHER INFORMATION: tTPI1
<220> FEATURE:
<223> OTHER INFORMATION: tTPI1

<400> SEQUENCE: 117
gattaatata attatataaa aatattatct tcttttcttt atatctagtg ttatgtaaaa 60
taaattgatg actacggaaa gctttttttat attgtttctt tttcattctg agccacttaa 120
atttcgtgaa tgttcttgta agggacggta gatttacaag tgatacaaca aaaagcaagg 180
cgctttttct aataaaaaga agaaaagcat ttaacaattg aacacctcta tatcaacgaa 240
gaatattact ttgtctctaa atccttgtaa aatgtgtacg atctctatat gggttactc 299

<210> SEQ ID NO 118
<211> LENGTH: 299
<212> TYPE: DNA
<213> ORGANISM: Saccharomyces cerevisiae
<220> FEATURE:
<223> OTHER INFORMATION: tMET17
<220> FEATURE:
<223> OTHER INFORMATION: tMET17

<400> SEQUENCE: 118
gtgtgcgtaa tgagttgtaa aattatgtat aaacctactt tctctcacaa gtactatact 60
tttataaaac gaactttatt gaaatgaata tcctttttttt cccttgttac atgtcgtgac 120
tcgtactttg aacctaaatt gttctaacat caaagaacag tgttaattcg cagtcgagaa 180
gaaaaatatg gtgaacaaga ctcatctact tcatgagact actttacgcc tcctataaag 240
ctgtcacact ggataaattt attgtaggac caagttacaa aagaggatga tggaggttt 299

<210> SEQ ID NO 119
<211> LENGTH: 305
<212> TYPE: DNA
<213> ORGANISM: Saccharomyces cerevisiae
<220> FEATURE:
<223> OTHER INFORMATION: tENO2
<220> FEATURE:
<223> OTHER INFORMATION: tENO2

<400> SEQUENCE: 119
ggatcctaaa gtgcttttaa ctaagaatta ttagtctttt ctgcttattt tttcatcata 60
gtttagaaca ctttatatta acgaatagtt tatgaatcta tttaggttta aaaattgata 120
cagttttata agttactttt tcaaagactc gtgctgtcta ttgcataatg cactggaagg 180
ggaaaaaaaa ggtgcacacg cgtggctttt tcttgaattt gcagtttgaa aaataactac 240
atggatgata agaaaacatg gagtacagtc actttgagaa ccttcaatca gctggtaacg 300
tcttc 305

<210> SEQ ID NO 120
<211> LENGTH: 300
<212> TYPE: DNA
<213> ORGANISM: Saccharomyces cerevisiae
<220> FEATURE:
<223> OTHER INFORMATION: tMET3
<220> FEATURE:
<223> OTHER INFORMATION: tMET3

<400> SEQUENCE: 120
tcgtcataaa atgctcccat ctcaaaagta gggcaaaatt catgatcgac cgcgcaaaat 60
aaatagattt gcaaataagt tttgtatgta catttattaa tatatataat atatcaaaag 120
aaaaaaatca aaaaaaaaaa aaaaaaaaaa ttgcactctt attcagtcat caattacaaa 180
acctagagat agcgatggtg catattcaat aaaaaactcc ttatactgtc gagaaagctt 240
attattggta cttctcgaag atactaaaaa aggttaattt ttggagacgg aggcaatagc 300

<210> SEQ ID NO 121

<211> LENGTH: 301
<212> TYPE: DNA
<213> ORGANISM: Saccharomyces cerevisiae
<220> FEATURE:
<223> OTHER INFORMATION: tPGK1
<220> FEATURE:
<223> OTHER INFORMATION: tPGK1

<400> SEQUENCE: 121
attgaattga attgaaatcg atagatcaat ttttttcttt tctctttccc catcctttac 60
gctaaaataa tagtttattt tattttttga atatttttta tttatatacg tatatataga 120
ctattattta tcttttaatg attattaaga tttttattaa aaaaaaattc gctcctcttt 180
taatgccttt atgcagtttt tttttcccat tcgatatttc tatgttcggg ttcagcgtat 240
tttaagttta ataactcgaa aattctgcgt tcgttaaagc tttcgagaag gatattattt 300
a 301

<210> SEQ ID NO 122
<211> LENGTH: 300
<212> TYPE: DNA
<213> ORGANISM: Saccharomyces cerevisiae
<220> FEATURE:
<223> OTHER INFORMATION: tDIT1
<220> FEATURE:
<223> OTHER INFORMATION: tDIT1

<400> SEQUENCE: 122
taaagtaaga gcgctacatt ggtctacctt tttgttcttt tacttaaaca ttagttagtt 60
cgttttcttt ttctcatttt tttatgtttc ccccccaaag ttctgatttt ataatatttt 120
atttcacaca attccattta acagaggggg aatagattct ttagcttaga aaattagtga 180
tcaatatata tttgcctttc ttttcatctt ttcagtgata ttaatggttt cgagacactg 240
caatggccct agttgtctaa gaggatagat gttactgtca aagatgatat tttgaatttc 300

<210> SEQ ID NO 123
<211> LENGTH: 300
<212> TYPE: DNA
<213> ORGANISM: Saccharomyces cerevisiae
<220> FEATURE:
<223> OTHER INFORMATION: tRPL3
<220> FEATURE:
<223> OTHER INFORMATION: tRPL3

<400> SEQUENCE: 123
gaagttttgt tagaaaataa atcatttttt aattgagcat tcttattcct attttattta 60
aatagtttta tgtattgtta gctacataca acagtttaaa tcaaattttc tttttcccaa 120
gtccaaaatg gaggtttatt ttgatgaccc gcatgcgatt atgttttgaa agtataagac 180
tacatacatg tacatatatt taaacatgta aacccgtcca ttatattgct tactttcttc 240 tttttgccg ttttgacttg gacctctggt ttgctatttc cttacaatct ttgctacaat 300

<210> SEQ ID NO 124
<211> LENGTH: 300
<212> TYPE: DNA
<213> ORGANISM: Saccharomyces cerevisiae
<220> FEATURE:
<223> OTHER INFORMATION: tRPL41B
<220> FEATURE:
<223> OTHER INFORMATION: tRPL41B

<400> SEQUENCE: 124
gcggattgag agcaaatcgt taagttcagg tcaagtaaaa attgatttcg aaaactaatt 60
tctcttatac aatcctttga ttggaccgtc atcctttcga atataagatt ttgttaagaa 120
tattttagac agagatctac tttatattta atatctagat attacataat ttcctctcta 180
ataaaatatc attaataaaa taaaaatgaa gcgatttgat tttgtgttgt caacttagtt 240
tgccgctatg cctcttgggt aatgctatta ttgaatcgaa gggctttatt atattaccct 300

<210> SEQ ID NO 125
<211> LENGTH: 300
<212> TYPE: DNA
<213> ORGANISM: Saccharomyces cerevisiae
<220> FEATURE:
<223> OTHER INFORMATION: tRPL15A
<220> FEATURE:
<223> OTHER INFORMATION: tRPL15A

<400> SEQUENCE: 125
gctggttgat ggaaaatata attttattgg gcaaactttt gtttatctga tgtgttttat 60
actattatct ttttaattaa tgattctata tacaaacctg tatatttttt ctttaaccaa 120 ttttttttt tatagaccta gagctgtact tttattctgc tatcaagcaa acccctaccc 180
cctcttctca atcctcccct caggcagaac ttatctacct gtatcaagga gcggacgagg 240
gagtcctaat tgttctacgt ataccaatgc tagcagctta cataggtggt ggcactacca 300

<210> SEQ ID NO 126
<211> LENGTH: 300
<212> TYPE: DNA
<213> ORGANISM: Saccharomyces cerevisiae
<220> FEATURE:
<223> OTHER INFORMATION: tIDP1
<220> FEATURE:
<223> OTHER INFORMATION: tIDP1

<400> SEQUENCE: 126
tcgaatttac gtagcccaat ctaccacttt tttttttcat tttttaaagt gttatactta 60
gttatgctct aggataatga actacttttt tttttttttt tttactgtta tcataaatat 120 atataccttta ttgttgtttg caaccgtcgg ttaattcctt atcaaggttc cccaagttcg 180
gatcattacc atcaatttcc aacattttca tgagttcttc ttcttcatta ccgtgtttta 240
gggggctgtt cgcacttcta atagggctat caccaagctg ttctaattcg tccaaaagtt 300

<210> SEQ ID NO 127
<211> LENGTH: 1089
<212> TYPE: DNA
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 127
atgtctaaga atatcgttgt cctaccgggt gatcacgtcg gtaaagaagt tactgacgaa 60
gctattaagg tcttgaatgc cattgctgaa gtccgtccag aaattaagtt caatttccaa 120
catcacttga tcgggggtgc tgccatcgat gccactggca ctcctttacc agatgaagct 180
ctagaagcct ctaagaaagc cgatgctgtc ttactaggtg ctgttggtgg tccaaaatgg 240
ggtacgggcg cagttagacc agaacaaggt ctattgaaga tcagaaagga attgggtcta 300
tacgccaact tgagaccatg taactttgct tctgattctt tactagatct ttctcctttg 360
aagcctgaat atgcaaaggg taccgatttc gtcgtcgtta gagaattggt tggtggtatc 420

-continued

```
tactttggtg aaagaaaaga agatgaaggt gacggagttg cttgggactc tgagaaatac    480

agtgttcctg aagttcaaag aattacaaga atggctgctt tcttggcatt gcaacaaaac    540

ccaccattac caatctggtc tcttgacaag gctaacgtgc ttgcctcttc cagattgtgg    600

agaaagactg ttgaagaaac catcaagact gagttcccac aattaactgt tcagcaccaa    660

ttgatcgact ctgctgctat gattttggtt aaatcaccaa ctaagctaaa cggtgttgtt    720

attaccaaca acatgtttgg tgatattatc tccgatgaag cctctgttat tccaggttct    780

ttgggtttat taccttctgc atctctagct tccctacctg acactaacaa ggcattcggt    840

ttgtacgaac catgtcatgg ttctgcccca gatttaccag caaacaaggt taacccaatt    900

gctaccatct tatctgcagc tatgatgttg aagttatcct tggatttggt tgaagaaggt    960

agggctcttg aagaagctgt tagaaatgtc ttggatgcag gtgtcagaac cggtgacctt   1020

ggtggttcta actctaccac tgaggttggc gatgctatcg ccaaggctgt caaggaaatc   1080

ttggcttaa                                                            1089
```

<210> SEQ ID NO 128
<211> LENGTH: 362
<212> TYPE: PRT
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 128

```
Met Ser Lys Asn Ile Val Val Leu Pro Gly Asp His Val Gly Lys Glu
1               5                   10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
```

-continued

```
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270

Pro Asp Thr Asn Lys Ala Phe Gly Leu Tyr Glu Pro Cys His Gly Ser
        275                 280                 285

Ala Pro Asp Leu Pro Ala Asn Lys Val Asn Pro Ile Ala Thr Ile Leu
    290                 295                 300

Ser Ala Ala Met Met Leu Lys Leu Ser Leu Asp Leu Val Glu Glu Gly
305                 310                 315                 320

Arg Ala Leu Glu Glu Ala Val Arg Asn Val Leu Asp Ala Gly Val Arg
                325                 330                 335

Thr Gly Asp Leu Gly Gly Ser Asn Ser Thr Thr Glu Val Gly Asp Ala
            340                 345                 350

Ile Ala Lys Ala Val Lys Glu Ile Leu Ala
        355                 360
```

<210> SEQ ID NO 129
<211> LENGTH: 499
<212> TYPE: DNA
<213> ORGANISM: Saccharomyces cerevisiae
<220> FEATURE:
<223> OTHER INFORMATION: pNUP57
<220> FEATURE:
<223> OTHER INFORMATION: pNUP57

<400> SEQUENCE: 129

```
tcatctgcgc aatgactatc aagaccttct gcaagaattt caaatctcac tgaaaatctt     60

gaccgaaaag tgtcttgaaa acccatcaag cctgcaaaac ctatctttga cattagtctc    120

cattataaaa acggcatagt tgggagaaaa cttttcatac ttcaattgtg gactgatata    180

agtattttgg ttttgcccgc atgatcatcc cacatggcta cagcagttct ctcataggaa    240

atagtacaat agctacgtga tataatctaa ataattgttg ccaatgtgta attatatcat    300

tttgaacgtt cgcgaaatgg attattttca aaaattttgt ttcttgaaat gagtaaaagc    360

aaaagtccaa ctctccaagt cgatgtaaac aactttttgc caaagggact gaaagactaa    420

atcgaggatt atcccgttca aactattcca gaaacgctcg ttagtaacaa aagacatacc    480

ttgttgacca attgatcac                                                 499
```

<210> SEQ ID NO 130
<211> LENGTH: 451
<212> TYPE: DNA
<213> ORGANISM: Saccharomyces cerevisiae
<220> FEATURE:
<223> OTHER INFORMATION: pGAP1
<220> FEATURE:
<223> OTHER INFORMATION: pGAP1

<400> SEQUENCE: 130

```
cactttcacc agatcccaaa tgtcccgccc ctattcccgt gttccatcac gtaccataac     60

ttaccatttc atcacgttct ctatggcaca ctggtactgc ttcgactgct ttgcttcatc    120

ttctctatgg gccaatgagc taatgagcac aatgtgctgc gaaataaagg gatatctaat    180

ttatattatt acattataat atgtactagt gtggttattg gtaattgtac ttaattttga    240

tatataaagg gtggatcttt ttcattttga atcagaattg gaattgcaac ttgtctcttg    300

tcactattac ttaatagtaa ttatatttct tattaacctt ttttttaagt caaaacacca    360
```

aggacaagaa ctactcttca aaggtatttc aagttatcat acgtctcaca cacgcttcac 420
agtttcaagt aaaaaaaaag aatattacac a 451

<210> SEQ ID NO 131
<211> LENGTH: 998
<212> TYPE: DNA
<213> ORGANISM: Saccharomyces cerevisiae
<220> FEATURE:
<223> OTHER INFORMATION: pJEN1
<220> FEATURE:
<223> OTHER INFORMATION: pJEN1

<400> SEQUENCE: 131
aatgtgttta taaattattt tttttgctgg tagcaaaatc aactcattgt cttccattca 60
gagtctaatc gaacgttatc gcaatgcttg cacactttta aacaatacga tttagtttaa 120
gtggatggac ccccacgctt agtgttccac aggtttgtcc ccactgtttt tacattccac 180
tgtacatttt tgcaatagaa ggtcattgta tgctaccttg ggcggctaag aatacctgta 240
aaaatttgga gaaattagat tcgtaaagaa tgactcgcaa cgactccaat gatttcttct 300
tttcaccctt tgaacggccg atatccgcgc gggatcctga ccccgcaatt tactccacta 360
gaccggcgtg tttctctttt tccttttcct ggggttagag cccaagagct aatagccgac 420
aaacggactc caaaaaaaaa aggaggcaca ggacaaacgc agcacctgcg tcattcacgc 480
tgaagcggca gcaagcattt tcgatcagct ccaattaaat gaagactatt cgccgtaccg 540
ttcccagatg ggtgcgaaag tcagtgatcg aggaagttat tgagcgcgcg gcttgaaact 600
atttctccat ctcagagccg ccaagcctac cattattctc caccaggaag ttagtttgta 660
agcttctgca caccatccgg acgtccataa ttcttcactt aacggtcttt tgcccccccct 720 tctactataa tgcattagaa cgttacctgg tcatttggat ggagatctaa gtaacactta 780
ctatctccta tggtactatc ctttaccaaa aaaaaaaaaa aaaaaaaaaa aaaaaatcag 840
caaagtgaag taccctcttg atgtataaat acattgcaca tcattgttga gaaatagttt 900
tggaagttgt ctagtccttc tcccttagat ctaaaaggaa gaagagtaac agtttcaaaa 960
gtttttcctc aaagagatta aatactgcta ctgaaaat 998

<210> SEQ ID NO 132
<211> LENGTH: 450
<212> TYPE: DNA
<213> ORGANISM: Saccharomyces cerevisiae
<220> FEATURE:
<223> OTHER INFORMATION: pICL1
<220> FEATURE:
<223> OTHER INFORMATION: pICL1

<400> SEQUENCE: 132
ttttgctact cgtcatccga tgagaaaaac tgttcccttt tgccccaggt ttccattcat 60
ccgagcgatc acttatctga cttcgtcact ttttcatttc atccgaaaca atcaaaactg 120
aagccaatca ccacaaaatt aacactcaac gtcatctttc actacccttt acagaagaaa 180
atatccatag tccggactag catcccagta tgtgactcaa tattggtgca aaagagaaaa 240
gcataagtca gtccaaagtc cgcccttaac caggcacatc ggaattcaca aaacgtttct 300
ttattatata aaggagctgc ttcactggca aaattcttat tatttgtctt ggcttgctaa 360
tttcatctta tcctttttttt cttttcacac ccaaatacct aacaattgag agaaaactct 420
tagcataaca taacaaaaag tcaacgaaaa 450

<210> SEQ ID NO 133
<211> LENGTH: 598
<212> TYPE: DNA
<213> ORGANISM: Saccharomyces cerevisiae
<220> FEATURE:
<223> OTHER INFORMATION: pADH2
<220> FEATURE:
<223> OTHER INFORMATION: pADH2

<400> SEQUENCE: 133

```
tatcttaact gatagtttga tcaaaggggc aaaacgtagg ggcaaacaaa cggaaaaatc     60
gtttctcaaa ttttctgatg ccaagaactc taaccagtct tatctaaaaa ttgccttatg    120
atccgtctct ccggttacag cctgtgtaac tgattaatcc tgcctttcta atcaccattc    180
taatgtttta attaagggat tttgtcttca ttaacggctt tcgctcataa aaatgttatg    240
acgttttgcc cgcaggcggg aaaccatcca cttcacgaga ctgatctcct ctgccggaac    300
accgggcatc tccaacttat aagttggaga aataagagaa tttcagattg agagaatgaa    360
aaaaaaaaaa aaaaaaggca gaggagagca tagaaatggg gttcactttt tggtaaagct    420
atagcatgcc tatcacatat aaatagagtg ccagtagcga ctttttttcac actcgaaata    480
ctcttactac tgctctcttg ttgtttttat cacttcttgt ttcttcttgg taaatagaat    540
atcaagctac aaaaagcata caatcaacta tcaactatta actatatcgt aatacaca      598
```

<210> SEQ ID NO 134
<211> LENGTH: 793
<212> TYPE: DNA
<213> ORGANISM: Saccharomyces cerevisiae
<220> FEATURE:
<223> OTHER INFORMATION: pMLS1
<220> FEATURE:
<223> OTHER INFORMATION: pMLS1

<400> SEQUENCE: 134

```
tgtctaatgc gaaggtactt ttattttttt cagattcaaa gcaatattat ttagacaatt     60
gatactaagt gagcttaagg aggattaaac aactgtggaa tccttcacaa ggattcaata    120
tttgtttttc ctggttattt tgccatcatt caactttcct cagacgtaaa attcgtgctt    180
agtgatgtct caatattccc gcagggtaat aaaattcaat aactatcact atatacgcaa    240
cagtattacc ctacattgct atcggctcaa tggaaatccc catatcatag cttccattgg    300
gccgatgaag ttagtcgacg gatagaagcg gttgtcccct ttcccggcga gccggcagtc    360
gggccgaggt tcggataaat tttgtattgt gttttgattc tgtcatgagt attacttatg    420
ttctctttag gtaaccccag gttaatcaat cacagtttca taccggctag tattcaaatt    480
atgacttttc ttctgcagtg tcagccttac gacgattatc tatgagcttt gaatatagtt    540
tgccgtgatt cgtatcttta attggataat aaaatgcgaa ggatcgatga cccttattat    600
tatttttcta cactggctac cgatttaact catcttcttg aaagtatata agtaacagta    660
aaatataccg tacttctgct aatgttattt gtcccttatt tttcttttct tgtcttatgc    720
tatagtacct aagaataacg actattgttt tgaactaaac aaagtagtaa aagcacataa    780
aagaattaag aaa                                                       793
```

ENHANCED METABOLITE-PRODUCING YEAST

FIELD OF THE INVENTION

The present invention relates to the field of bio-production of metabolites, and in particular of metabolites produced by a microorganism using more particularly oxaloacetate as substrate or co-substrate upstream in the biosynthesis pathway. Said metabolites are preferably amino acids and amino acids derivatives.

BACKGROUND OF THE INVENTION

Amino acids support an industry worth billions of dollars worldwide. All twenty amino acids are sold and of interest in different fields. They can be used as animal feed additives, as for example lysine, methionine and threonine, as specialty nutrients in the medical field and as flavor enhancers, as for example monosodium glutamic acid (or monosodium glutamate), serine and aspartic acid. Amino acids and their derivatives are moreover important precursors in the pharmaceutical industry.

There are three general approaches used today for making amino acids: direct chemical synthesis, bioconversion using enzymes and fermentation. Choosing between these processes depends on available technology, costs of raw material, market prices and sizes, as well as cost of running fermentation versus synthesis reactions, and the environmental impact of the process itself. It is also important to determine which method allows for the better production yield.

Because the precursors are often chemically synthesized or have to be produced in a first step by fermentation, there is no real industrial or financial advantage over the processes of amino acids chemical synthesis.

Production of amino acids by fermentation from natural sources is of course one of the preferred method of producing amino acids. There are indeed numerous bacteria and yeasts which are able to overproduce amino acids under adequate conditions. However, because of the very complex regulation of many of the amino acids syntheses, only a few strains are able to produce relevant amounts of amino acids.

In natural amino acid biosynthesis the amino acid aspartate serves as the precursor for the production of other amino acids, such as lysine, threonine, isoleucine and methionine. Aspartate is produced from oxaloacetate, which is a central metabolite of the citric acid cycle.

A strong production of oxaloacetate is a prerequisite for the industrial production of oxaloacetate-derived amino acids and amino acid derivatives, here-after named oxaloacetate derivatives.

In all cases, candidate oxaloacetate derivatives producer microorganisms have to undergo numerous rounds of mutation and selection before being retained as relevant producers. Illustrative embodiments of candidate methionine-producing microorganisms selected after spontaneous mutation or chemically-induced mutagenesis are disclosed in the U.S. Pat. No. 4,439,525 as well as in Halasz et al. (1996, Periodica Polytechnica Ser. Chem. Engl., Vol. 40(1-2): 53-78).

The production of essential amino acids such as oxaloacetate derivatives through the biosynthetic pathways of bacteria and yeasts requires an important amount of reducing power in the form of NADPH. However, the main pathway for the metabolisation of glucose in these microorganisms, and in particular in yeasts, is glycolysis followed by fermentation which only produces NADH. Maintaining an appropriate NADPH/NADH balance within the microorganism, albeit complex, is therefore essential to optimize bio-production of amino acids and amino acids derivatives of interest while obtaining a viable recombinant microorganism.

The major known bacterial amino acid producer is *C. glutanicum*, a gram-positive, facultative anaerobic, non-pathogenic soil bacterium. *C. glutanicum* is used for the large-scale industrial production of the flavor enhancer L-glutamate as well as of the food additive L-lysine.

There is still a need in the art for transformed, in particular recombinant, microorganisms having at least an increased ability to produce oxaloacetate, thus allowing an increased capacity to produce oxaloacetate-derived amino acids and amino acid derivatives, said oxaloacetate-derived amino acids and amino acid derivatives being termed in the present text oxaloacetate derivatives.

There is still moreover a need for transformed, in particular recombinant, microorganisms having at least an increased ability to produce oxaloacetate, and/or an increased production of pyruvate and/or of acetyl coenzyme A (Acetyl-CoA). There is more particularly a need for transformed, in particular recombinant, microorganisms having at least an increased ability to produce oxaloacetate.

Finally, there is a need for (i) an over-production of NADPH, (ii) a controlled and balanced conversion of phosphoenol pyruvate into oxaloacetate and pyruvate, respectively, (iii) a reduced conversion of pyruvate into ethanol and (iv) a redirection towards conversion of phosphoenol pyruvate into oxaloacetate.

SUMMARY OF THE INVENTION

The present invention accordingly relates to a recombinant yeast, in the genome of which:

(A) at least one nucleic acid encoding a glucose-6-phosphate dehydrogenase is overexpressed and/or is under the control of an inducible or repressible promoter;

(B) at least one nucleic acid encoding a 6-phosphogluconate dehydrogenase, decarboxylating 1 is overexpressed and/or is under the control of an inducible or repressible promoter; and (C) (i) at least one nucleic acid encoding a phosphoenolpyruvate carboxylase that converts phosphoenol pyruvate into oxaloacetate is overexpressed and/or is under the control of an inducible or repressible promoter; and/or (ii) at least one nucleic acid encoding a phosphoenolpyruvate carboxykinase that converts phosphoenol pyruvate PEP into oxaloacetate is overexpressed and/or is under the control of an inducible or repressible promoter.

As illustrated in the enclosed examples, the recombinant yeasts of the invention have an increased ability to produce oxaloacetate which leads to an improved ability to produce oxaloacetate-derived amino acids and amino acid derivatives.

Said advantageous property can be further increased by also recombining the yeast with additional modifications described here-after.

An oxaloacetate derivative-producing recombinant yeast of the invention can consequently advantageously be used in a method for producing oxaloacetate-derived amino acids and amino acid derivatives as described here-after or be used for the production of oxaloacetate-derived amino acids and amino acid derivatives.

The present invention further relates to a method for producing at least one oxaloacetate derivative, said method comprising the steps of:

(a) culturing a recombinant yeast according to the invention in a culture medium; and (b) recovering the oxaloacetate derivative from said culture medium.

Another object of the present invention is the use of a recombinant yeast according to the invention for the production of at least one oxaloacetate derivative.

In a particular embodiment of a method and/or use according to the invention, the said at least one oxaloacetate derivative is selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine and ethyl-homoserine.

In a particular embodiment, the culture medium comprises at least a carbon source, preferably a carbon source selected from the group consisting of glucose and sucrose.

DETAILED DESCRIPTION OF THE INVENTION

The inventors have conceived genetically modified microorganisms, and especially genetically modified yeasts, having an increased ability to produce oxaloacetate, and in particular oxaloacetate-derived amino acids and amino acid derivatives, i.e. oxaloacetate derivatives, as compared to the parent microorganisms, and especially as compared to the parent yeasts.

These genetically modified microorganisms, including these genetically modified yeasts, are described throughout the present specification.

Definitions

As already indicated here-above, an oxaloacetate derivative according to the invention is a metabolite, in particular an amino acid or amino acid derivative, that can be obtained from oxaloacetate after modification by enzymes naturally and/or artificially present in the microorganism producing the oxaloacetate according to the invention, in particular in the yeast producing the oxaloacetate according to the invention.

Examples of such oxaloacetate derivatives can for example be selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine and ethyl-homoserine.

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of oxaloacetate and oxaloacetate derivatives.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

The term "underexpression" means that the expression of a gene or of an enzyme is decreased as compared to the non-modified microorganism. Decreasing the expression of an enzyme is obtained by decreasing the expression of a gene encoding said enzyme. Decreasing the expression of a gene may be carried out by all techniques known by the one skilled in the art. In this regard, it may be notably cited the implementation of a weak promoter upstream the nucleic acid intended to be underexpressed. It may be also cited the implementation of a nucleic acid encoding a variant of the said enzyme that is less active than the parent enzyme or a variant of the said enzyme that is more rapidly degraded in the cell than the parent enzyme. Variants of a parent enzyme that is more rapidly degraded that the said parent enzyme encompass degron-tagged enzymes. It may also be cited the decrease of the expression of a transcription activator of the gene of interest.

The term "inducible promoter" is used to qualify a promoter whose activity is induced, i.e. increased:

- in the presence of one or more particular metabolite(s). The higher the metabolite concentration in the medium, the stronger the promoter activity; or
- in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:

- in the presence of one or more particular metabolite(s). The higher the metabolite concentration in the medium, the weaker the promoter activity; or
- in the presence of a low concentration, or in the absence, of one or more metabolite(s). These metabolites are different from those whose increasing presence represses the activity of the promoter. The lower the metabolite concentration in the medium, the weaker the promoter activity.

A used herein, a "degron-tagged" enzyme means an enzyme comprising an added protein-degradation signal amino acid sequence that serves as a destruction signal that will cause the said enzyme to be the subject of a degradation, which may be either (i) a ubiquitin-independent degradation or (ii) an ubiquitin-dependent degradation. The said added protein-degradation signal, that is also termed "degron" in the art, encompasses an amino acid sequence that serves as a destruction signal, the said amino acid sequence consisting of a transferable degradation signal causing a targeted protein degradation. Degrons encompass "N-degrons", which are transferable N-terminal amino acids that cause the target protein degradation following the well known N-end rule (Bachmair et al., 1986, Science, Vol. 234 (4773): 179-186). The unstable nature of the N-degron is attributed to its first amino acids, which are prone to acetylation or arginylation modifications and ultimately lead to ubiquitination and degradation. Generally, a degron requires at least two components to ensure targeted protein degradation: (i) a target degradation recognition tag, such as a poly-ubiquitin tag and (ii) an unstructured amino acid sequence in close proximity to the degradation recognition tag. For degron-tagging a protein, and especially herein for degron-tagging an enzyme, the one skilled in the art may refer to Yu et al. (2015, Current Opinion in Biotechnology, Vol. 36: 199-204), Cho et al. (2010, Genes & Development, Vol. 24: 438-442), or to Fortmann et al. (2015, J Mol Biol, Vol. 427 (17): 2748-2756), Ravid et al. (2008, Nat Rev Mol Cell Biol, Vol. 9(9): 679-690) and Hochstrasser (1996, Annu Rev Genet, Vol. 30: 405-439).

The "activity" of an enzyme is used interchangeably with the term "function" and designates, in the context of the invention, the capacity of an enzyme to catalyze a desired reaction.

The terms "reduced activity" or "attenuated activity" of an enzyme mean either a reduced specific catalytic activity of the protein obtained by mutation in the amino acids sequence and/or decreased concentrations of the protein in the cell obtained by mutation of the nucleotide sequence or by deletion of the cognate corresponding gene or also by degron-tagging of the protein.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non-modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, (a) disrupted gene(s) in which the above-mentioned DNA construct(s) is/are intended to be inserted may advantageously comprises one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces*, *Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from oxaloacetate. For maximal production of oxaloacetate derivatives, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is glucose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The terms "Aerobic conditions" refers to concentrations of oxygen in the culture medium that are sufficient for an aerobic or facultative anaerobic microorganism to use dioxygene as a terminal electron acceptor.

"Microaerobic condition" refers to a culture medium in which the concentration of oxygen is less than that in air, i.e. oxygen concentration up to 6% 02.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

General Features of Genetic Modifications Introduced According to the Invention

- Genes are over expressed by two kinds of non mutually exclusive modifications:
  - Placing them under the control of a strong promoter; and/or
  - Inserting a plurality of copies of the considered gene.
- All the genome modifications are inserted in yeast according to known genetic engineering techniques:
- The successive genes included in a gene construct that is introduced in the yeast genome according to the invention are of the following structure:

$Prom_1$-$ORF_1$-$term_1$-$ORF_2$-genet-$term_2$- . . . / . . . -$Prom_n$-$ORF_n$-$term_n$, wherein:

- Prom1 is a sequence regulating the expression of the coding sequence ORF1,
- ORF1 is a nucleic acid sequence encoding a desired protein PROT1, and especially a desired enzyme PROT1,
- Term1 is a transcription terminator sequence that mediates transcriptional termination by providing signals in the newly synthesized mRNA that trigger processes which release the mRNA from the transcriptional complex, and
- "1", "2", . . . / . . . "n" may or may not describe the same ORF (Open Reading Frame), promoter or terminator. The order of the genes does not matter. "n" is an integer usually ranging from 5 and 20. These constructs are inserted in one of the yeast chromosome at a controlled location. In some embodiments, the insertion site is not essential for the functionality of the inserted construct, nor for the viability of the resulting genetically modified yeast.
- When the yeast is for example *Saccharomyces cerevisiae*, genes introduced in the yeast genome and originating from other organisms than *Saccharomyces cerevisiae* are generally "transcoded" (generally codon-optimized"), meaning the these genes are synthesized with an optimal codon usage for expression *S. cerevisiae*. The nucleotide sequence (and not the protein sequence) of some genes from *S. cerevisiae* has also been modified ("transcoded") to minimize recombination with an endogenous copy of the said gene.
- Genes may be deleted through standard procedures used in yeast genetic engineering. In some embodiments, the genes targeted for deletion may be interrupted by insertion of one of the above described gene constructs, or alternatively the genes targeted for deletion are replaced by a short stretch of nucleotide.
- Down regulating gene expression may be obtained by disrupting the endogenous copy of the gene and replacing it with a copy of the ORF under the control of a weak promoter. A list and sequences of weak promoters is described elsewhere in the present specification.
- A gene may be rendered "inducible or repressible" by deleting the endogenous copy of the gene (if necessary) and placing a new copy of the ORF under the control of an inducible or repressible promoter. An inducible or repressible promoter is a promoter which activity is modulated and controlled, i.e. either increased or decreased, upon a change in the environmental conditions or external stimuli. Induction or repression may be artificially controlled, which encompasses induction or repression by abiotic factors such as chemical compounds not found naturally in the organism of interest, light, oxygen levels, heat or cold. A list and sequence of inducible or repressible promoters is described elsewhere in the present specification.
- As already specified elsewhere herein, a protein may be underexpressed by destabilization by using "the degron" technology which is described in Yu et al. 2015, (Current Opinion in Biotechnology, Vol. 36: 199-204). In brief this technology consists in introducing in the protein sequence a modification that targets it for degradation. It can consist only in the two first amino acids following the principle known as the N-end rule, or a larger sequence targeting the whole protein to the ubiquitin-proteasome degradation pathway.

Recombinant Yeast According to the Invention

The inventors have conceived recombinant microorganisms, and especially recombinant yeasts, having an increased ability of producing oxaloacetate and in particular oxaloacetate derivatives.

The present invention relates to recombinant yeasts having an increased oxaloacetate derivatives production, and wherein the increased oxaloacetate derivatives production is obtained through a plurality of alterations that have been introduced in the genome thereof, by genetic engineering methods.

This invention pertains to a recombinant yeast, in particular an oxaloacetate derivatives-producing recombinant yeast, in the genome of which:

(A) at least one nucleic acid encoding a glucose-6-phosphate dehydrogenase MET19 is overexpressed and/or is under the control of an inducible or repressible promoter;

(B) at least one nucleic acid encoding a 6-phosphogluconate dehydrogenase, decarboxylating 1 GND1 is overexpressed and/or is under the control of an inducible or repressible promoter; and (C) (i) at least one nucleic acid encoding a phosphoenolpyruvate carboxylase PEPC that converts phosphoenol pyruvate into oxaloacetate is overexpressed and/or is under the control of an inducible or repressible promoter; and/or (ii) at least one nucleic acid encoding a phosphoenolpyruvate carboxykinase PEPCK that converts phosphoenol pyruvate PEP into oxaloacetate is overexpressed and/or is under the control of an inducible or repressible promoter.

The inventors have found that an increased production of oxaloacetate derivatives by yeast cells may be reached by introducing in the genome of these yeast cells a plurality of genetic alterations. As it is fully described herein, the said plurality of genetic alterations encompass an overexpression of certain genes, a controlled expression of certain other genes, as well as repression or deletion of further other genes.

The increased oxaloacetate derivatives production by yeast cells has been reached by the inventors by optimizing the metabolism of glucose, so as to direct the subsequent artificially modified metabolic pathway mainly towards oxaloacetate and optionally acetyl-CoA production, in particular oxaloacetate and acetyl-CoA production, whereas in the same time maintaining an optimal viability of the resulting genetically modified yeast cells.

After a lengthy research time period, the present inventors have determined that a high oxaloacetate derivatives production by yeast cells is obtained by increasing the conversion of phosphoenolpyruvate into oxaloacetate but also by increasing the proportion of NADPH produced with respect to NADH by increasing the flux of glucose-6-phosphate to glyceraldehyde-3-phosphate, and by increasing the production of Acetyl-CoA from acetaldehyde while, notably, maintaining a redox status allowing a good viability of the resulting recombinant yeast cells. The increased availability of these metabolites allows a high oxaloacetate derivatives production, which can further be improved by additional modifications described here-after.

The over-expression of at least one glucose-6-phosphate dehydrogenase-encoding gene (MET19) and of at least one 6-phosphogluconate dehydrogenase decarboxylating 1-encoding gene (GND1) advantageously allows to deflect/divert some of the glycolysis flux into the pentose phosphate pathway, thus increasing the proportion of NADPH produced.

As disclosed in detail in the present specification, the resulting recombinant yeast cells are genetically modified so as to effect an over expression and/or a controlled expression of (i) at least one glucose-6-phosphate dehydrogenase-encoding gene (MET19), of (ii) at least one 6-phosphogluconate dehydrogenase decarboxylating 1-encoding gene (GND1), and of (iii) at least one phosphoenolpyruvate carboxylase-encoding gene (PEPC) that converts phosphoenol pyruvate into oxaloacetate and/or at least one phosphoenolpyruvate carboxykinase-encoding gene (PEPCK) that converts phosphoenol pyruvate PEP into oxaloacetate.

A recombinant yeast according to the invention produces oxaloacetate derivatives with a higher yield than the parent yeast which does not contain the genetic modifications described above.

In some embodiments of a recombinant yeast according to the invention, (i) at least one nucleic acid encoding a transketolase 1 is overexpressed and/or is under the control of an inducible or repressible promoter; and/or (ii) at least one nucleic acid encoding a transaldolase 1 is overexpressed and/or is under the control of an inducible or repressible promoter.

In some embodiments of a recombinant yeast according to the invention, at least one, preferably all, nucleic acid encoding a pyruvate kinase 1 is independently under the control of an inducible or repressible promoter, under the control of a weak promoter and/or in a destabilized form.

In some embodiments of a recombinant yeast according to the invention, (i) at least one, preferably all, nucleic acid encoding a pyruvate kinase 2 PYK2 has been deleted, and/or (ii) at least one, preferably all, nucleic acid encoding a pyruvate kinase 2 PYK2 is under the control of an inducible or repressible promoter and/or is in a destabilized form.

In some embodiments of a recombinant yeast according to the invention:

(A) (i) at least one, preferably all, nucleic acid encoding a pyruvate decarboxylase isozyme 1 has been deleted, and/or (ii) at least one, preferably all, nucleic acid encoding a pyruvate decarboxylase isozyme 1 is under the control of an inducible or repressible promoter and/or is in a destabilized form;

(B) (i) at least one, preferably all, endogenous nucleic acid encoding a pyruvate decarboxylase isozyme 3 has been deleted, and/or (ii) at least one, preferably all, nucleic acid encoding a pyruvate decarboxylase isozyme 3 is under the control of an inducible or repressible promoter and/or is in a destabilized form; and/or (C) (i) at least one, preferably all, nucleic acid encoding a pyruvate decarboxylase isozyme 2 has been deleted, and/or (ii) at least one, preferably all, nucleic acid encoding a pyruvate decarboxylase isozyme 2 is under the control of an inducible or repressible promoter and/or is in a destabilized form.

In some embodiments, the genome of a recombinant yeast of the invention is such that:

(A) (i) at least one, preferably all, nucleic acid encoding an alcohol dehydrogenase 1 has been deleted, and/or (ii) at least one, preferably all, nucleic acid encoding an alcohol dehydrogenase 1 is under the control of an inducible or repressible promoter and/or is in a destabilized form;

(B) (i) at least one, preferably all, nucleic acid encoding an alcohol dehydrogenase 3 has been deleted, and/or (ii) at least one, preferably all, nucleic acid encoding an alcohol dehydrogenase 3 is under the control of an inducible or repressible promoter and/or is in a destabilized form;

(C) (i) at least one, preferably all, nucleic acid encoding an alcohol dehydrogenase 4 has been deleted, and/or (ii) at least one, preferably all, nucleic acid encoding an alcohol dehydrogenase 4 is under the control of an inducible or repressible promoter and/or is in a destabilized form; and/or (D) (i) at least one, preferably all, nucleic acid encoding an alcohol dehydrogenase 5 has been deleted, and/or (ii) at least one, preferably all, nucleic acid encoding an alcohol dehydrogenase 5 is under the control of an inducible or repressible promoter and/or is in a destabilized form.

In some embodiments, the genome of a recombinant yeast of the invention is such that (A) at least one nucleic acid encoding an acetaldehyde-CoA dehydrogenase (MHPF) is overexpressed and/or is under the control of an inducible or repressible promoter; (B) at least one nucleic acid encoding an acetate kinase (AcKA) is overexpressed and/or is under the control of an inducible or repressible promoter; and/or (C) at least one nucleic acid encoding a phosphate acetyl transferase (PTA) is overexpressed and/or is under the control of an inducible or repressible promoter.

In some embodiments, the nucleic acid encoding a glucose-6-phosphate dehydrogenase are nucleic acid belonging to a prokaryotic or eukaryotic organism, in particular to a yeast selected, independently, from the group consisting of *Saccharomyces cerevisiae, Saccharomyces cariocanus, Saccharomyces paradoxus, Saccharomyces mikatae, Saccharomyces bayanus, Saccharomyces pastorianus, Saccharomyces boulardii, Kluveromyces lactis* and *Schizosaccharomyces pombe* and is preferably the nucleic acid from *Saccharomyces cerevisiae.*

In some embodiments, the nucleic acid encoding a 6-phosphogluconate dehydrogenase decarboxylating 1 are nucleic acid from a prokaryotic or eukaryotic organism preferably selected, independently, from the group consisting of *Saccharomyces cerevisiae, Saccharomyces cariocanus, Saccharomyces paradoxus, Saccharomyces mikatae, Saccharomyces bayanus, Saccharomyces pastorianus, Saccharomyces boulardii, Kluveromyces lactis* and *Schizosaccharomyces pombe*, and is preferably the nucleic acid from *Saccharomyces cerevisiae* gene.

In some embodiments, the nucleic acid encoding a phosphoenolpyruvate carboxylase that converts phosphoenol pyruvate PEP into oxaloacetate are nucleic acid from a prokaryote or an eukaryote, in particular from the group consisting of *Escherichia coli, Pseudomonas fluorescens* and *Hyphomicrobium denitrificans*, and is more preferably the *Escherichia coli* PEPC.Ec gene.

In some embodiments, the nucleic acid encoding a 6-phosphogluconate dehydrogenase decarboxylating 1 are nucleic acid from a prokaryotic or eukaryotic organism preferably selected, independently, from the group consisting of *Saccharomyces cerevisiae, Saccharomyces cariocanus, Saccharomyces paradoxus, Saccharomyces mikatae, Saccharomyces bayanus, Saccharomyces pastorianus, Saccharomyces boulardii, Kluveromyces lactis* and *Schizosaccharomyces pombe.*

In some embodiments, the nucleic acid encoding a phosphoenolpyruvate carboxykinase enzyme are nucleic acid from a prokaryote or an eukaryote, in particular from the group consisting of *Escherichia coli, Pseudomonas fluorescens, Mycobacterium tuberculosis, Anaerobiospirillum succiniciproducens, Succinatimoras hippie, Bacteroides salyersiae, Trypanosoma cruzi* and *Clostridium thermocellum*, and is more preferably the *Escherichia coli* PEPCK.Ec gene.

In some embodiments, the recombinant yeast is selected from the group consisting of the genus *Saccharomyces, Candida, Ashbya, Dekkera, Pichia* (*Hansenula*), *Debaryomyces, Clavispora, Lodderomyces, Yarrowia, Schizosaccharomyces, Cryptococcus* and *Malassezia*, in particular from the group consisting of the genus *Saccharomyces, Pichia, Candida* or *Yarrowia*, preferably from the group consisting of the species *Saccharomyces cerevisiae, Saccharomyces boulardii, Saccharomyces douglasii, Saccharomyces bayanus* and *Candida sorensis*, and is more preferably the *Saccharomyces cerevisiae* species.

Glucose-6-Phosphate Dehydrogenase-Encoding Gene Over Expression and/or Controlled Expression In preferred embodiments of a recombinant yeast according to the invention, over expression of a glucose-6-phosphate dehydrogenase-encoding gene is obtained by inserting, at selected location(s) of the yeast genome, one or more copies of an expression cassette comprising a glucose-6-phosphate dehydrogenase coding sequence. Glucose-6-phosphate dehydrogenase and a glucose-6-phosphate dehydrogenase-encoding gene that are encompassed by the invention are detailed elsewhere in the present specification.

In some of these embodiments, the said one or more copies of an expression cassette comprising a glucose-6-phosphate dehydrogenase coding sequence comprise(s) regulatory sequences allowing a strong expression of the glucose-6-phosphate dehydrogenase, such as a strong promoter that is functional in yeast cells.

In addition to or as an alternative to these embodiments of a recombinant yeast according to the invention, at least one glucose-6-phosphate dehydrogenase-encoding gene can be under the control of an inducible or repressible promoter that is functional in yeast cells.

Without wishing to be bound by any particular theory, the inventors believe that over expression of a glucose-6-phosphate dehydrogenase may enhance the conversion of the intermediate glucose-6-phosphate into 6-phosphoglucono-lactone and enhance the proportion of NADPH produced compared to the proportion of NADH. The same applies when at least one glucose-6-phosphate dehydrogenase coding sequence is under the control of an inducible or repressible promoter.

In some preferred embodiments, the said glucose-6-phosphate dehydrogenase-encoding gene is the MET19 gene from *Saccharomyces cerevisiae* as shown in the examples herein and discussed previously.

In preferred embodiments, the said glucose-6-phosphate dehydrogenase-encoding gene is placed under the control of the strong promoter pENO2 or of the inducible or repressible promoter pCUP1-1.

Illustratively, the glucose-6-phosphate dehydrogenase gene may be inserted within the MET19 gene and/or within the PYK1 gene, as it is shown in the examples herein.

6-Phosphogluconate Dehydrogenase, Decarboxylating 1-Encoding Gene Over Expression and/or Controlled Expression In preferred embodiments of a recombinant yeast according to the invention, over expression of a 6-phosphogluconate dehydrogenase, decarboxylating 1-encoding gene is obtained by inserting, at selected location(s) of the yeast genome, one or more copies of an expression cassette comprising a 6-phosphogluconate dehydrogenase, decarboxylating 1 coding sequence. 6-phosphogluconate dehydrogenase, decarboxylating 1 enzyme and a 6-phosphogluconate dehydrogenase, decarboxylating 1-encoding gene that are encompassed by the invention are detailed elsewhere in the present specification.

In some of these embodiments, the said one or more copies of an expression cassette comprising a 6-phosphogluconate dehydrogenase, decarboxylating 1 coding sequence comprise(s) regulatory sequences allowing a strong expression of the 6-phosphogluconate dehydrogenase, decarboxylating 1, such as a strong promoter that is functional in yeast cells.

In addition to or as an alternative to these embodiments of a recombinant yeast according to the invention, at least one 6-phosphogluconate dehydrogenase, decarboxylating 1-encoding gene can be under the control of an inducible or repressible promoter that is functional in yeast cells.

Without wishing to be bound by any particular theory, the inventors believe that over expression of a 6-phosphogluconate dehydrogenase, decarboxylating 1 may enhance the conversion of the intermediate 6-phosphogluconate into ribulose 5-phosphate and enhance the proportion of NADPH produced compared to the proportion of NADH. The same applies when at least one 6-phosphogluconate dehydrogenase, decarboxylating 1 coding sequence is under the control of an inducible or repressible promoter.

In some preferred embodiments, the said 6-phosphogluconate dehydrogenase, decarboxylating 1-encoding gene is the GND1 gene from *Saccharomyces cerevisiae* as shown in the examples herein and discussed previously.

In preferred embodiments, the said 6-phosphogluconate dehydrogenase, decarboxylating 1-encoding gene is placed under the control of the strong promoter pTEF3.

Illustratively, the 6-phosphogluconate dehydrogenase, decarboxylating 1 gene may be inserted within the MET19 gene, as it is shown in the examples herein.

Phosphoenolpyruvate Carboxylase-Encoding Gene Over Expression and/or Controlled Expression In preferred embodiments of a recombinant yeast according to the invention, over expression of a phosphoenolpyruvate carboxylase-encoding gene that converts phosphoenol pyruvate into oxaloacetate is obtained by inserting, at selected location(s) of the yeast genome, one or more copies of an expression cassette comprising a phosphoenolpyruvate carboxylase coding sequence, this phosphoenolpyruvate carboxylase converting phosphoenol pyruvate into oxaloacetate. Phosphoenolpyruvate carboxylase and a phosphoenolpyruvate carboxylase-encoding gene that are encompassed by the invention, and that converts phosphoenol pyruvate into oxaloacetate are detailed elsewhere in the present specification.

In some of these embodiments, the said one or more copies of an expression cassette comprising a phosphoenolpyruvate carboxylase coding sequence comprise(s) regulatory sequences allowing a strong expression of the phosphoenolpyruvate carboxylase, such as a strong promoter that is functional in yeast cells.

In addition to or as an alternative to these embodiments of a recombinant yeast according to the invention, at least one phosphoenolpyruvate carboxylase-encoding gene can be under the control of an inducible or repressible promoter that is functional in yeast cells.

Without wishing to be bound by any particular theory, the inventors believe that over expression of a phosphoenolpyruvate carboxylase may enhance the conversion of the intermediate metabolite phosphoenolpyruvate (PEP) into oxaloacetate. The same applies when at least one phosphoenolpyruvate carboxylase coding sequence is under the control of an inducible or repressible promoter.

In some preferred embodiments, the said phosphoenolpyruvate carboxylase-encoding gene is the PEPC or PPC gene from *Escherichia coli.*

In preferred embodiments, the said phosphoenolpyruvate carboxylase-encoding gene is placed under the control of the strong promoter pTDH3 or of the inducible or repressible promoter pACU3p.

Illustratively, the phosphoenolpyruvate carboxylase gene may be inserted within the URA3 gene and/or within the TRP1 gene.

Phosphoenolpyruvate Carboxykinase-Encoding Gene Over Expression and/or Controlled Expression In preferred embodiments of a recombinant yeast according to the invention, over expression of a phosphoenolpyruvate carboxykinase-encoding gene that converts phosphoenol pyruvate into oxaloacetate is obtained by inserting, at selected location(s) of the yeast genome, one or more copies of an expression cassette comprising a phosphoenolpyruvate carboxykinase coding sequence that converts phosphoenol pyruvate into oxaloacetate. Phosphoenolpyruvate carboxykinase and a phosphoenolpyruvate carboxykinase-encoding gene that are encompassed by the invention convert phosphoenol pyruvate into oxaloacetate and are detailed elsewhere in the present specification.

In some of these embodiments, the said one or more copies of an expression cassette comprising a phosphoenolpyruvate carboxykinase coding sequence comprise(s) regulatory sequences allowing a strong expression of the phosphoenolpyruvate carboxykinase, such as a strong promoter that is functional in yeast cells.

In addition to or as an alternative to these embodiments of a recombinant yeast according to the invention, at least one phosphoenolpyruvate carboxykinase-encoding gene can be under the control of an inducible or repressible promoter that is functional in yeast cells.

Without wishing to be bound by any particular theory, the inventors believe that over expression of a phosphoenolpyruvate carboxykinase may enhance the conversion of the intermediate metabolite phosphoenolpyruvate (PEP) into oxaloacetate. The same applies when at least one phosphoenolpyruvate carboxykinase coding sequence is under the control of an inducible or repressible promoter.

In some preferred embodiments, the said phosphoenolpyruvate carboxykinase-encoding gene is the PEPCK gene from *Escherichia coli.*

In preferred embodiments, the said phosphoenolpyruvate carboxykinase-encoding gene is placed under the control of the inducible or repressible promoter pACU1.

Illustratively, the phosphoenolpyruvate carboxykinase gene may be inserted within the PYK1 gene, as illustrated in the examples.

Glucose-6-Phosphate Dehydrogenase (MET19)

The glucose-6-phosphate dehydrogenase is a protein which is known in the art to catalyze the $NADP^+$-dependent formation of 6-phosphate-D-glucono-1,5-lactone and NADPH from D-glucose-6-phosphate. The glucose-6-phosphate dehydrogenase encoded by the genome of *Saccharomyces cerevisiae* may be termed MET19.

Accordingly, the production of NADPH by MET19 advantageously compensates the consumption of NADPH and production of NADH in the glycolysis.

A method implemented to measure the activity level of glucose-6-phosphate dehydrogenase belongs to the general knowledge of the one skilled in the art.

In this regard, the one skilled in the art may advantageously refer to the method described by Kuby S. and Noltmann E. A (1966) Dehydrogenases and Oxidases Methods in Enzymology 9, 116-117.

Preferred glucose-6-phosphate dehydrogenase in the present specification is an enzyme having an EC number 1.1.1.49.

According to a preferred embodiment, the nucleic acid(s) encoding a glucose-6-phosphate dehydrogenase may be nucleic acid(s) originating from organisms preferably selected in a group comprising prokaryotic organisms and eukaryotic organisms. In some embodiments, the nucleic acid(s) encoding a glucose-6-phosphate dehydrogenase may be nucleic acid(s) originating from archaebacteria. In some preferred embodiments, the nucleic acid(s) encoding a glucose-6-phosphate dehydrogenase may be nucleic acid(s) originating from yeast, and especially from *Saccharomyces cerevisiae.*

According to a yet preferred embodiment, the nucleic acid(s) encoding a glucose-6-phosphate dehydrogenase may be nucleic acid(s) selected from the group consisting of sequences having at least 30%, advantageously at least 65%, preferably at least 80%, nucleic acid identity with a nucleic acid selected in a group consisting of the reference nucleic acid sequences of SEQ ID NO: 1 and also a biological activity of the same nature. The nucleic acids of SEQ ID NO: 1 encode a glucose-6-phosphate dehydrogenase originating from *Saccharomyces cerevisiae*, that may also be collectively termed MET19.

A biological activity of the same nature regarding this sequence is the capacity to code for an enzyme that catalyzes the $NADP^+$-dependent formation of 6-phosphate-D-glucono-1,5-lactone and NADPH from D-glucose-6-phosphate.

As described herein, a nucleic acid sequence having at least 30% nucleotide identity with a reference nucleic acid sequence encompasses nucleic acid sequences having at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the glucose-6-phosphate dehydrogenase from *Saccharomyces cerevisiae*, the one skilled in the art may refer to the accession number NP014158.1 in the UniProt database, or to SEQ ID NO. 2 described herein.

According to another particular embodiment, the nucleic acid(s) encoding a glucose-6-phosphate dehydrogenase may be nucleic acid(s) encoding an amino acid sequence selected from the group consisting of sequences having at least 30%, advantageously at least 65%, preferably at least 80%, amino acid identity with the amino acid sequence of SEQ ID NO: 2, and also a biological activity of the same nature.

A biological activity of the same nature regarding this sequence is as described previously, i.e. the capacity to catalyze the $NADP^+$-dependent formation of 6-phosphate-D-glucono-1,5-lactone and NADPH from D-glucose-6-phosphate.

As described herein, an amino acid sequence having at least 30% amino acid identity with a reference nucleic acid sequence encompasses amino acid sequences having at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the glucose-6-phosphate dehydrogenase in the present invention is regulated by at least one promoter and at least one terminator, such as herein after defined more in details, which are present in 5' and 3' position respectively of the nucleic acid sequence encoding the said glucose-6-phosphate dehydrogenase.

As it is specified elsewhere in the present description, the glucose-6-phosphate dehydrogenase is overexpressed and/or under the control of an inducible or repressible promoter in a recombinant yeast according to the invention.

In some embodiments, overexpression of the glucose-6-phosphate dehydrogenase may result from the control of the corresponding gene by a strong promoter within the said recombinant yeast.

In some other embodiments, overexpression of the glucose-6-phosphate dehydrogenase may result from the presence of a plurality of copies of a glucose-6-phosphate dehydrogenase-encoding sequence within the genome of the said recombinant yeast.

In still further embodiments, overexpression of the glucose-6-phosphate dehydrogenase may result from both (i) the control of the corresponding gene by a strong promoter within the said recombinant yeast and (ii) the presence of a plurality of copies of a glucose-6-phosphate dehydrogenase-encoding sequence within the genome the said recombinant yeast.

6-Phosphogluconate Dehydrogenase Decarboxylating 1 (GND1)

The 6-phosphogluconate dehydrogenase decarboxylating 1 is a protein which is described in the art for catalyzing the $NADP^+$-dependent formation of ribulose 5-phosphate and $CO_2$ and NADPH from 6-phosphogluconate. The 6-phosphogluconate dehydrogenase decarboxylating 1 encoded by the genome of *Saccharomyces cerevisiae* may be termed GND1.

Accordingly, the production of NADPH by GND1 advantageously compensates the consumption of NADPH and production of NADH in the glycolysis.

A method implemented to measure the activity level of 6-phosphogluconate dehydrogenase decarboxylating 1 belongs to the general knowledge of the one skilled in the art.

In this regard, the one skilled in the art may advantageously refer to the method described by He W., Wang Y., Liu W. and Zhou C. Z. (2007) BMC Structural Biology, 7:38.

Preferred 6-phosphogluconate dehydrogenase decarboxylating 1 in the present specification is an enzyme having an EC number of no EC 1.1.1.44.

According to a preferred embodiment, the nucleic acid(s) encoding a 6-phosphogluconate dehydrogenase decarboxylating 1 may be nucleic acid(s) originating from organisms preferably selected in a group comprising prokaryotic organisms and eukaryotic organisms. In some embodiments, the nucleic acid(s) encoding a 6-phosphogluconate dehydrogenase decarboxylating 1 may be nucleic acid(s) originating from archaebacteria. In some embodiments, the nucleic acid(s) encoding a 6-phosphogluconate dehydrogenase decarboxylating 1 may be nucleic acid(s) originating from organisms preferably selected from yeasts. In some other preferred embodiments, the nucleic acid(s) encoding a 6-phosphogluconate dehydrogenase decarboxylating 1 may be nucleic acid(s) originating from *Saccharomyces cerevisiae.*

According to a yet preferred embodiment, the nucleic acid(s) encoding a 6-phosphogluconate dehydrogenase decarboxylating 1 may be nucleic acid(s) selected from the group consisting of sequences having at least 24%, advantageously at least 65%, preferably at least 80%, nucleic acid identity with a nucleic acid of SEQ ID NO: 3, and also a biological activity of the same nature. The nucleic acid of SEQ ID NO: 3 encodes a 6-phosphogluconate dehydrogenase decarboxylating 1 originating from *Saccharomyces cerevisiae*, that may also be termed GND1.

A biological activity of the same nature regarding this sequence is the capacity to code for an enzyme that catalyzes the $NADP^+$-dependent formation of ribulose 5-phosphate and $CO_2$ and NADPH from 6-phosphogluconate.

As described herein, a nucleic acid sequence having at least 24% nucleotide identity with a reference nucleic acid sequence encompasses nucleic acid sequences having at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the 6-phosphogluconate dehydrogenase decarboxylating 1 from *Saccharomyces cerevisiae*, the one skilled in the art may refer to the accession number NP012053.3 in the UniProt database, or to SEQ ID NO. 4 described herein.

According to another particular embodiment, the nucleic acid(s) encoding 6-phosphogluconate dehydrogenase decarboxylating 1 may be nucleic acid(s) encoding an amino acid sequence selected from the group consisting of sequences having at least 24%, advantageously at least 65%, preferably at least 80%, amino acid identity with the amino acid sequence of SEQ ID NO: 4, and also a biological activity of the same nature. Illustratively, the 6-phosphogluconate dehydrogenase decarboxylating 1 originating from *Capronia semi-immersa* has 24% amino acid identity with the 6-phosphogluconate dehydrogenase decarboxylating 1 of SEQ ID NO. 4.

A biological activity of the same nature regarding this sequence is as described previously, i.e. the capacity to catalyze the $NADP^+$-dependent formation of ribulose 5-phosphate and $CO_2$ and NADPH from 6-phosphogluconate.

As described herein, an amino acid sequence having at least 24% amino acid identity with a reference nucleic acid sequence encompasses amino acid sequences having at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the 6-phosphogluconate dehydrogenase decarboxylating 1 in the present invention is regulated by at least one promoter and at least one terminator, such as herein after defined more in details, which are present in 5' and 3' position respectively of the nucleic acid sequence encoding the said 6-phosphogluconate dehydrogenase decarboxylating 1.

As it is specified elsewhere in the present description, the strong 6-phosphogluconate dehydrogenase decarboxylating 1 expression shall be controlled in a recombinant yeast according to the invention.

In preferred embodiments, the controlled strong expression of the 6-phosphogluconate dehydrogenase decarboxylating 1 is performed by placing the 6-phosphogluconate dehydrogenase decarboxylating 1-encoding nucleic acid sequence under the control of an appropriate inducible or repressible promoter, preferably a strong inducible or repressible promoter.

Phosphoenolpyruvate Carboxylase (PEPC)

The phosphoenolpyruvate carboxylase is a protein which is described in the art for catalyzing the conversion of phosphoenolpyruvate into oxaloacetate. The phosphoenolpyruvate carboxylase encoded by the genome of *E. coli* may be termed PEPC or PPC.

A method implemented to measure the activity level of phosphoenolpyruvate carboxylase belongs to the general knowledge of the one skilled in the art.

In this regard, the one skilled in the art may advantageously refer to the method described by Bazaes S. et al. (2007) The Protein Journal, 26, 265-269 and Mariët J. Van der Werf et al. (1997) Arch Microbiol 167: 332-342.

Preferred phosphoenolpyruvate carboxylase in the present specification is an enzyme having an EC number of no 4.1.1.31.

According to a preferred embodiment, the nucleic acid(s) encoding a phosphoenolpyruvate carboxylase may be nucleic acid(s) originating from organisms preferably selected in a group comprising prokaryotic organisms and eukaryotic organisms. In some embodiments, the nucleic acid(s) encoding a phosphoenolpyruvate carboxylase may be nucleic acid(s) originating from archaebacteria. In some embodiments, the nucleic acid(s) encoding a phosphoenolpyruvate carboxylase may be nucleic acid(s) originating from organisms preferably selected from bacteria. In some other preferred embodiments, the nucleic acid(s) encoding a phosphoenolpyruvate carboxylase may be nucleic acid(s) originating from *Escherichia coli.*

According to a yet preferred embodiment, the nucleic acid(s) encoding a phosphoenolpyruvate carboxylase may be nucleic acid(s) selected from the group consisting of sequences having at least 25%, advantageously at least 65%, preferably at least 80%, nucleic acid identity with a nucleic acid of SEQ ID NO: 5, and also a biological activity of the same nature.

A biological activity of the same nature regarding this sequence is the capacity to code for an enzyme that catalyzes the conversion of phosphoenolpyruvate into oxaloacetate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the phosphoenolpyruvate carboxylase from *E. coli*, the one skilled in the art may refer to the accession number WP 032179661 in the NCBI database, or to SEQ ID NO. 6 described herein.

According to another particular embodiment, the nucleic acid(s) encoding phosphoenolpyruvate carboxylase may be nucleic acid(s) encoding an amino acid sequence selected from the group consisting of sequences having at least 25%, advantageously at least 65%, preferably at least 80%, amino acid identity with the amino acid sequence of SEQ ID NO: 6, and also a biological activity of the same nature. Illustratively, the phosphoenolpyruvate carboxylase originating from *cyanothece* sp. PCC782 has 29% amino acid identity with the malate dehydrogenase of SEQ ID NO. 6.

A biological activity of the same nature regarding this sequence is as described previously, i.e. the capacity to catalyze the conversion of phosphoenolpyruvate into oxaloacetate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the phosphoenolpyruvate carboxylase in the present invention is regulated by at least one promoter and at least one terminator, such as herein after defined more in details, which are present in 5' and 3' position respectively of the nucleic acid sequence encoding the said phosphoenolpyruvate carboxylase.

As it is specified elsewhere in the present description, the strong phosphoenolpyruvate carboxylase expression shall be controlled in a recombinant yeast according to the invention.

In preferred embodiments, the controlled strong expression of the phosphoenolpyruvate carboxylase is performed by placing the phosphoenolpyruvate carboxylase-encoding nucleic acid sequence under the control of an appropriate inducible or repressible promoter, preferably a strong inducible or repressible promoter.

Phosphoenolpyruvate Carboxykinase (PEPCK)

The phosphoenolpyruvate carboxykinase is a protein which is described in the art for catalyzing the conversion of phosphoenolpyruvate into oxaloacetate. The phosphoenolpyruvate carboxykinase encoded by the genome of *E. coli* may be termed PEPCK.

A method implemented to measure the activity level of phosphoenolpyruvate carboxykinase belongs to the general knowledge of the one skilled in the art.

In this regard, the one skilled in the art may advantageously refer to the method described by Bazaes S. et al. (2007) The Protein Journal, 26, 265-269 and Mariët J. Van der Werf et al. (1997) Arch Microbiol 167: 332-342.

Preferred phosphoenolpyruvate carboxykinase in the present specification is an enzyme having an EC number of no 4.1.1.49.

According to a preferred embodiment, the nucleic acid(s) encoding a phosphoenolpyruvate carboxykinase may be nucleic acid(s) originating from organisms preferably selected in a group comprising prokaryotic organisms and eukaryotic organisms. In some embodiments, the nucleic acid(s) encoding a phosphoenolpyruvate carboxykinase may be nucleic acid(s) originating from archaebacteria. In some embodiments, the nucleic acid(s) encoding a phosphoenolpyruvate carboxykinase may be nucleic acid(s) originating from organisms preferably selected from bacteria. In some other preferred embodiments, the nucleic acid(s) encoding a phosphoenolpyruvate carboxykinase may be nucleic acid(s) originating from *Escherichia coli.*

According to a yet preferred embodiment, the nucleic acid(s) encoding a phosphoenolpyruvate carboxykinase may be nucleic acid(s) selected from the group consisting of sequences having at least 20%, advantageously at least 65%, preferably at least 80%, nucleic acid identity with a nucleic acid of SEQ ID NO: 7, and also a biological activity of the same nature.

A biological activity of the same nature regarding this sequence is the capacity to code for an enzyme that catalyzes the conversion of phosphoenolpyruvate into oxaloacetate while phosphorylating an ADP into ATP.

As described herein, a nucleic acid sequence having at least 20% nucleotide identity with a reference nucleic acid sequence encompasses nucleic acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the phosphoenolpyruvate carboxykinase from *E. coli*, the one skilled in the art may refer to the accession number NP013023.3 in the UniProt database, or to SEQ ID NO. 8 described herein.

According to another particular embodiment, the nucleic acid(s) encoding phosphoenolpyruvate carboxykinase may be nucleic acid(s) encoding an amino acid sequence selected from the group consisting of sequences having at least 20%, advantageously at least 65%, preferably at least 80%, amino acid identity with the amino acid sequence of SEQ ID NO: 8, and also a biological activity of the same nature. Illustratively, the phosphoenolpyruvate carboxykinase originating from *Streptococcus gorgonii* has 22% amino acid identity with the phosphoenolpyruvate carboxykinase of SEQ ID NO. 8.

A biological activity of the same nature regarding this sequence is as described previously, i.e. the capacity to catalyze the conversion of phosphoenolpyruvate into oxaloacetate.

As described herein, an amino acid sequence having at least 20% amino acid identity with a reference nucleic acid sequence encompasses amino acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the phosphoenolpyruvate carboxykinase in the present invention is regulated by at least one promoter and at least one terminator, such as herein after defined more in details, which are present in 5' and 3' position respectively of the nucleic acid sequence encoding the said phosphoenolpyruvate carboxykinase.

As it is specified elsewhere in the present description, the strong phosphoenolpyruvate carboxykinase expression shall be controlled in a recombinant yeast according to the invention.

In preferred embodiments, the controlled strong expression of the phosphoenolpyruvate carboxykinase is performed by placing the phosphoenolpyruvate carboxykinase-encoding nucleic acid sequence under the control of an appropriate inducible or repressible promoter, preferably a strong inducible or repressible promoter.

Specific Embodiments of a Oxaloacetate Derivatives-Producing Recombinant Yeast

Transketolase 1-Encoding Gene Over Expression and/or Controlled Expression

In preferred embodiments of a recombinant yeast according to the invention, over expression of a transketolase 1-encoding gene is obtained by inserting, at selected location(s) of the yeast genome, one or more copies of an expression cassette comprising a transketolase 1 coding sequence. Transketolase 1 and a transketolase 1-encoding gene that are encompassed by the invention are detailed elsewhere in the present specification.

In some of these embodiments, the said one or more copies of an expression cassette comprising a transketolase 1 coding sequence comprise(s) regulatory sequences allowing a strong expression of the transketolase 1, such as a strong promoter that is functional in yeast cells.

In addition to or as an alternative to these embodiments of a recombinant yeast according to the invention, at least one transketolase 1-encoding gene can be under the control of an inducible or repressible promoter that is functional in yeast cells.

Without wishing to be bound by any particular theory, the inventors believe that over expression of a transketolase 1 may enhance conversion of ribose 5-Phosphate and xylose 5-Phosphate into sedoheptulose 7-phosphate and Glyceraldehyde 3-phosphate and enhance the proportion of NADPH produced compared to the proportion of NADH. The same applies when at least one transketolase 1 coding sequence is under the control of an inducible or repressible promoter.

In some preferred embodiments, the said transketolase 1-encoding gene is the TKL1 gene from *Saccharomyces cerevisiae.*

Transaldolase 1-Encoding Gene Over Expression and/or Controlled Expression

In preferred embodiments of a recombinant yeast according to the invention, over expression of a transaldolase 1-encoding gene is obtained by inserting, at selected location(s) of the yeast genome, one or more copies of an expression cassette comprising a transaldolase 1 coding sequence. Transaldolase 1 and a transaldolase 1-encoding gene that are encompassed by the invention are detailed elsewhere in the present specification.

In some of these embodiments, the said one or more copies of an expression cassette comprising a transaldolase 1 coding sequence comprise(s) regulatory sequences allowing a strong expression of the transaldolase 1, such as a strong promoter that is functional in yeast cells.

In addition to or as an alternative to these embodiments of a recombinant yeast according to the invention, at least one transaldolase 1-encoding gene can be under the control of an inducible or repressible promoter that is functional in yeast cells.

Without wishing to be bound by any particular theory, the inventors believe that over expression of a transaldolase 1 may enhance conversion of the sedoheptulose 7-phosphate and Glyceraldehyde 3-phosphate into erythrose 4-phosphate and Fructose 6-phosphate and enhance the proportion of NADPH produced compared to the proportion of NADH. The same applies when at least one transaldolase 1 coding sequence is under the control of an inducible or repressible promoter.

In some preferred embodiments, the said transaldolase 1-encoding gene is the TAL1 gene from *Saccharomyces cerevisiae.*

Under Expression of Pyruvate Kinase 1

In a preferred embodiment, a recombinant yeast according to the invention is further defined as having a genome in which at least one, preferably all, nucleic acid encoding a pyruvate kinase 1 PYK1 is independently:

- under the control of an inducible or repressible promoter;
- under the control of a weak promoter; and/or
- in a destabilized form.

Without wishing to be bound by any particular theory, the inventors believe that an under expression of a pyruvate kinase 1 gene shall increase oxaloacetate production by the recombinant yeast by reducing the consumption of the produced phosphoenolpyruvate (PEP) by its conversion into pyruvate.

In some embodiments, under expression of pyruvate kinase 1 may be rendered conditional, for example by placing the expression of this gene under the control of repressible regulatory sequences, such as inducible or repressible promoters.

Methods for repressing gene expression are well known from the one skilled in the art.

Pyruvate kinase 1 under expression also encompasses the insertion of a nucleic acid encoding a destabilized pyruvate kinase 1. A destabilized pyruvate kinase 1 is a variant of pyruvate kinase 1 that is more rapidly degraded within the yeast cell than the parent pyruvate kinase 1.

In preferred embodiments, a destabilized pyruvate kinase 1 consists of a degron-tagged pyruvate kinase 1 protein.

A method implemented to measure the activity level of pyruvate kinase 1 belongs to the general knowledge of the one skilled in the art.

In this regard, the one skilled in the art may advantageously refer to the method described by Susan-resiga and Nowak (2004) Biochemistry 43, 15230-15245).

Preferred pyruvate kinase 1 in the present specification is an enzyme having an EC number of no 2.7.1.40.

According to a preferred embodiment, the nucleic acid(s) encoding a pyruvate kinase 1 may be nucleic acid(s) originating from organisms preferably selected in a group comprising prokaryotic organisms and eukaryotic organisms. In some preferred embodiments, the nucleic acid(s) encoding a pyruvate kinase 1 may be nucleic acid(s) originating from a yeast, and especially from *Saccharomyces cerevisiae.*

According to a particular embodiment, the nucleic acid(s) encoding a pyruvate kinase 1 may be nucleic acid of SEQ ID NO: 13. The nucleic acid of SEQ ID NO: 13 encodes a pyruvate kinase 1 originating from *Saccharomyces cerevisiae*, that may also be termed PYK1.

For the amino acid sequence of the pyruvate kinase 1 from *Saccharomyces cerevisiae*, the one skilled in the art may refer to the accession number NP009362.1 in the UniProt database, or to SEQ ID NO. 14 described herein.

As above-mentioned, the expression level of the pyruvate kinase 1 in the present invention is regulated by at least one promoter and at least one terminator, such as herein after defined more in details, which are present in 5' and 3' position respectively of the nucleic acid sequence encoding the said pyruvate kinase 1.

As it is specified elsewhere in the present description, in some embodiments of the invention, the pyruvate kinase 1 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Kinase 2

In preferred embodiments of a recombinant yeast according to the invention, the recombinant yeast is furthermore defined as having a genome in which:

(i) at least one, preferably all, nucleic acid encoding a pyruvate kinase 2 PYK2 has been deleted, and/or (ii) at least one, preferably all, nucleic acid encoding a pyruvate kinase 2 PYK2 is under the control of an inducible or repressible promoter and/or is in a destabilized form.

Without wishing to be bound by any particular theory, the inventors believe that an under expression of a pyruvate kinase 2 gene shall reduce the consumption of the produced pyruvate into oxaloacetate.

In some embodiments, under expression of pyruvate kinase 2 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate kinase 2 under expression also encompasses the insertion of a nucleic acid encoding a destabilized pyruvate kinase 2. A destabilized pyruvate kinase 2 is a variant of pyruvate kinase 2 that is more rapidly degraded within the yeast cell than the parent pyruvate kinase 2.

In preferred embodiments, a destabilized pyruvate kinase 2 consists of a degron-tagged pyruvate kinase 2 protein.

For example, the pyruvate kinase 2 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of pyruvate kinase 2 belongs to the general knowledge of the one skilled in the art.

In this regard, the one skilled in the art may advantageously refer to the method described by Susan-resiga and Nowak (2004) Biochemistry 43, 15230-15245).

Preferred pyruvate kinase 2 in the present specification is an enzyme having an EC number of no 2.7.1.40.

According to a preferred embodiment, the nucleic acid(s) encoding a pyruvate kinase 2 may be nucleic acid(s) originating from organisms preferably selected in a group comprising prokaryotic organisms and eukaryotic organisms. In some preferred embodiments, the nucleic acid(s) encoding a pyruvate kinase 2 may be nucleic acid(s) originating from a yeast, and especially from *Saccharomyces cerevisiae.*

According to a particular embodiment, the nucleic acid(s) encoding a pyruvate kinase 2 may be nucleic acid of SEQ ID NO: 15. The nucleic acid of SEQ ID NO: 15 encodes a pyruvate kinase 2 originating from *Saccharomyces cerevisiae*, that may also be termed PYK2.

For the amino acid sequence of the pyruvate kinase 2 from *Saccharomyces cerevisiae*, the one skilled in the art may refer to the accession number NP014992.3 in the UniProt database, or to SEQ ID NO. 16 described herein.

As above-mentioned, the expression level of the pyruvate kinase 2 in the present invention is regulated by at least one promoter and at least one terminator, such as herein after defined more in details, which are present in 5' and 3' position respectively of the nucleic acid sequence encoding the said pyruvate kinase 2.

As it is specified elsewhere in the present description, in some embodiments of the invention, the pyruvate kinase 2 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Decarboxylase Isozyme 1

In preferred embodiments of a recombinant yeast according to the invention, the recombinant yeast is furthermore defined as having a genome in which:

(i) at least one, preferably all, nucleic acid encoding a pyruvate decarboxylase isozyme 1 PDC1 has been deleted, and/or (ii) at least one, preferably all, nucleic acid encoding a pyruvate decarboxylase isozyme 1 PDC1 is under the control of an inducible or repressible promoter and/or is in a destabilized form.

Without wishing to be bound by any particular theory, the inventors believe that an under expression of a pyruvate decarboxylase isozyme 1 gene shall reduce the flux from pyruvate to ethanol by reducing the consumption of the produced pyruvate into acetaldehyde.

In some embodiments, under expression of pyruvate decarboxylase isozyme 1 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate decarboxylase isozyme 1 under expression also encompasses the insertion of a nucleic acid encoding a destabilized pyruvate decarboxylase isozyme 1. A destabilized pyruvate decarboxylase isozyme 1 is a variant of pyruvate decarboxylase isozyme 1 that is more rapidly degraded within the yeast cell than the parent pyruvate decarboxylase isozyme 1.

In preferred embodiments, a destabilized pyruvate decarboxylase isozyme 1 consists of a degron-tagged pyruvate decarboxylase isozyme 1 protein.

For example, the pyruvate decarboxylase isozyme 1 gene can be interrupted by loxP, or for example by URA3.Kl-loxP, and is thus deleted (which can also be termed inactivated). It can alternatively be interrupted by a cassette comprising genes of interest, as illustrated in the examples as filed.

A method implemented to measure the activity level of pyruvate decarboxylase isozyme 1 belongs to the general knowledge of the one skilled in the art.

In this regard, the one skilled in the art may advantageously refer to the method described by Wang et al. (Biochemistry, 2001, 40: 1755-1763).

Preferred pyruvate decarboxylase isozyme 1 in the present specification is an enzyme having an EC number of no 4.1.1.1.

According to a preferred embodiment, the nucleic acid(s) encoding a pyruvate decarboxylase isozyme 1 may be nucleic acid(s) originating from organisms preferably selected in a group comprising prokaryotic organisms and eukaryotic organisms. In some preferred embodiments, the nucleic acid(s) encoding a pyruvate decarboxylase isozyme 1 may be nucleic acid(s) originating from a yeast, and especially from *Saccharomyces cerevisiae.*

According to a particular embodiment, the nucleic acid(s) encoding a pyruvate decarboxylase isozyme 1 may be nucleic acid of SEQ ID NO: 17. The nucleic acid of SEQ ID NO: 17 encodes a pyruvate decarboxylase isozyme 1 originating from *Saccharomyces cerevisiae*, that may also be termed PDC1.

For the amino acid sequence of the pyruvate decarboxylase isozyme 1 from *Saccharomyces cerevisiae*, the one skilled in the art may refer to the accession number NP013145.1 in the UniProt database, or to SEQ ID NO. 18 described herein.

As above-mentioned, the expression level of the pyruvate decarboxylase isozyme 1 in the present invention is regulated by at least one promoter and at least one terminator, such as herein after defined more in details, which are present in 5' and 3' position respectively of the nucleic acid sequence encoding the said pyruvate decarboxylase isozyme 1.

As it is specified elsewhere in the present description, in some embodiments of the invention, the pyruvate decarboxylase isozyme 1 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Decarboxylase Isozyme 3

In preferred embodiments of a recombinant yeast according to the invention, the recombinant yeast is furthermore defined as having a genome in which:

(i) at least one, preferably all, nucleic acid encoding a pyruvate decarboxylase isozyme 3 PDC6 has been deleted, and/or (ii) at least one, preferably all, nucleic acid encoding a pyruvate decarboxylase isozyme 3 PDC6 is under the control of an inducible or repressible promoter and/or is in a destabilized form.

Without wishing to be bound by any particular theory, the inventors believe that an under expression of a pyruvate decarboxylase isozyme 3 gene shall reduce the flux from pyruvate to ethanol by reducing the consumption of the produced pyruvate into acetaldehyde.

In some embodiments, under expression of pyruvate decarboxylase isozyme 3 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate decarboxylase isozyme 3 under expression also encompasses the insertion of a nucleic acid encoding a destabilized pyruvate decarboxylase isozyme 3. A destabilized pyruvate decarboxylase isozyme 3 is a variant of pyruvate decarboxylase isozyme 3 that is more rapidly degraded within the yeast cell than the parent pyruvate decarboxylase isozyme 3.

In preferred embodiments, a destabilized pyruvate decarboxylase isozyme 3 consists of a degron-tagged pyruvate decarboxylase isozyme 3 protein.

For example, the pyruvate decarboxylase isozyme 3 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of pyruvate decarboxylase isozyme 3 belongs to the general knowledge of the one skilled in the art.

In this regard, the one skilled in the art may advantageously refer to the method described by Wang et al. (Biochemistry, 2001, 40: 1755-1763).

Preferred pyruvate decarboxylase isozyme 3 in the present specification is an enzyme having an EC number of no 4.1.1.1.

According to a preferred embodiment, the nucleic acid(s) encoding a pyruvate decarboxylase isozyme 3 may be nucleic acid(s) originating from organisms preferably selected in a group comprising prokaryotic organisms and eukaryotic organisms. In some preferred embodiments, the nucleic acid(s) encoding a pyruvate decarboxylase isozyme 3 may be nucleic acid(s) originating from a yeast, and especially from *Saccharomyces cerevisiae.*

According to a particular embodiment, the nucleic acid(s) encoding a pyruvate decarboxylase isozyme 3 may be nucleic acid of SEQ ID NO: 19. The nucleic acid of SEQ ID NO: 19 encodes a pyruvate decarboxylase isozyme 3 originating from *Saccharomyces cerevisiae*, that may also be termed PDC6.

For the amino acid sequence of the pyruvate decarboxylase isozyme 3 from *Saccharomyces cerevisiae*, the one skilled in the art may refer to the accession number NP011601.3 in the UniProt database, or to SEQ ID NO. 20 described herein.

As above-mentioned, the expression level of the pyruvate decarboxylase isozyme 3 in the present invention is regulated by at least one promoter and at least one terminator, such as herein after defined more in details, which are present in 5' and 3' position respectively of the nucleic acid sequence encoding the said pyruvate decarboxylase isozyme 3.

As it is specified elsewhere in the present description, in some embodiments of the invention, the pyruvate decarboxylase isozyme 3 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Decarboxylase Isozyme 2

In preferred embodiments of a recombinant yeast according to the invention, the recombinant yeast is furthermore defined as having a genome in which:

(i) at least one, preferably all, nucleic acid encoding a pyruvate decarboxylase isozyme 2 PDC5 has been deleted, and/or (ii) at least one, preferably all, nucleic acid encoding a pyruvate decarboxylase isozyme 2 PDC5 is under the control of an inducible or repressible promoter and/or is in a destabilized form.

Without wishing to be bound by any particular theory, the inventors believe that an under expression of a pyruvate decarboxylase isozyme 2 gene shall reduce the flux from pyruvate to ethanol by reducing the consumption of the produced pyruvate into acetaldehyde.

In some embodiments, under expression of pyruvate decarboxylase isozyme 2 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate decarboxylase isozyme 2 under expression also encompasses the insertion of a nucleic acid encoding a destabilized pyruvate decarboxylase isozyme 2. A destabilized pyruvate decarboxylase isozyme 2 is a variant of pyruvate decarboxylase isozyme 2 that is more rapidly degraded within the yeast cell than the parent pyruvate decarboxylase isozyme 2.

In preferred embodiments, a destabilized pyruvate decarboxylase isozyme 2 consists of a degron-tagged pyruvate decarboxylase isozyme 2 protein.

For example, the pyruvate decarboxylase isozyme 2 gene can be interrupted by loxP, or for example by URA3.Kl-loxP, and is thus deleted (which can also be termed inactivated). It can alternatively be interrupted by a cassette comprising genes of interest, as illustrated in the examples as filed.

A method implemented to measure the activity level of pyruvate decarboxylase isozyme 2 belongs to the general knowledge of the one skilled in the art.

In this regard, the one skilled in the art may advantageously refer to the method described by Wang et al. (Biochemistry, 2001, 40: 1755-1763).

Preferred pyruvate decarboxylase isozyme 2 in the present specification is an enzyme having an EC number of no 4.1.1.1.

According to a preferred embodiment, the nucleic acid(s) encoding a pyruvate decarboxylase isozyme 2 may be nucleic acid(s) originating from organisms preferably selected in a group comprising prokaryotic organisms and eukaryotic organisms. In some preferred embodiments, the nucleic acid(s) encoding a pyruvate decarboxylase isozyme 2 may be nucleic acid(s) originating from a yeast, and especially from *Saccharomyces cerevisiae.*

According to a particular embodiment, the nucleic acid(s) encoding a pyruvate decarboxylase isozyme 2 may be nucleic acid of SEQ ID NO: 21. The nucleic acid of SEQ ID NO: 21 encodes a pyruvate decarboxylase isozyme 2 originating from *Saccharomyces cerevisiae*, that may also be termed PDC5.

For the amino acid sequence of the pyruvate decarboxylase isozyme 2 from *Saccharomyces cerevisiae*, the one skilled in the art may refer to the accession number NP013235.1 in the UniProt database, or to SEQ ID NO. 22 described herein.

As above-mentioned, the expression level of the pyruvate decarboxylase isozyme 2 in the present invention is regulated by at least one promoter and at least one terminator, such as herein after defined more in details, which are present in 5' and 3' position respectively of the nucleic acid sequence encoding the said pyruvate decarboxylase isozyme 2.

As it is specified elsewhere in the present description, in some embodiments of the invention, the pyruvate decarboxylase isozyme 2 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 1

In preferred embodiments of a recombinant yeast according to the invention, the recombinant yeast is furthermore defined as having a genome in which:

(i) at least one, preferably all, nucleic acid encoding an alcohol dehydrogenase 1 ADH1 has been deleted, and/or (ii) at least one, preferably all, nucleic acid encoding an alcohol dehydrogenase 1 ADH1 is under the control of an inducible or repressible promoter and/or is in a destabilized form.

Without wishing to be bound by any particular theory, the inventors believe that an under expression of an alcohol dehydrogenase 1 gene shall increase Acetyl-CoA production by the recombinant yeast by reducing the consumption of the produced Acetaldehyde by its conversion into ethanol.

In some embodiments, under expression of alcohol dehydrogenase 1 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 1 under expression also encompasses the insertion of a nucleic acid encoding a destabilized alcohol dehydrogenase 1. A destabilized alcohol dehydrogenase 1 is a variant of alcohol dehydrogenase 1 that is more rapidly degraded within the yeast cell than the parent alcohol dehydrogenase 1.

In preferred embodiments, a destabilized alcohol dehydrogenase 1 consists of a degron-tagged alcohol dehydrogenase 1 protein.

For example, the alcohol dehydrogenase 1 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 1 belongs to the general knowledge of the one skilled in the art.

In this regard, the one skilled in the art may advantageously refer to the method described by Axel J. Ganzhorn et al., The Journal of Biological Chemistry (1987), Vol 262, no 8, p 3754-3761.

Preferred alcohol dehydrogenase 1 in the present specification is an enzyme having an EC number of no 1.1.1.1.

According to a preferred embodiment, the nucleic acid(s) encoding an alcohol dehydrogenase 1 may be nucleic acid(s) originating from organisms preferably selected in a group comprising prokaryotic organisms and eukaryotic organisms. In some preferred embodiments, the nucleic acid(s) encoding an alcohol dehydrogenase 1 may be nucleic acid(s) originating from a yeast, and especially from *Saccharomyces cerevisiae.*

According to a particular embodiment, the nucleic acid(s) encoding an alcohol dehydrogenase 1 may be nucleic acid of SEQ ID NO: 23. The nucleic acid of SEQ ID NO: 23 encodes an alcohol dehydrogenase 1 originating from *Saccharomyces cerevisiae*, that may also be termed ADH1.

For the amino acid sequence of the alcohol dehydrogenase 1 from *Saccharomyces cerevisiae*, the one skilled in the art may refer to the accession number NP014555.1 in the UniProt database, or to SEQ ID NO. 24 described herein.

As above-mentioned, the expression level of the alcohol dehydrogenase 1 in the present invention is regulated by at least one promoter and at least one terminator, such as herein after defined more in details, which are present in 5' and 3' position respectively of the nucleic acid sequence encoding the said alcohol dehydrogenase 1.

As it is specified elsewhere in the present description, in some embodiments of the invention, the alcohol dehydrogenase 1 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 3

In preferred embodiments of a recombinant yeast according to the invention, the recombinant yeast is furthermore defined as having a genome in which:

(i) at least one, preferably all, nucleic acid encoding an alcohol dehydrogenase 3 ADH3 has been deleted, and/or (ii) at least one, preferably all, nucleic acid encoding an alcohol dehydrogenase 3 ADH3 is under the control of an inducible or repressible promoter and/or is in a destabilized form.

Without wishing to be bound by any particular theory, the inventors believe that an under expression of an alcohol dehydrogenase 3 gene shall increase acetyl-CoA production by the recombinant yeast by reducing the consumption of the produced acetaldehyde by its conversion into ethanol.

In some embodiments, under expression of alcohol dehydrogenase 3 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 3 under expression also encompasses the insertion of a nucleic acid encoding a destabilized alcohol dehydrogenase 3. A destabilized alcohol dehydrogenase 3 is a variant of alcohol dehydrogenase 3 that is more rapidly degraded within the yeast cell than the parent alcohol dehydrogenase 3.

In preferred embodiments, a destabilized alcohol dehydrogenase 3 consists of a degron-tagged alcohol dehydrogenase 3 protein.

For example, the alcohol dehydrogenase 3 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 3 belongs to the general knowledge of the one skilled in the art.

In this regard, the one skilled in the art may advantageously refer to the method described by Axel J. Ganzhorn et al., The Journal of Biological Chemistry (1987), Vol 262, no 8, p 3754-3761.

Preferred alcohol dehydrogenase 3 in the present specification is an enzyme having an EC number of no 1.1.1.1.

According to a preferred embodiment, the nucleic acid(s) encoding an alcohol dehydrogenase 3 may be nucleic acid(s) originating from organisms preferably selected in a group comprising prokaryotic organisms and eukaryotic organisms. In some preferred embodiments, the nucleic acid(s) encoding an alcohol dehydrogenase 3 may be nucleic acid(s) originating from a yeast, and especially from *Saccharomyces cerevisiae.*

According to a particular embodiment, the nucleic acid(s) encoding an alcohol dehydrogenase 3 may be nucleic acid of SEQ ID NO: 25. The nucleic acid of SEQ ID NO: 25 encodes an alcohol dehydrogenase 3 originating from *Saccharomyces cerevisiae*, that may also be termed ADH3.

For the amino acid sequence of the alcohol dehydrogenase 3 from *Saccharomyces cerevisiae*, the one skilled in the art may refer to the accession number NP013800.1 in the UniProt database, or to SEQ ID NO. 26 described herein.

As above-mentioned, the expression level of the alcohol dehydrogenase 3 in the present invention is regulated by at least one promoter and at least one terminator, such as herein after defined more in details, which are present in 5' and 3' position respectively of the nucleic acid sequence encoding the said alcohol dehydrogenase 3.

As it is specified elsewhere in the present description, in some embodiments of the invention, the alcohol dehydrogenase 3 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 4

In preferred embodiments of a recombinant yeast according to the invention, the recombinant yeast is furthermore defined as having a genome in which:

(i) at least one, preferably all, nucleic acid encoding an alcohol dehydrogenase 4 ADH4 has been deleted, and/or (ii) at least one, preferably all, nucleic acid encoding an alcohol dehydrogenase 4 ADH4 is under the control of an inducible or repressible promoter and/or is in a destabilized form.

Without wishing to be bound by any particular theory, the inventors believe that an under expression of an alcohol dehydrogenase 4 gene shall increase Acetyl-CoA production by the recombinant yeast by reducing the consumption of the produced acetaldehyde by its conversion into ethanol.

In some embodiments, under expression of alcohol dehydrogenase 4 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 4 under expression also encompasses the insertion of a nucleic acid encoding a destabilized alcohol dehydrogenase 4. A destabilized alcohol dehydrogenase 4 is a variant of alcohol dehydrogenase 4 that is more rapidly degraded within the yeast cell than the parent alcohol dehydrogenase 4.

In preferred embodiments, a destabilized alcohol dehydrogenase 4 consists of a degron-tagged alcohol dehydrogenase 4 protein.

For example, the alcohol dehydrogenase 4 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 4 belongs to the general knowledge of the one skilled in the art.

In this regard, the one skilled in the art may advantageously refer to the method described by Axel J. Ganzhorn et al., The Journal of Biological Chemistry (1987), Vol 262, no 8, p 3754-3761.

Preferred alcohol dehydrogenase 4 in the present specification is an enzyme having an EC number of no 1.1.1.1.

According to a preferred embodiment, the nucleic acid(s) encoding an alcohol dehydrogenase 4 may be nucleic acid(s) originating from organisms preferably selected in a group comprising prokaryotic organisms and eukaryotic organisms. In some preferred embodiments, the nucleic acid(s) encoding an alcohol dehydrogenase 4 may be nucleic acid(s) originating from a yeast, and especially from *Saccharomyces cerevisiae.*

According to a particular embodiment, the nucleic acid(s) encoding an alcohol dehydrogenase 4 may be nucleic acid of SEQ ID NO: 27. The nucleic acid of SEQ ID NO: 27 encodes an alcohol dehydrogenase 4 originating from *Saccharomyces cerevisiae*, that may also be termed ADH4.

For the amino acid sequence of the alcohol dehydrogenase 4 from *Saccharomyces cerevisiae*, the one skilled in the art may refer to the accession number NP011258.2 in the UniProt database, or to SEQ ID NO. 28 described herein.

As above-mentioned, the expression level of the alcohol dehydrogenase 4 in the present invention is regulated by at least one promoter and at least one terminator, such as herein after defined more in details, which are present in 5' and 3' position respectively of the nucleic acid sequence encoding the said alcohol dehydrogenase 4.

As it is specified elsewhere in the present description, in some embodiments of the invention, the alcohol dehydrogenase 4 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 5

In preferred embodiments of a recombinant yeast according to the invention, the recombinant yeast is furthermore defined as having a genome in which:

(i) at least one, preferably all, nucleic acid encoding an alcohol dehydrogenase 5 ADH5 has been deleted, and/or (ii) at least one, preferably all, nucleic acid encoding an alcohol dehydrogenase 5 ADH5 is under the control of an inducible or repressible promoter and/or is in a destabilized form.

Without wishing to be bound by any particular theory, the inventors believe that an under expression of an alcohol dehydrogenase 5 gene shall increase Acetyl-CoA production by the recombinant yeast by reducing the consumption of the produced acetaldehyde by its conversion into ethanol.

In some embodiments, under expression of alcohol dehydrogenase 5 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 5 under expression also encompasses the insertion of a nucleic acid encoding a destabilized alcohol dehydrogenase 5. A destabilized alcohol dehydrogenase 5 is a variant of alcohol dehydrogenase 5 that is more rapidly degraded within the yeast cell than the parent alcohol dehydrogenase 5.

In preferred embodiments, a destabilized alcohol dehydrogenase 5 consists of a degron-tagged alcohol dehydrogenase 5 protein.

For example, the alcohol dehydrogenase 5 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 5 belongs to the general knowledge of the one skilled in the art.

In this regard, the one skilled in the art may advantageously refer to the method described by Axel J. Ganzhorn et al., The Journal of Biological Chemistry (1987), Vol 262, no 8, p 3754-3761.

Preferred alcohol dehydrogenase 5 in the present specification is an enzyme having an EC number of no 1.1.1.1.

According to a preferred embodiment, the nucleic acid(s) encoding an alcohol dehydrogenase 5 may be nucleic acid(s) originating from organisms preferably selected in a group comprising prokaryotic organisms and eukaryotic organisms. In some preferred embodiments, the nucleic acid(s) encoding an alcohol dehydrogenase 5 may be nucleic acid(s) originating from a yeast, and especially from *Saccharomyces cerevisiae.*

According to a particular embodiment, the nucleic acid(s) encoding an alcohol dehydrogenase 5 may be nucleic acid of SEQ ID NO: 29. The nucleic acid of SEQ ID NO: 29 encodes an alcohol dehydrogenase 5 originating from *Saccharomyces cerevisiae*, that may also be termed ADH5.

For the amino acid sequence of the alcohol dehydrogenase 5 from *Saccharomyces cerevisiae*, the one skilled in the art may refer to the accession number NP009703.3 in the UniProt database, or to SEQ ID NO. 30 described herein.

As above-mentioned, the expression level of the alcohol dehydrogenase 5 in the present invention is regulated by at least one promoter and at least one terminator, such as herein after defined more in details, which are present in 5' and 3' position respectively of the nucleic acid sequence encoding the said alcohol dehydrogenase 5.

As it is specified elsewhere in the present description, in some embodiments of the invention, the alcohol dehydrogenase 5 is (a) fully or partially deleted, and/or (b) under the control of an inducible or repressible promoter; under the control of a weak promoter; and/or in a destabilized form, in a recombinant yeast according to the invention.

Acetaldehyde-CoA Dehydrogenase-Encoding Gene Over Expression and/or Controlled Expression In preferred embodiments of a recombinant yeast according to the invention, over expression of an acetaldehyde-CoA dehydrogenase-encoding gene is obtained by inserting, at selected location(s) of the yeast genome, one or more copies of an expression cassette comprising an acetaldehyde-CoA dehydrogenase coding sequence. Acetaldehyde-CoA dehydrogenase and an acetaldehyde-CoA dehydrogenase-encoding gene that are encompassed by the invention are detailed elsewhere in the present specification.

In some of these embodiments, the said one or more copies of an expression cassette comprising an acetaldehyde-CoA dehydrogenase coding sequence comprise(s) regulatory sequences allowing a strong expression of the acetaldehyde-CoA dehydrogenase, such as a strong promoter that is functional in yeast cells.

In addition to or as an alternative to these embodiments of a recombinant yeast according to the invention, at least one acetaldehyde-CoA dehydrogenase-encoding gene can be under the control of an inducible or repressible promoter that is functional in yeast cells.

Without wishing to be bound by any particular theory, the inventors believe that over expression of an acetaldehyde-CoA dehydrogenase may enhance the conversion of the intermediate metabolite acetaldehyde into acetyl-CoA. The same applies when at least one acetaldehyde-CoA dehydrogenase coding sequence is under the control of an inducible or repressible promoter.

In some preferred embodiments, the said acetaldehyde-CoA dehydrogenase-encoding gene is the MHPF gene from *Escherichia coli* as shown in the examples herein and discussed previously.

In preferred embodiments, the said acetaldehyde-CoA dehydrogenase-encoding gene is placed under the control of the strong promoter pTDH3 or of the strong promoter pPDC1.

Illustratively, the acetaldehyde-CoA dehydrogenase gene may be inserted within the HIS3 gene, as it is shown in the examples herein.

Acetate Kinase-Encoding Gene Over Expression and/or Controlled Expression

In preferred embodiments of a recombinant yeast according to the invention, over expression of an acetate kinase-encoding gene is obtained by inserting, at selected location(s) of the yeast genome, one or more copies of an expression cassette comprising an acetate kinase coding sequence. Acetate kinase and an acetate kinase-encoding gene that are encompassed by the invention are detailed elsewhere in the present specification.

In some of these embodiments, the said one or more copies of an expression cassette comprising an acetate kinase coding sequence comprise(s) regulatory sequences allowing a strong expression of the acetate kinase, such as a strong promoter that is functional in yeast cells.

In addition to or as an alternative to these embodiments of a recombinant yeast according to the invention, at least one acetate kinase-encoding gene can be under the control of an inducible or repressible promoter that is functional in yeast cells.

Without wishing to be bound by any particular theory, the inventors believe that over expression of an acetate kinase may enhance the conversion of the intermediate metabolite acetaldehyde into acetyl-CoA by catalyzing acetate in acetyl-phosphate and ADP in the presence of ATP. The same applies when at least one acetate kinase coding sequence is under the control of an inducible or repressible promoter.

In some preferred embodiments, the said acetate kinase-encoding gene is the AckA gene from *Escherichia coli* as shown in the examples herein and discussed previously.

In preferred embodiments, the said acetate kinase-encoding gene is placed under the control of the pACU6 promoter.

Illustratively, the acetate kinase gene may be inserted within the SAM3 gene.

Phosphate Acetyl Transferase-Encoding Gene Over Expression and/or Controlled Expression In preferred embodiments of a recombinant yeast according to the invention, over expression of a phosphate acetyl transferase-encoding gene is obtained by inserting, at selected location(s) of the yeast genome, one or more copies of an expression cassette comprising a phosphate acetyl transferase coding sequence. Phosphate acetyl transferase and a phosphate acetyl transferase-encoding gene that are encompassed by the invention are detailed elsewhere in the present specification.

In some of these embodiments, the said one or more copies of an expression cassette comprising a phosphate acetyl transferase coding sequence comprise(s) regulatory sequences allowing a strong expression of the phosphate acetyl transferase, such as a strong promoter that is functional in yeast cells.

In addition to or as an alternative to these embodiments of a recombinant yeast according to the invention, at least one phosphate acetyl transferase-encoding gene can be under the control of an inducible or repressible promoter that is functional in yeast cells.

Without wishing to be bound by any particular theory, the inventors believe that over expression of an phosphate acetyl transferase may enhance the conversion of the intermediate metabolite acetaldehyde into acetyl-CoA by catalyzing acetyl-phosphate in acetyl-CoA and phosphate in the presence of CoA. The same applies when at least one phosphate acetyl transferase coding sequence is under the control of an inducible or repressible promoter.

In some preferred embodiments, the said phosphate acetyl transferase-encoding gene is the PTA gene from *Escherichia coli*, or *Lactobacillus sanfranciscensis* as shown in the examples herein and discussed previously.

In preferred embodiments, the said phosphate acetyl transferase-encoding gene is placed under the control of the pCUP1-1 promoter.

Illustratively, the phosphate acetyl transferase gene may be inserted within the SAM3 gene.

Transketolase 1 (TKL1)

The transketolase 1 is a protein which is described in the art for catalyzing the transfer of a two-carbon ketol group from a ketose donor to an aldose acceptor via a covalent intermediate with the cofactor thiamine pyrophosphate. The transketolase 1 encoded by the genome of *Saccharomyces cerevisiae* may be termed TKL1.

A method implemented to measure the activity level of transketolase 1 belongs to the general knowledge of the one skilled in the art.

In this regard, the one skilled in the art may advantageously refer to the method described by Matsushika et al. (2012) Enzyme and microbial technology 51 p 16-25.

Preferred transketolase 1 in the present specification is an enzyme having an EC number of no EC 2.2.1.1.

According to a preferred embodiment, the nucleic acid(s) encoding a transketolase 1 may be nucleic acid(s) originating from organisms preferably selected in a group comprising prokaryotic organisms and eukaryotic organisms. In some embodiments, the nucleic acid(s) encoding a transketolase 1 may be nucleic acid(s) originating from archaebacteria. In some embodiments, the nucleic acid(s) encoding a transketolase 1 may be nucleic acid(s) originating from organisms preferably selected from yeasts. In some other preferred embodiments, the nucleic acid(s) encoding a transketolase 1 may be nucleic acid(s) originating from *Saccharomyces cerevisiae.*

According to a yet preferred embodiment, the nucleic acid(s) encoding a transketolase 1 may be nucleic acid(s) selected from the group consisting of sequences having at least 45%, advantageously at least 65%, preferably at least 80%, nucleic acid identity with a nucleic acid of SEQ ID NO: 9, and also a biological activity of the same nature. The nucleic acid of SEQ ID NO: 9 encodes a transketolase 1 originating from *Saccharomyces cerevisiae*, that may also be termed TKL1.

A biological activity of the same nature regarding this sequence is the capacity to code for an enzyme that catalyzes the transfer of a two-carbon ketol group from a ketose donor to an aldose acceptor via a covalent intermediate with the cofactor thiamine pyrophosphate.

As described herein, a nucleic acid sequence having at least 45% nucleotide identity with a reference nucleic acid sequence encompasses nucleic acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the transketolase 1 from *Saccharomyces cerevisiae*, the one skilled in the art may refer to the accession number NP015399.1 in the UniProt database, or to SEQ ID NO. 10 described herein.

According to another particular embodiment, the nucleic acid(s) encoding transketolase 1 may be nucleic acid(s) encoding an amino acid sequence selected from the group consisting of sequences having at least 45%, advantageously at least 65%, preferably at least 80%, amino acid identity with the amino acid sequence of SEQ ID NO: 10, and also a biological activity of the same nature.

A biological activity of the same nature regarding this sequence is as described previously, i.e. the capacity to catalyze the transfer of a two-carbon ketol group from a ketose donor to an aldose acceptor via a covalent intermediate with the cofactor thiamine pyrophosphate.

As described herein, an amino acid sequence having at least 45% amino acid identity with a reference nucleic acid sequence encompasses amino acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the transketolase 1 in the present invention is regulated by at least one promoter and at least one terminator, such as herein after defined more in details, which are present in 5' and 3' position respectively of the nucleic acid sequence encoding the said transketolase 1.

As it is specified elsewhere in the present description, the strong transketolase 1 expression shall be controlled in a recombinant yeast according to the invention.

In preferred embodiments, the controlled strong expression of the transketolase 1 is performed by placing the transketolase 1-encoding nucleic acid sequence under the control of an appropriate inducible or repressible promoter, preferably a strong inducible or repressible promoter.

Transaldolase 1 (TAL1)

The transaldolase 1 is a protein which is described in the art for catalyzing the conversion of sedoheptulose 7-phosphate and D-glyceraldehyde 3-phosphate into D-erythrose 4-phosphate and D-fructose 6-phosphate. The transaldolase 1 encoded by the genome of *Saccharomyces cerevisiae* may be termed TAL1.

A method implemented to measure the activity level of transaldolase 1 belongs to the general knowledge of the one skilled in the art.

In this regard, the one skilled in the art may advantageously refer to the method described by Matsushika et al. (2012) Enzyme and microbial technology 51 p 16-25.

Preferred transaldolase 1 in the present specification is an enzyme having an EC number of no EC 2.2.1.2.

According to a preferred embodiment, the nucleic acid(s) encoding a transaldolase 1 may be nucleic acid(s) originating from organisms preferably selected in a group comprising prokaryotic organisms and eukaryotic organisms. In some embodiments, the nucleic acid(s) encoding a transaldolase 1 may be nucleic acid(s) originating from archaebacteria. In some embodiments, the nucleic acid(s) encoding a transaldolase 1 may be nucleic acid(s) originating from organisms preferably selected from yeasts. In some other preferred embodiments, the nucleic acid(s) encoding a transaldolase 1 may be nucleic acid(s) originating from *Saccharomyces cerevisiae*.

According to a yet preferred embodiment, the nucleic acid(s) encoding a transaldolase 1 may be nucleic acid(s) selected from the group consisting of sequences having at least 45%, advantageously at least 65%, preferably at least 80%, nucleic acid identity with a nucleic acid of SEQ ID NO: 11, and also a biological activity of the same nature. The nucleic acid of SEQ ID NO: 11 encodes a transaldolase 1 originating from *Saccharomyces cerevisiae*, that may also be termed TAL1.

A biological activity of the same nature regarding this sequence is the capacity to code for an enzyme that catalyzes the conversion of sedoheptulose 7-phosphate and D-glyceraldehyde 3-phosphate into D-erythrose 4-phosphate and D-fructose 6-phosphate.

As described herein, a nucleic acid sequence having at least 45% nucleotide identity with a reference nucleic acid sequence encompasses nucleic acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the transaldolase 1 from *Saccharomyces cerevisiae*, the one skilled in the art may refer to the accession number NP013458.1 in the UniProt database, or to SEQ ID NO. 12 described herein.

According to another particular embodiment, the nucleic acid(s) encoding transketolase 1 may be nucleic acid(s) encoding an amino acid sequence selected from the group consisting of sequences having at least 45%, advantageously at least 65%, preferably at least 80%, amino acid identity with the amino acid sequence of SEQ ID NO: 12, and also a biological activity of the same nature.

A biological activity of the same nature regarding this sequence is as described previously, i.e. the capacity to catalyze the conversion of sedoheptulose 7-phosphate and D-glyceraldehyde 3-phosphate into D-erythrose 4-phosphate and D-fructose 6-phosphate.

As described herein, an amino acid sequence having at least 45% amino acid identity with a reference nucleic acid sequence encompasses amino acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the transaldolase 1 in the present invention is regulated by at least one promoter and at least one terminator, such as herein after defined more in details, which are present in 5' and 3' position respectively of the nucleic acid sequence encoding the said transaldolase 1.

As it is specified elsewhere in the present description, the strong transaldolase 1 expression shall be controlled in a recombinant yeast according to the invention.

In preferred embodiments, the controlled strong expression of the transaldolase 1 is performed by placing the transaldolase 1-encoding nucleic acid sequence under the control of an appropriate inducible or repressible promoter, preferably a strong inducible or repressible promoter.

Acetaldehyde-CoA Dehydrogenase (MHPF)

The acetaldehyde-CoA dehydrogenase is a protein which is described in the art for catalyzing the conversion of acetaldehyde into acetyl-CoA while freeing one NADH. The acetaldehyde-CoA dehydrogenase encoded by the genome of *E. coli* may be termed MHPF.

A method implemented to measure the activity level of acetaldehyde-CoA dehydrogenase belongs to the general knowledge of the one skilled in the art.

In this regard, the one skilled in the art may advantageously refer to the method described by Fischer et al. (2013) Chemi. Biol. Interact. 202 70-77.

Preferred acetaldehyde-CoA dehydrogenase in the present specification is an enzyme having an EC number of no EC 1.2.1.10.

According to a preferred embodiment, the nucleic acid(s) encoding an acetaldehyde-CoA dehydrogenase may be nucleic acid(s) originating from organisms preferably selected in a group comprising prokaryotic organisms and eukaryotic organisms. In some embodiments, the nucleic acid(s) encoding an acetaldehyde-CoA dehydrogenase may be nucleic acid(s) originating from archaebacteria. In some embodiments, the nucleic acid(s) encoding an acetaldehyde-CoA dehydrogenase may be nucleic acid(s) originating from organisms preferably selected from bacteria. In some other preferred embodiments, the nucleic acid(s) encoding an acetaldehyde-CoA dehydrogenase may be nucleic acid(s) originating from *Escherichia coli.*

According to a yet preferred embodiment, the nucleic acid(s) encoding an acetaldehyde-CoA dehydrogenase may be nucleic acid(s) selected from the group consisting of sequences having at least 30%, advantageously at least 65%, preferably at least 80%, nucleic acid identity with a nucleic acid of SEQ ID NO: 31, and also a biological activity of the same nature. The nucleic acid of SEQ ID NO: 31 encodes an acetaldehyde-CoA dehydrogenase originating from *Escherichia coli*, that may also be termed MHPF.

A biological activity of the same nature regarding this sequence is the capacity to code for an enzyme that catalyzes the conversion of acetaldehyde into acetyl-CoA while freeing one NADH.

As described herein, a nucleic acid sequence having at least 30% nucleotide identity with a reference nucleic acid sequence encompasses nucleic acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the acetaldehyde-CoA dehydrogenase from *Escherichia coli*, the one skilled in the art may refer to the accession number NP414885 in the UniProt database, or to SEQ ID NO. 32 described herein.

According to another particular embodiment, the nucleic acid(s) encoding acetaldehyde-CoA dehydrogenase may be nucleic acid(s) encoding an amino acid sequence selected from the group consisting of sequences having at least 30%, advantageously at least 65%, preferably at least 80%, amino acid identity with the amino acid sequence of SEQ ID NO: 32, and also a biological activity of the same nature. Illustratively, the acetaldehyde-CoA dehydrogenase originating from *Streptomyces niveiscabiei* has 32% amino acid identity with the acetaldehyde-CoA dehydrogenase of SEQ ID NO. 32.

A biological activity of the same nature regarding this sequence is as described previously, i.e. the capacity to catalyze the conversion of acetaldehyde into acetyl-CoA while freeing one NADH.

As described herein, an amino acid sequence having at least 30% amino acid identity with a reference nucleic acid sequence encompasses amino acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the acetaldehyde-CoA dehydrogenase in the present invention is regulated by at least one promoter and at least one terminator, such as herein after defined more in details, which are present in 5' and 3' position respectively of the nucleic acid sequence encoding the said acetaldehyde-CoA dehydrogenase.

As it is specified elsewhere in the present description, the strong acetaldehyde-CoA dehydrogenase expression shall be controlled in a recombinant yeast according to the invention.

In preferred embodiments, the controlled strong expression of the acetaldehyde-CoA dehydrogenase is performed by placing the acetaldehyde-CoA dehydrogenase-encoding nucleic acid sequence under the control of an appropriate inducible or repressible promoter, preferably a strong inducible or repressible promoter.

Acetate Kinase (AckA)

The acetate kinase is a protein which is described in the art for catalyzing acetate in acetyl-phosphate and ADP in the presence of ATP. The acetate kinase encoded by the genome of *E. coli* may be termed AckA.

A method implemented to measure the activity level of acetate kinase belongs to the general knowledge of the one skilled in the art.

In this regard, the one skilled in the art may advantageously refer to the method described by Sagers et al. J. Bacteriology (1961) 82, 233-238.

Preferred acetate kinase in the present specification is an enzyme having an EC number of no EC 2.7.2.1.

According to a preferred embodiment, the nucleic acid(s) encoding an acetate kinase may be nucleic acid(s) originating from organisms preferably selected in a group comprising prokaryotic organisms and eukaryotic organisms. In some embodiments, the nucleic acid(s) encoding an acetate kinase may be nucleic acid(s) originating from archaebacteria. In some embodiments, the nucleic acid(s) encoding an acetate kinase may be nucleic acid(s) originating from organisms preferably selected from bacteria. In some other preferred embodiments, the nucleic acid(s) encoding an acetate kinase may be nucleic acid(s) originating from *Escherichia coli.*

According to a yet preferred embodiment, the nucleic acid(s) encoding an acetate kinase may be nucleic acid(s) selected from the group consisting of sequences having at least 29%, advantageously at least 65%, preferably at least 80%, nucleic acid identity with a nucleic acid of SEQ ID NO: 33, and also a biological activity of the same nature. The nucleic acid of SEQ ID NO: 33 encodes an acetate kinase originating from *Escherichia coli*, that may also be termed AckA.

A biological activity of the same nature regarding this sequence is the capacity to code for an enzyme that catalyzes the conversion of acetate in acetyl-phosphate and ADP in the presence of ATP.

As described herein, a nucleic acid sequence having at least 29% nucleotide identity with a reference nucleic acid sequence encompasses nucleic acid sequences having at least 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the acetate kinase from *Escherichia coli*, the one skilled in the art may refer to the accession number NP416799 in the UniProt database, or to SEQ ID NO. 34 described herein.

According to another particular embodiment, the nucleic acid(s) encoding acetate kinase may be nucleic acid(s) encoding an amino acid sequence selected from the group consisting of sequences having at least 29%, advantageously at least 65%, preferably at least 80%, amino acid identity with the amino acid sequence of SEQ ID NO: 34, and also a biological activity of the same nature. Illustratively, the acetate kinase originating from *Ureaplasma urealyticum* has 29% amino acid identity with the acetate kinase of SEQ ID NO. 34.

A biological activity of the same nature regarding this sequence is as described previously, i.e. the capacity to catalyze the conversion of acetate in acetyl-phosphate and ADP in the presence of ATP.

As described herein, an amino acid sequence having at least 29% amino acid identity with a reference nucleic acid sequence encompasses amino acid sequences having at least 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the acetate kinase in the present invention is regulated by at least one promoter and at least one terminator, such as herein after defined more in details, which are present in 5' and 3' position respectively of the nucleic acid sequence encoding the said acetate kinase.

As it is specified elsewhere in the present description, the strong acetate kinase expression shall be controlled in a recombinant yeast according to the invention.

In preferred embodiments, the controlled strong expression of the acetate kinase is performed by placing the acetate kinase-encoding nucleic acid sequence under the control of an appropriate inducible or repressible promoter, preferably a strong inducible or repressible promoter.

Phosphate Acetyl Transferase (PTA)

The phosphate acetyl transferase is a protein which is described in the art for catalyzing acetyl-phosphate in acetyl-CoA and phosphate in the presence of CoA. The phosphate acetyl transferase encoded by the genome of *E. coli* may be termed PTA.

A method implemented to measure the activity level of phosphate acetyl transferase belongs to the general knowledge of the one skilled in the art.

In this regard, the one skilled in the art may advantageously refer to the method described by Castano-Cerezo, ans Canvas, Microbial Cell Factories 2009, 8:54.

Preferred phosphate acetyl transferase in the present specification is an enzyme having an EC number of no EC 2.3.1.8.

According to a preferred embodiment, the nucleic acid(s) encoding a phosphate acetyl transferase may be nucleic acid(s) originating from organisms preferably selected in a group comprising prokaryotic organisms and eukaryotic organisms. In some embodiments, the nucleic acid(s) encoding a phosphate acetyl transferase may be nucleic acid(s) originating from archaebacteria. In some embodiments, the nucleic acid(s) encoding a phosphate acetyl transferase may be nucleic acid(s) originating from organisms preferably selected from bacteria. In some other preferred embodiments, the nucleic acid(s) encoding a phosphate acetyl transferase may be nucleic acid(s) originating from *Escherichia coli.*

According to a yet preferred embodiment, the nucleic acid(s) encoding a phosphate acetyl transferase may be nucleic acid(s) selected from the group consisting of sequences having at least 35%, advantageously at least 65%, preferably at least 80%, nucleic acid identity with a nucleic acid of SEQ ID NO: 35, and also a biological activity of the same nature. The nucleic acid of SEQ ID NO: 35 encodes a phosphate acetyl transferase originating from *Escherichia coli*, that may also be termed PTA.

A biological activity of the same nature regarding this sequence is the capacity to code for an enzyme that catalyzes the conversion of acetyl-phosphate in acetyl-CoA and phosphate in the presence of CoA.

As described herein, a nucleic acid sequence having at least 35% nucleotide identity with a reference nucleic acid sequence encompasses nucleic acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the phosphate acetyl transferase from *Escherichia coli*, the one skilled in the art may refer to the accession number NP416800 in the UniProt database, or to SEQ ID NO. 36 described herein.

According to another particular embodiment, the nucleic acid(s) encoding phosphate acetyl transferase may be nucleic acid(s) encoding an amino acid sequence selected from the group consisting of sequences having at least 35%, advantageously at least 65%, preferably at least 80%, amino acid identity with the amino acid sequence of SEQ ID NO: 36, and also a biological activity of the same nature. Illustratively, the phosphate acetyl transferase originating from *Entomoplasma luminosum* has 36% amino acid identity with the phosphate acetyl transferase of SEQ ID NO. 36.

A biological activity of the same nature regarding this sequence is as described previously, i.e. the capacity to catalyze the conversion of acetyl-phosphate in acetyl-CoA and phosphate in the presence of CoA.

As described herein, an amino acid sequence having at least 35% amino acid identity with a reference nucleic acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the phosphate acetyl transferase in the present invention is regulated by at least one promoter and at least one terminator, such as herein after defined more in details, which are present in 5' and 3' position respectively of the nucleic acid sequence encoding the said phosphate acetyl transferase.

As it is specified elsewhere in the present description, the strong phosphate acetyl transferase expression shall be controlled in a recombinant yeast according to the invention.

In preferred embodiments, the controlled strong expression of the phosphate acetyl transferase is performed by placing the phosphate acetyl transferase-encoding nucleic acid sequence under the control of an appropriate inducible or repressible promoter, preferably a strong inducible or repressible promoter.

Export of the Compounds of Interest

In further embodiments of a recombinant yeast according to the invention, the export of the produced oxaloacetate derivatives outside of the yeast cell may be enhanced by (i) under expression of genes encoding yeast permeases, by (ii) over expression of genes encoding amino acid exporter proteins, or by (iii) both under expression of genes encoding yeast permeases and over expression of genes encoding amino acid exporter proteins.

Under Expression of Permease-Encoding Gene(s)

As it is described below, permease-encoding genes that may be under expressed in a recombinant yeast according to the invention encompass AGP1, AGP3, BAP3, BAP2, GAP1, GNP1, MUP3 and MUP1.

AGP1 is the general amino acid permease 1 from *Saccharomyces cerevisiae*. For the amino acid sequence of AGP1 it may be referred to the access number NP_009905 in the UniProt database. For the nucleic acid sequence, it may be referred to the access number NM_001178671 in the NCBI database.

AGP3 is the general amino acid permease 3 from *Saccharomyces cerevisiae*. For the amino acid sequence of AGP3 it may be referred to the access number NP_116600 in the UniProt database. For the nucleic acid sequence, it may be referred to the access number NM_001179912 in the NCBI database.

BAP3 is the valine amino acid permease from *Saccharomyces cerevisiae*. For the amino acid sequence of BAP3 it may be referred to the access number NP_010331 in the UniProt database. For the nucleic acid sequence, it may be referred to the access number NM_001180354 in the NCBI database.

BAP2 is the Leu/Val/Ile amino acid permease from *Saccharomyces cerevisiae*. For the amino acid sequence of BAP2 it may be referred to the access number NP_009624 in the UniProt database. For the nucleic acid sequence, it may be referred to the access number NM_001178416 in the NCBI database.

GAP1 is the general amino-acid permease from *Saccharomyces cerevisiae*. For the amino acid sequence of GAP1 it may be referred to the access number NP_012965.3 in the UniProt database. For the nucleic acid sequence, it may be referred to the access number NM_001179829 in the NCBI database.

GNP1 is the high-affinity glutamine permease from *Saccharomyces cerevisiae*. For the amino acid sequence of GNP1 it may be referred to the access number NP_010796 in the UniProt database. For the nucleic acid sequence, it may be referred to the access number NM_001180816 in the NCBI database.

MUP3 is the low-affinity methionine permease from *Saccharomyces cerevisiae*. For the amino acid sequence of MUP3 it may be referred to the access number NP_011827 in the UniProt database. For the nucleic acid sequence, it may be referred to the access number NM_001179116 in the NCBI database.

MUP1 is the low-affinity methionine permease from *Saccharomyces cerevisiae*. For the amino acid sequence of MUP it may be referred to the access number NP_011569 in the UniProt database. For the nucleic acid sequence, it may be referred to the access number NM_001181184 in the NCBI database.

In some embodiments of a recombinant yeast according to the invention, the said recombinant yeast is further defined as having an under expression one or more genes encoding a permease, that encompasses AGP1, AGP3, BAP3, BAP2, GAP1, GNP1, MUP3 and MUP1 permeases.

Without wishing to be bound by any particular theory, the inventors believe that an under expression of any of the permease genes shall increase the excretion of the produced oxaloacetate derivatives outside the yeast cell, e.g. in the culture medium.

As regards permeases under expression of one or more of these genes encompasses a complete repression of their expression, e.g. by interruption or deletion of the said one or more permease genes.

In some embodiments, under expression of a permease-encoding gene may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards a permease gene, under expression also encompasses the insertion of a nucleic acid encoding a destabilized permease protein or the insertion of a nucleic acid encoding a destabilized permease protein, or both.

A destabilized permease is a variant of a permease that is more rapidly degraded within the yeast cell than the parent permease.

In preferred embodiments, a destabilized permease consists of a degron-tagged permease protein.

As illustrated in the examples, the AGP3 gene, the BAP3 gene, the GAP1 gene, the GNP1 gene and the MUP3 gene can be interrupted by loxP and are thus deleted.

Over Expression of Amino Acid Exporter Protein-Encoding Gene(s)

As it is described below, exporter protein-encoding genes that may be over expressed in a recombinant yeast according to the invention encompass AQR1 and TPO1.

AQR1 is a transporter from *Saccharomyces cerevisiae*. For the amino acid sequence of AQR1 it may be referred to the access number NP_014334 in the UniProt database. For the nucleic acid sequence, it may be referred to the access number NM_001182903 in the NCBI database.

TPO1 is a polyamine transporter from *Saccharomyces cerevisiae*. For the amino acid sequence of TPO1 it may be referred to the access number NP_013072 in the UniProt database. For the nucleic acid sequence, it may be referred to the access number NM_001181848 in the NCBI database.

In preferred embodiments of a recombinant yeast according to the invention, over expression of a transporter-encoding gene is obtained by inserting, at selected location(s) of the yeast genome, one or more additional copies of an expression cassette comprising the said transporter coding sequence.

Without wishing to be bound by any particular theory, the inventors believe that an over expression of a transporter-encoding gene shall increase the excretion of the produced oxaloacetate derivatives outside the yeast cell, e.g. in the culture medium.

In some embodiments, over expression of a transporter-encoding gene is obtained by inserting, at selected location(s) of the yeast genome, one or more additional copies of an expression cassette comprising a transporter gene coding sequence. In some of these embodiments, the said one or more copies of an expression cassette comprising a transporter coding sequence comprise regulatory sequences allowing a strong expression of the said transporter, such as a strong promoter that is functional in yeast cells.

In some other embodiments, one copy of a transporter-encoding gene is inserted at a selected location of the yeast genome. In these other embodiments, the said one or more copies of an expression cassette comprising a transporter coding sequence comprise regulatory sequences allowing a strong expression of the said transporter, such as a strong promoter that is functional in yeast cells.

In preferred embodiments, the said amino acid exporter protein-encoding gene AQR1 is placed under the control of the strong promoter pTEF3.

Illustratively, the AQR1 gene may be inserted within the HOM3 gene.

In preferred embodiments, the said amino acid exporter protein-encoding gene_TPO1 is placed under the control of the strong inducible or repressible promoter pSAM4 or the strong constitutive promoter pTEF1.

TPO1-1 can be used instead of TPO1. TPO1-1 is an artificial allele in which the lysines 10, 49, 86, 143, 144 and 145 are replaced by arginines.

It is believed by the inventors that these modifications protect TPO1 from degradation through the ubiquitin-proteasome pathway, thus stabilizing it.

Illustratively, the TPO1 gene may be inserted within the MAE1 gene and/or within the TRP1 gene.

Further Embodiments of an Oxaloacetate Derivatives-Producing Recombinant Yeast

According to some embodiments of a recombinant yeast according to the invention, production of oxaloacetate derivatives may be further increased by placing the said recombinant yeast in conditions leading to a further increase in the production of the intermediates downstream oxaloacetate in the biosynthesis pathway of said oxaloacetate derivatives.

Placing the said recombinant yeast in conditions leading to an increased production of the intermediates downstream oxaloacetate in the biosynthesis pathway of said oxaloacetate derivatives may be performed by introducing further genetic modifications in the yeast genome.

The present inventors have found that an optimally increased oxaloacetate derivatives production may be reached by introducing further genetic changes to the oxaloacetate derivatives-producing recombinant yeast, that are described below.

First Further Embodiments of Oxaloacetate Derivatives-Producing Recombinant Yeast According to these first further embodiments of an oxaloacetate derivatives-producing recombinant yeast according to the invention, further genetic engineering of the recombinant yeast is performed with the aim of increasing the production of methionine and/or of methionine derivatives.

Methionine derivatives can for example be selected from the group consisting of 2-hydroxy-4-(methylthio) butanoic acid (HMB) and 2-keto-4-methylthiobutyric acid (KMB).

According to these embodiments, genetic changes are introduced so as to:

(A) over express and/or put under the control of a inducible or repressible promoter at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP;

(B) put under the control of a inducible or repressible promoter at least one nucleic acid encoding an aspartokinase HOM3; and (C) (i) over express and/or put under the control of a inducible or repressible promoter (a) at least one nucleic acid encoding an homoserine-O-acetyltransferase MET2 and/or at least one nucleic acid encoding an homoserine-O-acetyltransferase METX, and (b) at least one nucleic acid encoding a methionine synthase MET17; and/or (ii) over express and/or put under the control of a inducible or repressible promoter (a) at least one nucleic acid encoding an homoserine kinase THR1, and (b) at least one nucleic acid encoding a cystathionine gamma-synthase CGS1 that has an improved O-phospho-L-homoserine (OHPS) dependent methionine synthase activity.

According to these embodiments, at least one nucleic acid encoding an aspartate transaminase AAT2 can optionally be overexpressed and/or is under the control of an inducible or repressible promoter.

According to these embodiments, at least one nucleic acid encoding a glutamate dehydrogenase GDH that converts oxo-glutarate to glutamate can optionally be overexpressed and/or is under the control of an inducible or repressible promoter.

According to these embodiments, at least one nucleic acid encoding an homoserine dehydrogenase HOM6 can also optionally be overexpressed.

According to these embodiments, the genome of a recombinant yeast of the invention can optionally further be such that, independently: (i) at least one, preferably all, endogenous nucleic acid encoding a S-adenosyl methionine synthase SAM1 and/or SAM2 is deleted, or (ii) at least one, preferably all, nucleic acid encoding a S-adenosyl methionine synthase SAM1 and/or SAM2 is under the control of an inducible or repressible promoter and/or is in a destabilized form.

According to a first embodiment, the genome of a recombinant yeast of the invention can optionally further be such that, independently: (i) at least one, preferably all, endogenous nucleic acid encoding an Aromatic aminotransferase I ARO8 and/or a Cytosolic branched-chain amino acid (BCAA) aminotransferase gene BAT2 has been deleted, or (ii) at least one, preferably all, nucleic acid encoding an Aromatic aminotransferase I ARO8 and/or a Cytosolic branched-chain amino acid (BCAA) aminotransferase gene BAT2 is under the control of an inducible or repressible promoter and/or is in a destabilized form.

According to a second embodiment, the genome of a recombinant yeast of the invention can optionally further be such that, independently: (i) at least one, preferably all, nucleic acid encoding an Aromatic aminotransferase I ARO8, and/or (ii) at least one, preferably all, nucleic acid encoding a Cytosolic branched-chain amino acid (BCAA) aminotransferase gene BAT2, is overexpressed and/or is under the control of an inducible or repressible promoter.

According to this second embodiment, the genome of a recombinant yeast of the invention can optionally further be characterized by an under expression of the phenylpyruvate decarboxylase gene (ARO10).

Furthermore, according to this embodiment, the genome of a recombinant yeast of the invention can optionally further be characterized by a non-expression of the 2-hydroxyacide dehydrogenase gene (KDH) or as being such that at least one nucleic acid encoding 2-hydroxyacide dehydrogenase (KDH) is overexpressed and/or under the control of an inducible or repressible promoter.

According to these embodiments, at least one nucleic acid encoding a cystathionine gamma-lyase CYS3 can, independently, be under the control of a weak promoter or of an inducible or repressible promoter and/or be in a destabilized form.

According to these embodiments, at least one nucleic acid encoding a cystathionine beta-synthase CYS4 can, independently, be under the control of a weak promoter or of an inducible or repressible promoter and/or be in a destabilized form.

According to these embodiments, at least one nucleic acid encoding a homoserine kinase THR1 can optionally, independently, be under the control of an inducible or repressible promoter and/or be in a destabilized form.

Aspartate Semi-Aldehyde Dehydrogenase

The aspartate-semialdehyde dehydrogenase is a protein which is known in the art to catalyze the NADPH-dependent formation of L-aspartate-semialdehyde by the reductive dephosphorylation of L-aspartyl-4-phosphate. The aspartate-semialdehyde dehydrogenase encoded by the genome of *Saccharomyces cerevisiae* may be termed HOM2.

A method implemented to measure the activity level of aspartate semialdehyde dehydrogenase belongs to the general knowledge of the one skilled in the art.

Preferred aspartate semialdehyde dehydrogenase in the present specification is an enzyme having an EC number 1.2.1.11.

For the amino acid sequence of the aspartate-semialdehyde dehydrogenase from *Saccharomyces cerevisiae*, the one skilled in the art may refer to the accession number NP010442 in the UniProt database. For the nucleic acid sequence, it may be referred to the access number NM_001180465.3 in the UniProt database.

Aspartokinase

The aspartokinase enzyme is a protein which is described in the art for catalyzing the conversion of L-aspartate in the presence of ATP into 4-phospho-L-aspartate. The aspartokinase encoded by the genome of *Saccharomyces cerevisiae* may be termed HOM3.

A method implemented to measure the activity level of aspartokinase belongs to the general knowledge of the one skilled in the art.

In this regard, the one skilled in the art may advantageously refer to the method described by Stadtman et al. (1961, J Biol Chem, Vol. 236 (7): 2033-2038).

Preferred aspartokinase in the present specification is an enzyme having an EC number of no EC 2.7.2.4.

For the amino acid sequence of the aspartokinase from *Saccharomyces cerevisiae*, the one skilled in the art may refer to the accession number NP010972 in the UniProt database. For the nucleic acid sequence, it may be referred to the access number NM_001178943.1 in the UniProt database.

Homoserine-O-Acetyltransferase

The homoserine O-acetyl transferase enzyme is a protein which is described in the art for catalyzing the reaction between Acetyl-CoA and L-homoserine into CoA and O-acetyl-L-homoserine. The homoserine O-acetyl transferase encoded by the genome of *Saccharomyces cerevisiae* may be termed MET2. The homoserine O-acetyl transferase originating from *Corynebacterium glutamicum* is usually termed METX.

A method implemented to measure the activity level of homoserine O-acetyl transferase belongs to the general knowledge of the one skilled in the art.

In this regard, the one skilled in the art may advantageously refer to the method described by Shuzo Yamagata (1987, The Journal of Bacteriology, Vol. 169(8): 3458-3463.

Preferred homoserine O-acetyl transferase in the present specification is an enzyme having an EC number of no EC 2.3.1.31.

For the amino acid sequence of the homoserine O-acetyl transferase from *Saccharomyces cerevisiae*, the one skilled in the art may refer to the accession number NP014122 in the UniProt database. For the nucleic acid sequence, it may be referred to the access number NM_001183115.1 in the UniProt database.

Methionine Synthase

The methionine synthase is a protein which is described in the art for catalyzing the conversion of O-acetyl-L-homoserine (OAH) in the presence of methanthiol into methionine and acetate. The methionine synthase is also described in the art for catalyzing the conversion of OAH into homocysteine or the conversion of O-acetylserine (OAS) into cysteine. The methionine synthase encoded by the genome of *Saccharomyces cerevisiae* may be termed MET17. The methionine synthase encoded by the genome of *Saccharomyces cerevisiae* may also be termed MET25 or MET15 in the art.

A method implemented to measure the activity level of methionine synthase belongs to the general knowledge of the one skilled in the art.

In this regard, the one skilled in the art may advantageously refer to the method described by Ravanel (1995, Archives of Biochemistry and Biophysics, Vol. 316: 572-584).

Preferred methionine synthase in the present specification is an enzyme having an EC number of no 2.5.1.49.

For the amino acid sequence of the methionine synthase from *Saccharomyces cerevisiae*, the one skilled in the art may refer to the accession number NP013406 in the UniProt database. For the nucleic acid sequence, it may be referred to the access number NM_001182191.1 in the UniProt database.

Homoserine Kinase

Homoserine kinase enzyme is a protein which is described in the art for catalyzing the ATP-dependent phosphorylation of L-homoserine to L-homoserine phosphate.

Homoserine kinase encoded by the genome of *Saccharomyces cerevisiae* may be termed THR1.

A method implemented to measure the activity level of homoserine kinase belongs to the general knowledge of the one skilled in the art.

In this regard, the one skilled in the art may advantageously refer to the method described by Mannhaupt and Feldmann (1990, Eur J Biochem, Vol. 191: 115-122).

Preferred homoserine kinase in the present specification is an enzyme having an EC number of no EC 2.7.1.39.

For the amino acid sequence of the homoserine kinase from *Saccharomyces cerevisiae*, the one skilled in the art may refer to the accession number NP011890 in the UniProt database. For the nucleic acid sequence, it may be referred to the access number NM_001179155.1 in the UniProt database.

Cystathionine Gamma-Synthase

The cystathionine gamma synthase 1 enzyme is a protein which is described in the art for catalyzing the formation of L-cystathionine from homoserine esters and L-cysteine, via a gamma-replacement reaction. The cystathionine gamma synthase 1 encoded by the genome of *Arabidopsis thaliana* may be termed CGS1.

A method implemented to measure the activity level of cystathionine gamma synthase belongs to the general knowledge of the one skilled in the art.

In this regard, the one skilled in the art may advantageously refer to the method described by Loizeau et al. (2007, Plant Physiology, Vol. 145: 491-503).

Preferred cystathionine gamma synthase 1 in the present specification is an enzyme having an EC number of no EC 2.5.1.48.

For the amino acid sequence of the cystathionine gamma synthase 1 from *Arabidopsis thaliana*, the one skilled in the art may refer to the accession number NP186761 in the UniProt database. For the nucleic acid sequence, it may be referred to the access number NM_110977.3 in the UniProt database.

Aspartate Transaminase

The aspartate transaminase enzyme (also known as aspartate aminotransferase) is a protein which is described in the art for catalyzing the reaction of L-aspartate and 2-oxoglutarate for producing oxaloacetate and L-glutamate. The aspartate transaminase enzyme encoded by the genome *Saccharomyces cerevisiae* may be termed AAT2.

A method implemented to measure the activity level of an aspartate transaminase belongs to the general knowledge of the one skilled in the art.

In this regard, the one skilled in the art may advantageously refer to the method described in Yagi et al. (1982, Biochem, VOl. 92: 35-43).

For the amino acid sequence of the aspartate transaminase AAT2 from *Saccharomyces cerevisiae*, the one skilled in the art may refer to the accession number NP013127 in the UniProt database. For the nucleic acid sequence, it may be referred to the access number NM_001181914.1 in the UniProt database.

Glutamate Dehydrogenase

The glutamate dehydrogenase enzyme (also known as NAD-specific glutamate dehydrogenase) is a protein which is described in the art for catalyzing the transformation of 2-oxoglutarate for producing L-glutamate. Thus, glutamate dehydrogenase is an enzyme specifically involved in the chemical reaction involving the conversion of 2-oxoglutarate to L-glutamate, in the presence of NADH.

A method implemented to measure the activity level of glutamate dehydrogenase belongs to the general knowledge of the one skilled in the art.

In this regard, the one skilled in the art may advantageously refer to the method described in Noor and Punekar (2005, Microbiology, Vol. 151: 1409-1419).

In preferred embodiments, the said glutamate dehydrogenase-encoding gene encodes for a glutamate dehydrogenase which uses NADH instead of NADPH, and is more particularly the GDH gene from *Entodinium caudatum* (GDH.eCa).

Preferred glutamate dehydrogenase in the present specification can in particular be the enzyme having the EC number no EC 1.4.1.2.

For the amino acid sequence of the glutamate dehydrogenase from *Entodinium caudatum*, the one skilled in the art may refer to the accession number AAF15393 in the UniProt database. For the nucleic acid sequence, it may be referred to the access number AF109176 in the UniProt database.

Homoserine Dehydrogenase

The homoserine dehydrogenase enzyme is a protein which is described in the art for catalyzing the conversion of L-homoserine into L-aspartate 4-semialdehyde, in the presence of NAD or NADP. The homoserine dehydrogenase encoded by the genome of *Saccharomyces cerevisiae* may be termed HOM6.

A method implemented to measure the activity level of homoserine dehydrogenase belongs to the general knowledge of the one skilled in the art.

In this regard, the one skilled in the art may advantageously refer to the method described by Calnyanto et al. (2006, Microbiology, Vol. 152: 105-112).

Preferred homoserine dehydrogenase in the present specification is an enzyme having an EC number of no 1.1.1.3.

For the amino acid sequence of the homoserine dehydrogenase from *Saccharomyces cerevisiae*, the one skilled in the art may refer to the accession number NP012673 in the UniProt database. For the nucleic acid sequence, it may be referred to the access number NM_001181797.3 in the UniProt database.

S-Adenosyl Methionine Synthase

SAM1 is the S-adenosylmethionine synthase 1 from *Saccharomyces cerevisiae*. For the amino acid sequence of SAM1, it may be referred to the access number NP_010790 in the UniProt database. For the nucleic acid sequence, it may be referred to the access number NM_001180810 in the NCBI database.

SAM2 is the S-adenosylmethionine synthase 2 from *Saccharomyces cerevisiae*. For the amino acid sequence of SAM1, it may be referred to the access number NP_013281 in the UniProt database. For the nucleic acid sequence, it may be referred to the access number NM_00118082067 in the NCBI database.

Aromatic Aminotransferase I

ARO8 is the aromatic aminotransferase I from *Saccharomyces cerevisiae*. For the nucleic acid sequence, it may be referred to the access number NM_001181067.1 in the NCBI database. For the amino acid sequence of ARO8, it may be referred to the access number NP_011313.1 in the UniProt database.

A method implemented to measure the activity level of an aromatic aminotransferase I belongs to the general knowledge of the one skilled in the art.

Cytosolic Branched-Chain Amino Acid (BCAA) Aminotransferase Gene

BAT2 is the cytosolic branched-chain amino acid (BCAA) amino transferase from *Saccharomyces cerevisiae*. For the nucleic acid sequence, it may be referred to the access number NM_001181806.1 in the NCBI database. For the amino acid sequence of BAT2, it may be referred to the access number NP_012682.1 in the UniProt database.

A method implemented to measure the activity level of a cytosolic branched-chain amino acid (BCAA) amino transferase belongs to the general knowledge of the one skilled in the art.

Phenylpyruvate Decarboxylase

ARO10 is the phenylpyruvate decarboxylase from *Saccharomyces cerevisiae*. For the nucleic acid sequence, it may be referred to the access number NM_001180688.3 in the NCBI database.

For the amino acid sequence of ARO10, it may be referred to the access number NP_010668.3 in the UniProt database.

2-Hydroxyacide Dehydrogenase

KDH is the 2-hydroxyacide dehydrogenase from *Lactococcus lactis*. For the nucleic acid sequence, it may be referred to the Enzyme Commission number E.C. 1.1.1.145.

For the amino acid sequence of KDH, it may be referred to the access number WP_011835036.1. in the UniProt database and/or to the access number WP_010905887.1 in the UniProt database.

Cystathionine Gamma-Lyase

CYS3 is the cystathionine gamma-lyase from *Saccharomyces cerevisiae*. For the amino acid sequence of CYS3, it may be referred to the access number NP_009390 in the UniProt database.

For the nucleic acid sequence, it may be referred to the access number NM_001178157 in the NCBI database.

Cystathionine Beta-Synthase

CYS4 is the cystathionine beta-synthase from *Saccharomyces cerevisiae*. For the amino acid sequence of CYS4, it may be referred to the access number NP_011671 in the UniProt database.

For the nucleic acid sequence, it may be referred to the access number NM_001181284 in the NCBI database.

Second Further Embodiments of Oxaloacetate Derivatives-Producing Recombinant Yeast According to these second further embodiments of an oxaloacetate derivatives-producing recombinant yeast according to the invention, further genetic engineering of the recombinant yeast is performed with the aim of increasing the production of threonine.

According to these embodiments, genetic changes are introduced so as to:

(A) over express and/or put under the control of a inducible or repressible promoter at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP;

(B) over express and/or put under the control of a inducible or repressible promoter at least one nucleic acid encoding an homoserine kinase THR1;

(C) over express and/or put under the control of a inducible or repressible promoter at least one nucleic acid encoding a threonine synthase THR4; and (D) (i) put under the control of a inducible or repressible promoter at least one nucleic acid encoding an aspartokinase HOM3; and/or (ii) over express and/or put under the control of a inducible or repressible promoter at least one nucleic acid encoding an aspartate kinase AK.

to these embodiments, at least one nucleic acid encoding an aspartate transaminase AAT2 can optionally be overexpressed and/or is under the control of an inducible or repressible promoter.

According to these embodiments, at least one nucleic acid encoding a glutamate dehydrogenase GDH that converts oxo-glutarate to glutamate can optionally be overexpressed and/or is under the control of an inducible or repressible promoter.

According to these embodiments, at least one nucleic acid encoding an homoserine dehydrogenase HOM6 can also optionally be overexpressed.

According to these embodiments, (a) at least one, preferably all, endogenous nucleic acid encoding an homoserine-O-acetyltransferase MET2 can be deleted, or (b) at least one, preferably all, nucleic acid encoding an homoserine-O-acetyltransferase MET2 can be under the control of an inducible or repressible promoter and/or be in a destabilized form.

According to these embodiments, (a) at least one, preferably all, endogenous nucleic acid encoding a methionine synthase MET17 can be deleted, or (b) at least one, preferably all, nucleic acid encoding a methionine synthase MET17 can be under the control of an inducible or repressible promoter and/or be in a destabilized form.

According to these embodiments, at least one nucleic acid encoding a probable transporter AQR1 can optionally be overexpressed.

Threonine Synthase THR4

Threonine synthase enzyme is a protein which is described in the art for catalyzing the $H_2O$-dependent dephosphorylation of O-phospho-L-homoserine to L-threonine. Threonine synthase encoded by the genome of *Saccharomyces cerevisiae* may be termed THR4.

A method implemented to measure the activity level of threonine synthase belongs to the general knowledge of the one skilled in the art.

In this regard, the one skilled in the art may advantageously refer to the method described by in Schildkraut and Greer Journal of Bacteriology, (1973), Vol. 115, p. 777-785.

Preferred threonine synthase in the present specification is an enzyme having an EC number of no EC 4.2.3.1.

For the amino acid sequence of the threonine synthase from *Saccharomyces cerevisiae*, the one skilled in the art may refer to the accession number NP_009982.1 in the UniProt database. For the nucleic acid sequence, it may be referred to the access number NM_001178767.1 in the UniProt database.

Aspartate Kinase AK

The aspartate kinase enzyme is a protein which is described in the art for catalyzing the conversion of L-aspartate in the presence of ATP into 4-phospho-L-aspartate. The aspartate kinase encoded by the genome of *Bacillus subtilis* may be termed AK.

A method implemented to measure the activity level of aspartate kinase belongs to the general knowledge of the one skilled in the art and is the same as the one indicated previously for aspartokinase.

For the amino acid sequence of the aspartate kinase from *Bacillus substilis*, the one skilled in the art may refer to the accession number NP_389558.2 in the UniProt database. For the nucleic acid sequence, it may be referred to the one disclosed in the access number NC 000964.3 in the NCBI database.

Probable Transporter AQR1

AQR1 is a transporter from *Saccharomyces cerevisiae*. For the amino acid sequence of AQR1 it may be referred to the access number NP_014334 in the UniProt database. For the nucleic acid sequence, it may be referred to the access number NM_001182903 in the NCBI database.

Promoters

As it is disclosed herein, the expression of the genes of interest that have been genetically engineered for obtaining a recombinant yeast according to the invention comprise appropriate regulatory sequences that are functional in yeast cells, including in *Saccharomyces cerevisiae.*

As disclosed in the present specification, various promoters may be used for the desired expression of the coding sequences of interest, which include (i) constitutive strong promoters (also called strong promoters in the present text), (ii) constitutive weak promoters (also called weak promoters in the present text) and (iii) inducible or repressible promoters. A list of yeast promoter with their relative activities in different media can be found in Keren et al. (2013) Molecular Systems Biology 9:701.

Promoters allowing the constitutive over-expression of a given gene, may be found in literature (Velculescu et al. (1997) Cell 88, 243-251).

Strong promoters more particularly interesting in the present invention may be selected from the group comprising:

pTDH3 (SEQ ID No 37),
pENO2 (SEQ ID No 38),
pTEF KI (SEQ ID No 39),
pTEF3 (SEQ ID No 40),
pTEF1 (SEQ ID No 41),
pADH1 (SEQ ID No 42),
pGMP1 (SEQ ID No 43),
pFBA1 (SEQ ID No 44),
pPDC1 (SEQ ID No 45),
pCCW12 (SEQ ID No 46), and
pGK1 (SEQ ID No 47).

According to a particular embodiment, the strong promoter according to the invention is, independently, selected from the group consisting of pTDH3, pENO2, pTEF-K1, pTEF3, pTEF1, pADH1, pGMP1, pFBA1, pPDC1, pCCW12 and pGK1.

Weak promoters more particularly interesting in the present invention may be selected from the group comprising:

pURA3 (SEQ ID No 49),
pRPLA1 (SEQ ID No 50),
pNUP57 (SEQ ID No 129), and
pGAP1 (SEQ ID No 130).

According to a particular embodiment, the weak promoter according to the invention is, independently, selected from the group consisting of pURA3 pRPLA1, pNUP57 and pGAP1.

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast of the invention comprising inducible or repressible promoters can be decided and thus controlled by the man skilled in the art.

For example, increasing the quantity of methionine in a culture medium of a recombinant yeast according to the invention comprising a pSAM4 promoter will induce and thus increase transcription of the gene under the control of this promoter. On the contrary, reducing the quantity of methionine in said culture medium will lead to a repression, and thus a reduced, transcription of the gene under the control of this promoter.

In another example, increasing the quantity of copper in a culture medium of a recombinant yeast according to the invention comprising a pCTR1 promoter will repress and thus decrease transcription of the gene under the control of this promoter. On the contrary, reducing the quantity of copper in said culture medium will lead to an induced, and thus an increased, transcription of the gene under the control of this promoter.

For this reason, the following promoters are referred to in the present text as being "inducible or repressible promoters".

According to a first embodiment, inducible or repressible promoters according to the invention may be selected from the group comprising promoters inducible or repressible with copper, promoters inducible or repressible with methionine and promoters inducible or repressible with threonine, and are in particular selected from the group consisting of:

pSAM4—methionine inducible or repressible (SEQ ID No 51),
pCUP1-1—copper inducible or repressible (SEQ ID No 52),
pCUP1.cgla—copper inducible or repressible (SEQ ID No 53),
pCUP1.sba—copper inducible or repressible (SEQ ID No 54),
pACU1—copper inducible or repressible (SEQ ID No 55),
pACU2—copper inducible or repressible (SEQ ID No 56),
pACU3p—copper inducible or repressible (SEQ ID No 57),
pACU4p—copper inducible or repressible (SEQ ID No 58),
pACU5—copper inducible or repressible (SEQ ID No 59),
pACU6—copper inducible or repressible (SEQ ID No 60),
pACU7—copper inducible or repressible (SEQ ID No 61),
pACU8—copper inducible or repressible (SEQ ID No 62),
pACU9—copper inducible or repressible (SEQ ID No 63),
pACU10p—copper inducible or repressible (SEQ ID No 64),
pACU11—copper inducible or repressible (SEQ ID No 65),
pACU12—copper inducible or repressible (SEQ ID No 66),
pACU13—copper inducible or repressible (SEQ ID No 67),
pACU14—copper inducible or repressible (SEQ ID No 68),
pACU15—copper inducible or repressible (SEQ ID No 69),
pGAL/CUP1p—copper inducible or repressible (SEQ ID No 70),
pCRS5—copper inducible or repressible (SEQ ID No 71), and
pCHA1—threonine inducible or repressible (SEQ ID No 72).

According to this embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with lysine, promoters inducible or repressible with glucose and promoters inducible or repressible with methionine, and in particular selected from the group consisting of:

pCTR1—copper inducible or repressible (SEQ ID No 73),
pCTR3—copper inducible or repressible (SEQ ID No 74),
pCUR1—copper inducible or repressible (SEQ ID No 75),
pCUR2—copper inducible or repressible (SEQ ID No 76),
pCUR3—copper inducible or repressible (SEQ ID No 77),
pCUR4—copper inducible or repressible (SEQ ID No 78),
pCUR5p—copper inducible or repressible (SEQ ID No 79),
pCUR6—copper inducible or repressible (SEQ ID No 80),
pCUR7—copper inducible or repressible (SEQ ID No 81),
pCUR8—copper inducible or repressible (SEQ ID No 82),
pCUR9—copper inducible or repressible (SEQ ID No 83),
pCUR10—copper inducible or repressible (SEQ ID No 84),
pCUR11—copper inducible or repressible (SEQ ID No 85),
pCUR12—copper inducible or repressible (SEQ ID No 86),
pCUR13—copper inducible or repressible (SEQ ID No 87),
pCUR14—copper inducible or repressible (SEQ ID No 88),
pCUR15—copper inducible or repressible (SEQ ID No 89),
pCUR16—copper inducible or repressible (SEQ ID No 90),
pCUR17—copper inducible or repressible (SEQ ID No 91),
pLYS1—lysine inducible or repressible (SEQ ID No 92),
pLYS4—lysine inducible or repressible (SEQ ID No 93),
pLYS9—lysine inducible or repressible (SEQ ID No 94),
pLYR1p—lysine inducible or repressible (SEQ ID No 95),
pLYR2p—lysine inducible or repressible (SEQ ID No 96),
pLYR3p—lysine inducible or repressible (SEQ ID No 97),
pLYR4p—lysine inducible or repressible (SEQ ID No 98),
pLYR5p—lysine inducible or repressible (SEQ ID No 99),
pLYR6p—lysine inducible or repressible (SEQ ID No 100),
pLYR7p—lysine inducible or repressible (SEQ ID No 101),
pLYR8—lysine inducible or repressible (SEQ ID No 102),
pLYR9—lysine inducible or repressible (SEQ ID No 103),
pLYR10—lysine inducible or repressible (SEQ ID No 104),
pLYR11—lysine inducible or repressible (SEQ ID No 105),
pMET17—methionine inducible or repressible (SEQ ID No 106),
pMET6—methionine inducible or repressible (SEQ ID No 107),
pMET14—methionine inducible or repressible (SEQ ID No 108),
pMET3—methionine inducible or repressible (SEQ ID No 109),
pSAM1—methionine inducible or repressible (SEQ ID No 110),
pSAM2—methionine inducible or repressible (SEQ ID No 111),
pMDH2—glucose inducible or repressible (SEQ ID No 48),
pJEN1—glucose inducible or repressible (SEQ ID No 131),
pICL1—glucose inducible or repressible (SEQ ID No 132),
pADH2—glucose inducible or repressible (SEQ ID No 133), and
pMLS1—glucose inducible or repressible (SEQ ID No 134).

According to this embodiment, the inducible or repressible promoter according to the invention can, independently, be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

The activity of these promoters is thus repressed by the increasing presence of methionine, copper, lysine or glucose as indicated above, and their activity increases, i.e. is induced, when the quantity of methionine, copper, lysine or glucose is reduced.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

In a more particular embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

More particularly, said promoters, identical or different, may be preferably characterized by a sequence of nucleic acid selected from the group consisting of sequences having at least 80% identity with sequences SEQ ID NO: 37 to 111 and 129 to 134.

Synthetic promoters as described in Blazeck & Alper (2013) Biotechnol. J. 8 46-58 can also be used.

The strong, weak and inductible or repressible promoters of the invention can originate from any organism from the Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolitica* and *Cyberlindnera jadinii.*

The strong, weak and inductible or repressible promoters of the invention can preferably originate from an organism selected from the group consisting of *Saccharomyces cerevisiae, Saccharomyces castelii, Saccharomyces bayanus, Saccharomyces arboricola, Saccharomyces kudriavzevii* and *Kluveromyces lactis.*

Terminators

As it is disclosed herein, the expression of the genes of interest that have been genetically engineered for obtaining a recombinant yeast according to the invention comprise appropriate transcription terminator sequences that are functional in yeast cells, including in *Saccharomyces cerevisiae.*

Said transcription terminators, identical or different, may be found in literature Yamanishi et al., (2013) ACS synthetic biology 2, 337-347.

Terminators more particularly interesting in the present invention may be selected from the group comprising:

- tTDH2 from the gene coding for Glyceraldehyde-3-phosphate dehydrogenase, isozyme 2 (TDH2 gene=Sequence SEQ ID No 112),
- tCYC1 (=Sequence SEQ ID No 113),
- tTDH3 (=Sequence SEQ ID No 114), and
- tADH1 from gene coding for the alcohol dehydrogenase (ADH1 gene=Sequence SEQ ID No 115),
- tADH2 from gene coding for the alcohol dehydrogenase (ADH2 gene=Sequence SEQ ID No 116),
- tTPI1 from the gene encoding for the Triose Phosphate Isomerase (TPI1 gene=Sequence SEQ ID No 117),
- tMET17 from the gene encoding for the O-acetyl homoserine-O-acetyl serine sulfhydrylase (Met17 gene=Sequence SEQ ID No 118),
- tENO2 from the gene coding for Enolase II (ENO2 gene=Sequence SEQ ID No 119),
- tMET3 (=Sequence SEQ ID No 120), and
- tPGK1 from the gene encoding for the 3-phosphoglycerate kinase (PGK1 gene=Sequence SEQ ID No 121),
- tDIT1 (=Sequence SEQ ID No 122)
- tRPL3 (=Sequence SEQ ID No 123)
- tRPL41B (=Sequence SEQ ID No 124)
- tRPL15A (=Sequence SEQ ID No 125)
- tIDP1 (=Sequence SEQ ID No 126).

More particularly, said terminator, identical or different, may be preferably characterized by a sequence of nucleic acid selected from the group consisting of sequences having at least 80% identity with sequences SEQ ID NO: 112 to 126.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus *Saccharomyces, Candida Ashbya, Dekkera, Pichia* (*Hansenula*), *Debaryomyces, Clavispora, Lodderomyces, Yarrowia, Zigosaccharomyces, Schizosaccharomyces, Torulaspora, Kluyveromyces, Brettanomycces, Cryptococcus* or *Malassezia.*

More preferentially, the yeast may be Crabtree positive yeast of genus of *Saccharomyces, Dekkera, Schizosaccharomyces, Kluyveromyces, Torulaspora Zigosaccharomyces*, or. *Brettanomycces*

More preferentially, the yeast may be from the species *Saccharomyces cerevisiae, Saccharomyces boulardii, Saccharomyces douglasii, Saccharomyces bayanus* or. or *Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa, Torulaspora glabrata*

More preferentially, the recombinant yeast may belong to the *Saccharomyces* genus, and preferably to the *Saccharomyces cerevisiae* species.

As above-mentioned, a recombinant yeast according to the invention has a pyruvate decarboxylase activity which is reduced by insertion of at least one DNA construct(s) selected from those disclosed in the present specification.

Methods implemented to insert a specific DNA construct within a gene belong to the general knowledge of a man skilled in the art. A related method is described in more details in the herein after examples.

Culture Conditions

The present invention also relates to the use of a recombinant yeast such as above-defined, for the production of oxaloacetate derivatives.

The present invention further relates to a method of production of oxaloacetate derivatives comprising the following steps:

- providing a recombinant microorganism as previously described, cultivating the recombinant microorganism in a culture medium containing a source of carbon, and
- recovering the oxaloacetate derivatives.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the oxaloacetate derivatives production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing oxaloacetate derivatives according to the invention may further comprise, between steps (a) and (c), an intermediate step (b) consisting of cultivating the yeast cells in the said optimal culture medium.

Purification of Oxaloacetate Derivatives

According to a specific aspect of the invention, the fermentative production of oxaloacetate derivatives comprises a step of isolation of the oxaloacetate derivatives from the culture medium. Recovering the oxaloacetate derivatives from the culture medium is a routine task for a man skilled in the art. It may be achieved by a number of techniques well known in the art including but not limiting to distillation, gas-stripping, pervaporation, selective precipitation or liquid extraction. The expert in the field knows how to adapt parameters of each technique dependant on the characteristics of the material to be separated.

The yeast as model of microorganism in the present invention has been retained in that the synthesized oxaloacetate derivatives is/are entirely exported outside the cells, thus simplifying the purification process.

The synthesized oxaloacetate derivatives may be collected by distillation. Distillation may involve an optional component different from the culture medium in order to facilitate the isolation of oxaloacetate derivatives by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane.

Oxaloacetate Derivatives

Oxaloacetate derivatives according to the invention are compounds that can be produced by a microorganism, in particular a yeast, using oxaloacetate as substrate or co-substrate upstream in the biosynthesis pathway after modification by at least one enzyme naturally and/or artificially present in the microorganism producing the oxaloacetate according to the invention, in particular in the yeast producing the oxaloacetate according to the invention.

Examples of such oxaloacetate derivatives can for example be selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine and ethyl-homoserine.

Throughout the description, including the claims, the expression "comprising a" should be understood as being synonymous with "comprising at least one", unless otherwise specified.

The terms "between . . . and . . . " and "ranging from . . . to . . . " should be understood as being inclusive of the limits, unless otherwise specified.

The examples and figures which follow are presented by way of illustration and without implied limitation of the invention.

EXAMPLES

Example 1: Protocol for Making a Recombinant *Saccharomyces cerevisiae* Strain According to the Invention All the hereinafter implemented recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes:

- ade2, his3, leu2, trp1 and ura3 are auxotrophy marker genes.
- Lowercase letters mean that the considered gene is inactive, uppercase letters reflect an active gene.
- "::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.
- "gene.K1" means that the gene originates from *Kluyveromyces lactis*.

More particularly, the coding sequences to be cloned were artificially synthesized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

It should be noted that, in the same cultural conditions as those of the following examples, a wild-type *Saccharomyces cerevisiae* strain (i.e. a non-recombinant strain) does not produce a detectable amount of oxaloacetate derivatives, and in particular does not produce a detectable amount of methionine or ethyl-homoserine.

Example 2: Comparative Examples of the Invention for the Production of Oxaloacetate Derivatives A. Firstly, two recombinant strains were obtained: YA2326-14 and YA2408-27, in order to in particular produce methionine.

These two strains are as follows:

Strain YA2326-14: Matα, ade2, agp3::loxP, bap3::loxP, can1-100, gap1::loxP, gnp1::loxP, his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, sam1::loxP, trp1::[pTDH3-GDH-2.Eca-pCUP1-1-HOM3-TRP1]×5, ura3::[pTEF3-MET17-pTDH3-PPC-5.Ec-URA3]×7

Strain YA2408-27: Matα, ade2, agp3::loxP, bap3::loxP, gap1::loxP, gnp1::loxP, his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, sam1::loxP, trp1::[pACU1-AAT2-pCUP1-1-HOM3-TRP1]×3, ura3::[pTEF3-MET17-pTDH3-PPC-5.Ec-URA3]×7

A third strain, DA705-1, is obtained comprising the combined modifications of the two strains YA2326-14 and YA2408-27. Accordingly, DA705-1 is a strain according to the invention.

DA705-1: (YA2408-27×YA2326-14): ade2/ade2, agp3::loxP/agp3::loxP, bap3::loxP/bap3::loxP, CAN1-100/can1-100, gap1::loxP/gap1::loxP, gnp1::loxP/gnp1::loxP, his3::[pTDH3-MHPF.Ec-HIS3]×6/his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1]/hom3::[pCUP1-1-HOM3-pADH1-HOM2-pADH1-MET2-pRPLA1-HOM6-pENO2-MET17-pTEF3-AQR1], leu2/leu2, mae1::[ADE2.K1-pENO2-PYC2-pTEF3-MET17-pTEF1-TPO1-1-pTDH3-METX.Cg]/mae1::

[ADE2.K1-pENO2-PYC2-pTEF3-MET17-pTEF1-TPO1-1-pTDH3-METX.Cg], met19::[pENO2-MET19-pTEF3-GND1]/met19::[pENO2-MET19-pTEF3-GND1], mup3::loxP/mup3::loxP, pdc1::loxP/pdc1::loxP, pdc6::loxP/pdc6::loxP, sam1::loxP/sam1::loxP, trp1::[pACU1-AAT2-pCUP1-1-HOM3-TRP1]×3/trp1::[pTDH3-GDH-2.Eca-pCUP1-1-HOM3-TRP1]×5, ura3::[pTEF3-MET17-pTDH3-PPC-5.Ec-URA3]×7/ura3::[pTEF3-MET17-pTDH3-PPC-5.Ec-URA3]×7

PPC-5 is a more stable form of PPC wherein an alanine has been added in N+1.

All these strains were grown for 24 hours in YE (Yeast Extract) 2%, Glucose 8%, $(NH_4)_2SO_4$ 50 mM, and $CH_3SNa$ 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While a non-recombinant strain does not produce a detectable quantity of methionine, themethionine amounts obtained with these different strains are respectively:

YA2326-14: 1.47 $g/L^{-1}$.

YA2408-27: 1.5 $g/L^{-1}$.

DA705-1: 1.9 $g/L^{-1}$.

It results from this comparative experiment that a recombinant strain comprising the modifications according to the invention produces a greater amount of methionine when cultured in the same conditions as other recombinant strains not comprising all the genetic modifications according to the invention.

B. Three other recombinant strains have also been obtained: YA1919-13, YA2058-33 and YA2058-27 in order to in particular produce methionine.

These three strains are as follows:

Strain YA1919-13: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6

YA2058-23: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pCUP1-1-HOM3-TRP1]×2

YA2058-37: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC5.Ec-URA3]×7, his3::[pTDH3-MHPF.Ec-HIS3]×6, trp1::[pCUP1-1-HOM3-TRP1]×3

The three strains were grown for 48 hours in YE (Yeast Extract) 2%, Glucose 8%, $(NH_4)_2SO_4$ 50 mM, and MeSNa 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While a non-recombinant strain does not produce a detectable quantity of methionine, the methionine amounts obtained with these three strains are respectively:

YA1919-13: 3.9 $g/L^{-1}$.

YA2058-23: 6.1 $g/L^{-1}$.

YA2058-37: 7.1 $g/L^{-1}$.

It results from this comparative experiment that a recombinant strain comprising the modifications according to the invention produces a greater amount of methionine when cultured in the same conditions as other recombinant strains not comprising all the genetic modifications according to the invention.

C. In addition to strain YA1919-13, two other recombinant strains have also been obtained: YA2160-40 and YA2230-9.

YA2160-40: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pSAM4-TPO1-pCUP1-1-HOM3-TRP1]×5

YA2230-9: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pTDH3-GDH.E.Ca-pCUP1-1-HOM3-TRP1]×5 The three strains were grown for 48 hours in YE (Yeast Extract) 2%, Glucose 8%, $(NH_4)_2SO_4$ 50 mM, and MeSNa 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While a non-recombinant strain does not produce a detectable quantity of methionine, the methionine amounts obtained with these three strains are respectively:

YA1919-13: 3.9 $g/L^{-1}$.

YA2160-40: 7.4 $g/L^{-1}$.

YA2230-9: 9.6 $g/L^{-1}$.

It results from this comparative experiment that a recombinant strain comprising the modifications according to the invention produces a greater amount of methionine when cultured in the same conditions as other recombinant strains not comprising all the genetic modifications according to the invention.

D. In addition to strain YA1919-13, another recombinant strain has also been obtained: YA2231-8.

YA2231-8: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.Kl-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pSAM4-AAT2-pCUP1-1-HOM3-TRP1]×4

The two strains were grown for 48 hours in YE (Yeast Extract) 2%, Glucose 8%, $(NH_4)_2SO_4$ 50 mM, and MeSNa 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While a non-recombinant strain does not produce a detectable quantity of methionine, the methionine amounts obtained with these three strains are respectively:

YA1919-13: 3.9 $g/L^{-1}$.

YA2231-8: 7 $g/L^{-1}$.

It results from this comparative experiment that a recombinant strain comprising the modifications according to the invention produces a greater amount of methionine when cultured in the same conditions as other recombinant strains not comprising all the genetic modifications according to the invention.

E. An additional recombinant strain according to the invention was obtained: YA3083-58C.

Accordingly, this strain is as follows:

YA3083-58C: MAT-a, agp3::loxP, gap1::loxP, gnp1::loxP, his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET25-tPGK1, pTEF3-AQR1], leu2, lyp1::[pCUP1-1-MET17.Rp-tRPL15A-pACU6-METX-1.Cg-tTPI1]×7, mae1::[ADE2.Kl-RS, pTEF3-MET17-tCYC1, pTEF1-TPO1-1-tADH1, pTDH3-METX.Cg-tADH2], met19::[pENO2-MET19-tCYC1, pTEF3-GND1], mup3::loxP, pdc1::loxP, pdc6::loxP, pyk2::[LEU2.Kl-pCUP1-HOM2-1-tTDH3], sam1::loxP, trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7

The strain was grown for 48 hours in YE (Yeast Extract) 2%, Glucose 8%, $(NH_4)_2SO_4$ 50 mM, and MeSNa 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of methionine, the strain YA3083-58C produced 2.2 $g \cdot L^{-1}$ of methionine in 24 hours.

F. Additional experiments have been performed in a fermenter with the two following recombinant strains obtained according to the invention:

DA964-31: MAT-a/MAT-α, ade2/ade2, agp3::loxP/agp3::loxP, bap3::loxP/bap3::loxP, CAN1-100/can1-100, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2,pENO2-MET17-tPGK1, pTEF3-AQR1], leu2/leu2, mae1::[ADE2.Kl-RS, pTEF3-MET17-tCYC1, pTEF1-TPO1-1-tADH1, pTDH3-METX.Cg-tADH2]/mae1::[ADE2.Kl-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1,pTEF3-GND1], mup3::loxP/mup3::loxP, pdc1::loxP/pdc1::loxP, pdc6::loxP/pdc6::loxP, sam1::loxP/sam1::[LEU2.Kl-pACU8-HOM2-1-tRPL15A, pACU5-TPO1-3-tTPI1], trp1::[pACU1-AAT2-tRPL3-pCUP1-1-HOM3-tIDP1]×3/trp1::[pTDH3-GDH-.Eca-tRPL3-pCUP1-1-HOM3-tIDP1-TRP1]×5, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1047-1: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2,pRPLA1-HOM6-tTDH2,pENO2-MET17-tPGK1, pTEF3-AQR1]/hom3::[pADH1-HOM2-tTPI1,pPDC1-MET2-tADH2,pRPLA1-HOM6-tTDH2,pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.Kl-RS, pTEF3-MET17-tCYC1, pTEF1-TPO1-1-tADH1, pTDH3-METX.Cg-tADH2]/mae1::[ADE2.Kl-RS, pTEF3-MET17-tCYC1,pTEF1-TPO1-1-tADH1,pTDH3-METX.Cg-tADH2], met19::[pENO2-MET19-tCYC1,pTEF3-GND1]/met19::[pENO2-MET19-tCYC1,pTEF3-GND1], mup3::loxP/mup3::loxP, pdc1::loxP/pdc1::loxP, pdc6::loxP/pdc6::loxP, pyk2::[LEU2.Kl-pCUP1-1-HOM2-1-tTDH3]/pyk2::[LEU2.Kl-pCUP1-1-HOM2-1-tTDH3], sam1::loxP/sam1::loxP, trp1::[pACU1-AAT2-tRPL3-pCUP1-1-HOM3-tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

TPO1-1 is an artificial allele in which the lysines 10, 49, 86, 143, 144 and 145 are replaced by arginines. HOM2-1 is an artificial allele of HOM2 in which the serine in position 39 is mutated to glutamate.

These strains have been cultivated in a fermenter according to the "fed batch" technic such as described in Peng et al. (2017) biotechnology for biofuels 10-43 in YE (Yeast Extract) 2%, Glucose 8%, $(NH_4)_2SO_4$ 50 mM and 500 μM of $CuSO_4$.

Moreover, the culture medium contained either and 1 g/L of MeSH or and 1 g/L of MeSNA.

The production of methionine was then measured as previously described. While a non-recombinant strain does not produce a detectable quantity of methionine, the methionine amounts obtained with these two strains are respectively:

(i) in the presence of MeSH:

DA964-31: 32 $g/L^{-1}$ after 70 hours.

DA1047-1: 16 $g/L^{-1}$ after 50 hours.

(ii) in the presence of MeSNa:

DA964-31: 20 $g/L^{-1}$ after 63 hours.

DA1047-1: 11 $g/L^{-1}$ after 47 hours.

A higher quantity of methionine is obtained when the strains are cultivated in presence of MeSH instead of MeSNa. Here too, the corresponding non recombinant strains did not produced any measurable quantity of methionine.

G. Two recombinant strains according to the invention, illustrated here-after, have also been assayed for methionine.

Strain YA2573-36B: Mat a, agp3::loxP, gap1::loxP, gnp1::loxP, his3::[pTDH3-GDH-2.Eca-pPDC1-MHPF.Ec-HIS3]×5, hom3::[pCUP1-1-HOM3-pADH1-HOM2-pADH1-MET2-pRPLA1-HOM6-pENO2-MET17-pTEF3-AQR1], leu2, mae1::[ADE2.Kl-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, pyk1::[TRP1.Kl-RS-pTEF3-AAT2-pCUP1-1-MET19-pACU1-PEPCK-1.Ec-pMET17-PYK1], pyk2::[LEU2.Kl-RS-pADH1-HOM2-1], sam1::loxP, trp1::[pACU3p-HOM3-pACU3p-PPC-5.Ec-TRP1]×8, ura3::[pTEF3-MET17-pTDH3-PPC-5.Ec-URA3]×7

Strain YA2691-2: Mat a, agp3::loxP, gap1::loxP, gnp1::loxP, his3::[pTDH3-GDH-2.Eca-pPDC1-MHPF.Ec-HIS3]×5, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, pyk1::[TRP1.Kl-RS-pTEF3-AAT2-pCUP1-1-MET19-pACU1-PEPCK-1.Ec-pMET17-PYK1], pyk2::[LEU2.Kl-RS-pADH1-HOM2-1], sam1::loxP, sam3::[pCUP1-1-CGS1-mut-pACU6-THR1-SAM3]×4, trp1::[pACU3p-HOM3-pACU3p-PPC-5.Ec-TRP1]×8, ura3::[pTEF3-MET17-pTDH3-PPC-5.Ec-URA3]×7

PEPCK-1 is a form of PEPCK stabilized by modification of the Arginine amino acid in position 2 by a Glycine.

The two strains were grown for 24 hours in YE (Yeast Extract) 2%, Glucose 8%, $(NH_4)_2SO_4$ 50 mM, and $CH_3SNa$ 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While a non-recombinant strain does not produce a detectable quantity of methionine, the methionine amounts obtained with these two strains are respectively:

YA2573-36B: 1.8 $g/L^{-1}$.

YA2691-2: 2.1 $g/L^{-1}$.

H. Two recombinant strains according to the invention, illustrated here-after, have also been assayed for methionine and KMB production.

These two strains are:

YA3344-12: MAT-α, ADE2, agp3::loxP, aro10::[pENO2-SAM2-pENO2-ARO8-tTDH3]×6, bap3::loxP, CAN1-100, gap1::loxP, gnp1::loxP, his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1], leu2, lyp1::[pCUP1-MET17.Rp-1-tRPL15A-pACU6-METX-1.Cg-tTPI1]×5, mae1::[ADE2.Kl-RS, pTEF3-MET17-tCYC1, pTEF1-TPO1-1-tADH1, pTDH3-METX.Cg-tADH2], met19::[pENO2-MET19-tCYC1, pTEF3-GND1], mup3::loxP, pdc1::loxP, pdc6::loxP, sam1::loxP, sam2::[LEU2.Kl-pACU8-HOM2-1-tRPL15A, pACU5-TPO1-3-tTPI1], trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7

DA1025-9: MAT-a/MAT-α, ade2/ade2, agp3::loxP/agp3::loxP, ARO10/aro10::[pENO2-SAM2-pENO2-ARO8-tTDH3]×11, bap3::loxP/bap3::loxP, CAN1-100/can1-100, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, mae1::[ADE2.Kl-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, sam1::loxP/sam1::loxP, sam2::[LEU2.Kl-pACU8-HOM2-1-tRPL15A]/sam2::[LEU2.K1-pACU8-HOM2-1-tRPL15A], trp1::[pACU1-AAT2-tRPL3-pCUP1-1-HOM3-tIDP1]×3/trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

These strains have been cultivated in a fermenter according to the "fed batch" technic such as described in Peng et al. (2017) biotechnology for biofuels 10-43. doi: 10.1186/s13068-017-0728-x in YE (Yeast Extract) 2%, Glucose 8%, $(NH_4)_2SO_4$ 50 mM, 1 g/L of MeSNa and 500 μM of $CuSO_4$.

The production of methionine and of KMB was then measured as described previously and the methionine and KMB amounts obtained with these two strains are respectively:

(i) YA3344-12: 0.5 $g/L^{-1}$ of methionine and 1.2 $g/L^{-1}$ of KMB after 39 hours.

(ii) DA1025-9: 7.5 $g/L^{-1}$ of methionine and 8 $g/L^{-1}$ of KMB after 39 hours.

In these conditions of culture, the corresponding non-recombinant strains do not produce a detectable quantity of KMB.

I. Three recombinant strains according to the invention, illustrated here-after, have also been assayed for methionine and HMB production.

These three strains are:

DA1047-1: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2,pRPLA1-HOM6-tTDH2,pENO2-MET17-tPGK1,pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.Kl-RS, pTEF3-MET17-tCYC1, pTEF1-TPO1-1-tADH1,pTDH3-METX.Cg-tADH2]/mae1::[ADE2.Kl-RS, pTEF3-MET17-tCYC1,pTEF1-TPO1-1-tADH1,pTDH3-METX.Cg-tADH2], met19::[pENO2-MET19-tCYC1,pTEF3-GND1]/met19::[pENO2-MET19-tCYC1,pTEF3-GND1], mup3::loxP/mup3::loxP, pdc1::loxP/pdc1::loxP, pdc6::loxP/pdc6::loxP, pyk2::[LEU2.Kl-pCUP1-1-HOM2-1-tTDH3]/pyk2::[LEU2.Kl-pCUP1-1-HOM2-1-tTDH3], sam1::loxP/sam1::loxP, trp1::[pACU1-AAT2-tRPL3-pCUP1-1-HOM3-tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1555-2: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2,pRPLA1-HOM6-tTDH2,pENO2-MET17-tPGK1, pTEF3-AQR1]/hom3::[pADH1-HOM2-tTPI1,pPDC1-MET2-tADH2,pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.Kl-RS, pTEF3-MET17-tCYC1, pTEF1-TPO1-1-tADH1, pTDH3-METX.Cg-tADH2]/mae1::[ADE2.K1-RS, pTEF3-MET17-tCYC1,pTEF1-TPO1-1-tADH1,pTDH3-METX.Cg-tADH2],met19::[pENO2-MET19-tCYC1,pTEF3-GND1]/met19::[pENO2-MET19-tCYC1,pTEF3-GND1], mup3::loxP/mup3::loxP, pdc1::loxP/pdc1::loxP, pdc6::loxP/pdc6::loxP, pyk2::[LEU2.Kl-pCUP1-1-HOM2-1-tTDH3]/pyk2::[LEU2.K1-pCUP1-1-HOM2-1-tTDH3], sam1::loxP/sam1::loxP, sam3::[pCCW12-ARO8-tRPL15A-pTDH3-KDH1-0.L1-tTPI1]×1/sam3::[pCCW12-ARO8-tRPL15A-pTDH3-

KDH1-0.L1-tTPI1]×2, trp1::[pACU1-AAT2-tRPL3-pCUP1-1-HOM3-tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1156-11: DA1555-2: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2,pRPLA1-HOM6-tTDH2,pENO2-MET17-tPGK1, pTEF3-AQR1]/hom3::[pADH1-HOM2-tTPI1,pPDC1-MET2-tADH2,pRPLA1-HOM6-tTDH2,pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.Kl-RS, pTEF3-MET17-tCYC1, pTEF1-TPO1-1-tADH1, pTDH3-METX.Cg-tADH2]/mae1::[ADE2.Kl-RS, pTEF3-MET17-tCYC1,pTEF1-TPO1-1-tADH1, pTDH3-METX.Cg-tADH2], met19::[pENO2-MET19-tCYC1,pTEF3-GND1]/met19::[pENO2-MET19-tCYC1,pTEF3-GND1], mup3::loxP/mup3::loxP, pdc1::loxP/pdc1::loxP, pdc6::loxP/pdc6::loxP, pyk2::[LEU2.Kl-pCUP1-1-HOM2-1-tTDH3]/pyk2::[LEU2.Kl-pCUP1-1-HOM2-1-tTDH3], sam1::loxP/sam1::loxP, sam3::[pCCW12-ARO8-tRPL15A-pTDH3-KDH2-0.L1-tTPI1]×1/sam3::[pCCW12-ARO8-tRPL15A-pTDH3-KDH2-0.L1-tTPI1]×2, trp1::[pACU1-AAT2-tRPL3-pCUP1-1-HOM3-tIDP1]×3/trp1::[pACU3p-HOM3-tRPL3-pACU3p-PPC-1.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

The strains have been cultivated in erlenmeyer: Yeast extract 2%, Glucose 8%, CuSO4 500 μM, $CH_3SNa$ 10 g/l for 24h. Methionine, KMB and HMB are dosed in the culture supernatant by LC-MS (LC: Column: Hi-Plex H 300*7.7 mm Ref PL1170-6830 Agilent, eluant 85% Acide formique 0.5%, 15% Acetonitrile, ionisation ESI−, mass spectrometer Quattro Micro API Waters).

In these conditions of culture, the corresponding non-recombinant strains do not produce a detectable quantity of KMB and are not able to produce HMB.

The amounts of methionine, of KMB and of HMB obtained with these three strains are respectively:

(i) DA1047-1: 2.3 g/$L^{-1}$ of methionine, 0.3 g/$L^{-1}$ of KMB and 0.1 g/$L^{-1}$ of HMB (after 48 hours).

(ii) DA1555-2: 0.3 g/$L^{-1}$ of methionine, 0.15 g/$L^{-1}$ of KMB and 2.8 g/$L^{-1}$ of HMB after 36 hours.

(iii) DA1156-11: 0.4 g/$L^{-1}$ of methionine, 0.15 g/$L^{-1}$ of KMB and 2.4 g/$L^{-1}$ of HMB after 44 hours.

J. A further recombinant strain according to the invention, illustrated here-after, has also been assayed for methionine production.

YA2758MAT-a, agp3::loxP, gap1::loxP, gnp1::loxP, his3::[GDH-2.Eca-MHPF.Ec-HIS3]×5, hom3::[pADH1-HOM2, pPDC1-MET2, pRPLA1-HOM6, pENO2-MET17, pTEF3-AQR1], leu2, mae1::[ADE2.Kl, pENO2-PYC2, pTEF3-MET17, pTEF1-TPO1-1, pTDH3-METX.Cg], met19::[pENO2-MET19, pTEF3-GND1], mup3::loxP, pdc1::loxP, pdc6::loxP, pyk1::[TRP1.Kl-pTEF3-AAT2, pCUP1-1-MET19, pACU1-PEPCK-1.Ec, pMET17-PYK1], pyk2::[LEU2.Kl-pCUP1-HOM2-1], sam1::loxP, sam3::[pCUP1-1-PTA.Ls-pACU6-ACKA.Ec]×2, trp1::[pACU3p-HOM3-pACU3p-PPC-5.Ec-TRP1]×8, ura3::[pTEF3-MET17-pTDH3-PPC-5.Ec-URA3]×7

PPC-5 is a more stable form of PPC wherein an alanine has been added in N+1.

This strain was grown for 24 hours in YE (Yeast Extract) 2%, Glucose 8%, $(NH_4)_2SO_4$ 50 mM, and $CH_3SNa$ 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained is 2.2 g/$L^{-1}$, while a non-recombinant strain does not produce a detectable quantity of methionine.

K. Two recombinant strains according to the invention, illustrated here-after, have also been assayed for methionine YA4031-1: Mat a, ade2, agp3::loxP, aro8::[LEU2.Kl-RS, pCCW12-PPC-15.Ec-tRPL3, pCCW12-HOM2-1-tIDP1, pCCW12-HOM6-tRPL15A, pCCW12-METX-1.Cg-tRPL41B, pCCW12-MET17.Rp-tDIT1, pTEF3-AQR1-tRPL41B, pTEF1-TPO1-tCCW12, pCWP2-MET19-tRPL15A, pTEF1-GND1-tRPL3], gnp1::loxP, his3, leu2, mup3::loxP, pdc1::loxP, pdc6::loxP, sam1::loxP, trp1, ura3

YA4032-1: Mat a, ade2, agp3::loxP, aro8::[LEU2.Kl-RS, pCCW12-PPC-15.Ec-tRPL3, pCCW12-HOM2-1-tIDP1, pCCW12-HOM6-tRPL15A, pCCW12-METX-1.Cg-tRPL41B, pCCW12-MET17.Rp-tDIT1, pTEF3-AQR1-tRPL41B, pTEF1-TPO1-tCCW12, pCWP2-MET19-tRPL15A, pTEF1-GND1-tRPL3], gnp1::loxP, his3, leu2, mup3::loxP, pdc1::loxP, pdc6::loxP, sam1::loxP, trp1, ura3

These strains were grown in 25 ml of Yeast extract 2%, Glucose 8%, $(NH_4)_2SO_4$ 50 mM and 500 μM $Cu(SO_4)$ for seven hours, then a final concentration of 500 μM $CuSO_4$ was added and 4 ml of $CH_3SNa$ (23 g/l) were slowly added (0.25 ml/h). The content of methionine in the medium was assayed after 24h hours using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of methionine, the strain YA4031-1 produced 0.93 g·$L^{-1}$ of methionine in 24h, the strain YA4032-1 produced in the same amount of time 0.85 g·$L^{-1}$ of methionine.

L. Two strains according to the invention as presented below have been assayed for ethyl-homoserine:

DA1047: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1-lyp1]×5, mae1::[ADE2.Kl-RS, pENO2-PYC2-tTPI1, pTEF3-MET17-tCYC1, pTEF1-TPO1-1-tADH1, pTDH3-METX.Cg-tADH2]/mae1::[ADE2.Kl-RS, pENO2-PYC2-tTPI1, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, pyk2::[LEU2.Kl-RS, pCUP1-HOM2-1-tTDH3]/pyk2::[LEU2.Kl-RS, pCUP1-HOM2-1-tTDH3], sam1::loxP/sam1::loxP, tip 1::[pACU1-AAT2-tRPL3, pCUP1-1-HOM3-tIDP1, TRP1]×3/trp1::[pACU3p-HOM3-tRPL3-PPC-15.Ec-tIDP1-TRP1]×8, ura3::[pTEF3-MET17-tRPL3, pTDH3-PPC-5.Ec-tDIT1-URA3]×7/ura3::[pTEF3-MET17-tRPL3, pTDH3-PPC-5.Ec-tDIT1-URA3]×7

DA705-1: MAT-a/MAT-α, ade2/ade2, agp3::loxP/agp3::loxP, bap3::loxP/bap3::loxP, CAN1-100/can1-100, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, mae1::[ADE2.Kl-RS, pENO2-PYC2-tTPI1, pTEF3-MET17-tCYC1, pTEF1-TPO1-1-tADH1, pTDH3-METX.Cg-tADH2]/mae1::[ADE2.Kl-RS, pENO2-PYC2-tTPI1, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, sam1::loxP/sam1::loxP, trp1::[pACU1-AAT2-tRPL3, pCUP1-1-HOM3-tIDP1, TRP1]×3/trp1::[pTDH3-GDH-2.Eca-tRPL3, pCUP1-1-HOM3-tIDP1-TRP1]×5, ura3::[pTEF3-MET17-tRPL3, pTDH3-PPC-5.Ec-tDIT1-URA3]×7/ura3::[pTEF3-MET17-tRPL3, pTDH3-PPC-5.Ec-tDIT1-URA3]×7

These two strains were grown in 2% Yeast extract, 8% Glucose, 0.65 mM Histidine, 1.5 mM Adenine, 0.9 mM Uracil, 0.5 mM Tryptophane, 7.5 mM Leucine, 50 mM $(NH_4)_2SO_4$ and 500 μM $CuSO_4$ for 7 hours, then 500 μM $CuSO_4$ was added and the yeast were grown for 18 hours. The content of ethyl-homoserine in the medium was then assayed using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of ethyl-homoserine, the strain DA1047 produced 4.3 g·L-1 of ethyl-homoserine in 25h, the strain YA705-1 produced in the same amount of time 1.4 g·L-1 of ethyl-homoserine.

The invention claimed is:

1. A recombinant yeast, in the genome of which:

(A) at least one nucleic acid encoding a glucose-6-phosphate dehydrogenase is overexpressed and/or is under the control of an inducible or repressible promoter;

(B) at least one nucleic acid encoding a 6-phosphogluconate dehydrogenase, decarboxylating 1 is overexpressed and/or is under the control of an inducible or repressible promoter; and (C) (i) at least one nucleic acid encoding a phosphoenolpyruvate carboxylase that converts phosphoenol pyruvate into oxaloacetate is overexpressed and/or is under the control of an inducible or repressible promoter; and/or (ii) at least one nucleic acid encoding a phosphoenolpyruvate carboxykinase that converts phosphoenol pyruvate PEP into oxaloacetate is overexpressed and/or is under the control of an inducible or repressible promoter.

2. The recombinant yeast according to claim 1, in the genome of which:

(i) at least one nucleic acid encoding a transketolase 1 is overexpressed and/or is under the control of an inducible or repressible promoter; and/or (ii) at least one nucleic acid encoding a transaldolase 1 is overexpressed and/or is under the control of an inducible or repressible promoter.

3. The recombinant yeast according to claim 1, in the genome of which at least one nucleic acid encoding a pyruvate kinase 1 is independently:

under the control of an inducible or repressible promoter;

under the control of a weak promoter; and/or in a destabilized form.

4. The recombinant yeast according to claim 1, in the genome of which:

(i) at least one nucleic acid encoding a pyruvate kinase 2 has been deleted, and/or (ii) at least one nucleic acid encoding a pyruvate kinase 2 is under the control of an inducible or repressible promoter and/or is in a destabilized form.

5. The recombinant yeast according to claim 1, in the genome of which at least one of the following modifications has been performed:

(A) (i) at least one nucleic acid encoding a pyruvate decarboxylase isozyme 1 has been deleted, and/or (ii) at least one nucleic acid encoding a pyruvate decarboxylase isozyme 1 is under the control of an inducible or repressible promoter and/or is in a destabilized form;

(B) (i) at least one endogenous nucleic acid encoding a pyruvate decarboxylase isozyme 3 has been deleted, and/or (ii) at least one nucleic acid encoding a pyruvate decarboxylase isozyme 3 is under the control of an inducible or repressible promoter and/or is in a destabilized form;

and/or (C) (i) at least one nucleic acid encoding a pyruvate decarboxylase isozyme 2 has been deleted, and/or (ii) at least one nucleic acid encoding a pyruvate decarboxylase isozyme 2 is under the control of an inducible or repressible promoter and/or is in a destabilized form.

6. The recombinant yeast according to claim 1, in the genome of which:

(A) (i) at least one nucleic acid encoding an alcohol dehydrogenase 1 has been deleted, and/or (ii) at least one nucleic acid encoding an alcohol dehydrogenase 1 is under the control of an inducible or repressible promoter and/or is in a destabilized form;

(B) (i) at least one nucleic acid encoding an alcohol dehydrogenase 3 has been deleted, and/or (ii) at least one nucleic acid encoding an alcohol dehydrogenase 3 is under the control of an inducible or repressible promoter and/or is in a destabilized form;

(C) (i) at least one nucleic acid encoding an alcohol dehydrogenase 4 has been deleted, and/or (ii) at least one nucleic acid encoding an alcohol dehydrogenase 4 is under the control of an inducible or repressible promoter and/or is in a destabilized form;

and/or (D) (i) at least one nucleic acid encoding an alcohol dehydrogenase 5 has been deleted, and/or (ii) at least one nucleic acid encoding an alcohol dehydrogenase 5 is under the control of an inducible or repressible promoter and/or is in a destabilized form.

7. The recombinant yeast according to claim 1, in the genome of which:

(A) at least one nucleic acid encoding an acetaldehyde-CoA dehydrogenase is overexpressed and/or is under the control of an inducible or repressible promoter;

(B) at least one nucleic acid encoding an acetate kinase is overexpressed and/or is under the control of an inducible or repressible promoter; and/or (C) at least one nucleic acid encoding a phosphate acetyl transferase is overexpressed and/or is under the control of an inducible or repressible promoter.

8. The recombinant yeast according to claim 1, wherein the nucleic acid encoding a glucose-6-phosphate dehydrogenase are nucleic acid belonging to a eukaryotic organism selected, independently, from the group consisting of *Saccharomyces cerevisiae, Saccharomyces cariocanus, Saccharomyces paradoxus, Saccharomyces mikatae, Saccharomyces bayanus, Saccharomyces pastorianus, Saccharomyces boulardii, Kluveromyces lactis* and *Schizosaccharomyces pombe.*

9. The recombinant yeast according to claim 1, wherein the nucleic acid encoding a 6-phosphogluconate dehydrogenase decarboxylating 1 are nucleic acid from a eukaryotic organism preferably selected, independently, from the group consisting of *Saccharomyces cerevisiae, Saccharomyces cariocanus, Saccharomyces paradoxus, Saccharomyces mikatae, Saccharomyces bayanus, Saccharomyces pastorianus, Saccharomyces boulardii, Kluveromyces lactis* and *Schizosaccharomyces pombe.*

10. The recombinant yeast according to claim 1, wherein the nucleic acid encoding a phosphoenolpyruvate carboxylase that converts phosphoenol pyruvate PEP into oxaloacetate are nucleic acid from a prokaryote or an eukaryote.

11. The recombinant yeast according to claim 1, wherein the nucleic acid encoding a phosphoenolpyruvate carboxykinase that converts phosphoenol pyruvate PEP into oxaloacetate are nucleic acid from a prokaryote or an eukaryote.

12. The recombinant yeast according to claim 1, wherein the recombinant yeast is selected from the group consisting of the genus *Saccharomyces, Candida, Ashbya, Dekkera, Pichia* (*Hansenula*), *Debaryomyces, Clavispora, Lodderomyces, Yarrowia, Schizosaccharomyces, Cryptococcus* and *Malassezia.*

13. The recombinant yeast according to claim 1, wherein the inducible or repressible promoter is, independently, selected from the group consisting of promoters inducible or repressible with copper, promoters inducible or repressible with methionine and promoters inducible or repressible with threonine.

14. The recombinant yeast according to claim 1, wherein the weak promoter is, independently, selected from the group consisting of pURA3, pRPLA1, pNUP57 and pGAP1.

15. The recombinant yeast according to claim 1, wherein the inducible or repressible promoter is, independently, selected from the group consisting of promoters inducible or repressible with copper, promoters inducible or repressible with lysine and promoters inducible or repressible with methionine.

16. The recombinant yeast according to claim 1, wherein the inducible or repressible promoter is, independently, selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

17. The recombinant yeast according to claim 1, wherein the inducible or repressible promoter is, independently, selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

18. Method for producing at least one oxaloacetate derivative, the method comprising the steps of:

(a) culturing a recombinant yeast as defined in claim 1 in a culture medium; and (b) recovering the oxaloacetate derivative from the culture medium.

19. Method according to claim 18, wherein the at least one oxaloacetate derivative is selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine and ethyl-homoserine.

20. Method according to claim 18, wherein the culture medium comprises at least a carbon source.

* * * * *